US006359194B1

(12) United States Patent
Galvin et al.

(10) Patent No.: US 6,359,194 B1
(45) Date of Patent: Mar. 19, 2002

(54) COMPOSITIONS AND METHODS FOR THE TREATMENT AND DIAGNOSIS OF CARDIOVASCULAR DISEASE

(75) Inventors: Katherine Galvin, Cambridge; Dean A. Falb, Wellesley; Michael J. Donovan, Brookline; Dennis Huszar, Acton; Michael A. Gimbrone, Jr., Jamaica Plain, all of MA (US)

(73) Assignees: Millennium Pharmaceuticals, Inc., Cambridge; Brigham & Women's Hospital, Boston, both of MA (US)

( * ) Notice: Subject to any disclaimer, the term of this patent is extended or adjusted under 35 U.S.C. 154(b) by 0 days.

(21) Appl. No.: 09/288,292

(22) Filed: Apr. 8, 1999

Related U.S. Application Data

(63) Continuation-in-part of application No. 08/870,434, filed on Jun. 6, 1997, which is a continuation-in-part of application No. 08/799,910, filed on Feb. 13, 1997, and a continuation-in-part of application No. 08/485,573, filed on Jun. 7, 1995, now Pat. No. 5,968,770, which is a continuation-in-part of application No. 08/386,844, filed on Feb. 10, 1995, now Pat. No. 6,156,500.
(60) Provisional application No. 60/011,787, filed on Feb. 16, 1996.

(51) Int. Cl.$^7$ ..................... A01K 67/027; A01K 67/00; A01K 67/033; G01N 33/00; C12N 15/00

(52) U.S. Cl. ................................ 800/18; 800/3; 800/8; 800/13; 800/18; 800/21; 800/25; 536/23.1; 536/23.5; 435/320.1; 435/325; 435/455

(58) Field of Search ........................... 800/3, 8, 21, 13, 800/18, 25; 536/23.1, 23.5; 438/320.1, 325, 455

(56) References Cited

U.S. PATENT DOCUMENTS

| | | | |
|---|---|---|---|
| 5,202,420 A | 4/1993 | Zasloff et al. ............... 530/324 |
| 5,262,311 A | 11/1993 | Liang et al. ................ 435/91.2 |
| 5,418,162 A | 5/1995 | Blakely et al. ............. 435/348 |
| 5,422,262 A | 6/1995 | Anderson et al. ........... 435/365 |
| 5,424,187 A | 6/1995 | Shor et al. ....................... 435/6 |
| 5,545,569 A | 8/1996 | Grainger et al. ............. 436/518 |
| 5,834,248 A | 11/1998 | Falb ........................... 435/70.1 |

FOREIGN PATENT DOCUMENTS

| | | |
|---|---|---|
| EP | 0 282 899 A2 | 9/1988 |
| EP | 0 670 369 A2 | 9/1995 |
| WO | WO 95/23858 | 9/1995 |

OTHER PUBLICATIONS

Wall, 1996. Theriogenology, vol. 45, pp. 57–68.*
Mullins, et al., 1996. Journal of Clinical Investigation, vol. 98, No. 11, pp. S37–S40.*
Ebert, et al., 1988. Molecular Endocrinology, vol. 2, pp. 277–283.*

Bradley et al., 1992. Biotechnology, vol. 10, pp. 534–539.*
Barnes et al., 1994, "PCR amplification of up to 35–kb DNA with high fidelity and high yield from λ bacteriophage templates", *PNAS USA* 91:2216–2220.
Bartel et al., 1993, "Using the two–hybrid system to detect protein–protein interactions", *Cellular Interactions in Dev.* Chap. 7, pp. 153–159.
Bevilacqua et al., 1989, "Endothelial leukocyte adhesion molecule 1: an inducible receptor for neutrophils related to complement regulatory proteins and lectins", *Science* 243:1160–1165.
Bevilacqua et al., 1991, "Selectins: A family of adhesion receptors", *Cell* 67:233.
Bird et al., 1988, "Single–chain antigen–binding proteins", *Science* 242:423–426.
Blachly–Dyson et al., 1993, "Cloning and functional expression in ueast of two human isoforms of the outer mitochondrial membrane channel, the voltage–dependent anion channel", *J. Biol. Chem.* 268:1835–1841.
Black et al., 1994, "Raloxifene (LY139481 HCI) prevents bone loss and reduces serum cholesterol without causing uterine hypertrophy in ovariectomized rats", *J. Clin. Invest.* 93:63–69.
Boise et al., 1993, "bcl–x, a bcl–2–related gene that functions as a dominant regulator of apoptotic cell death", *Cell* 74:597–608.
Border & Noble, 1995, "Targeting TGF–β for treatment of disease", *Nature Med.* 1:1000–1001.
Cercek et al., 1990, "Induction of insulin–like growth factor I messenger RNA in rat aorta after balloon denudation", *Cir. Res.* 66:1755–1760.
Charles et al., 1993, "Genomic structure, cDNA sequence, and expression of gly96, a growth factor–inducible immediate–early gene encoding a short–lived glycosylated protein", *Oncogene* 8:797–801.
Chen et al., 1996, "A transcriptional partner for MAD proteins in TGF–β signaling", *Nature* 383:691–696.
Cheng et al., 1994, "Effective ampliciation of long targets from cloned inserts and human genomic DNA" *PNAS USA* 91:5695–5699.

(List continued on next page.)

*Primary Examiner*—Deborah J. R. Clark
*Assistant Examiner*—Peter Paras, Jr.
(74) *Attorney, Agent, or Firm*—Pennie & Edmonds, LLP

(57) ABSTRACT

The present invention is based on the generation and phenotypic characterization of transgenic knockout homozygous rchd534 mutant mice which display characteristic cardiovascular disease symptoms. Such transgenic knockout homozygous rchd534 mutant mice are useful models for the analysis and characterization of rchd534 protein involvement in development and homeostasis of the cardiovascular system and tissue-specific regulation of the TGF-β signaling pathways. Such transgenic mice may be used for screening compounds that may potentially useful for treating or preventing cardiovascular disease.

11 Claims, 26 Drawing Sheets

OTHER PUBLICATIONS

Figure 7A:
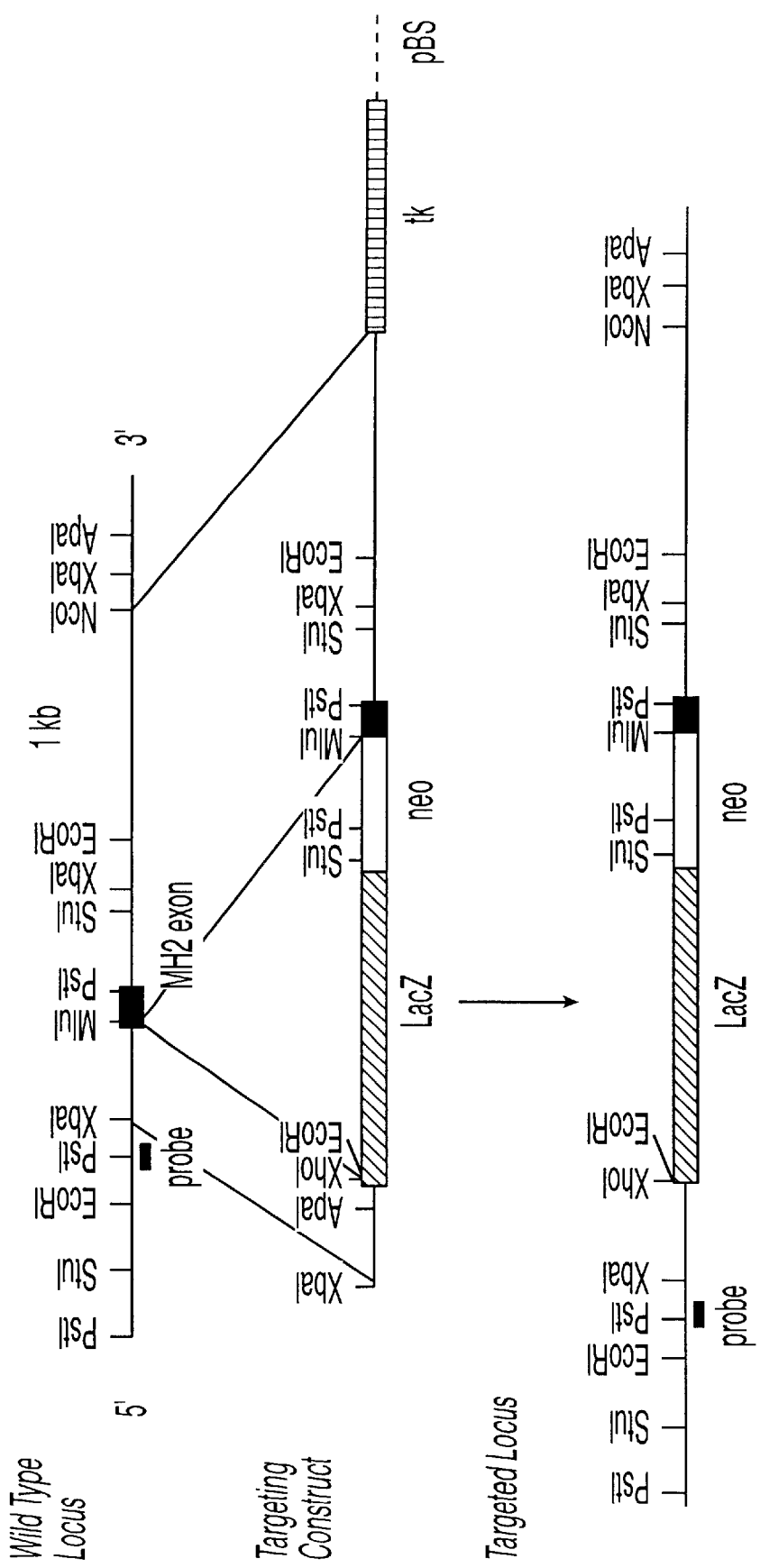
Figure 7B:
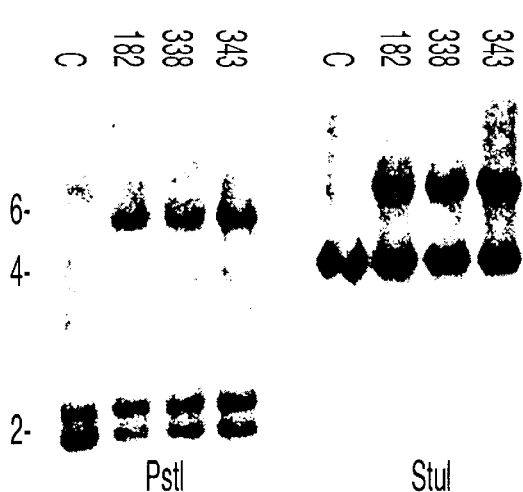
Figure 7C:
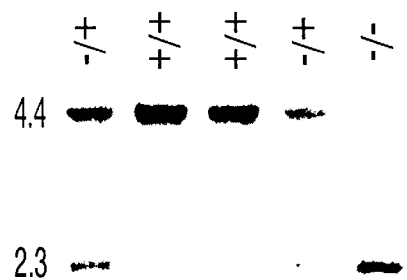

Cleary et al., 1986, "Cloning and structural analysis of cDNAs for bcl–2 and a hybrid bcl–2/Immunoglobulin transcript resulting from the t(14;18) translocation", *Cell* 47:19–28.

A Coghlan, 1995, "Gene dream fades away", *New Scientist*:14–15.

Coffman et al., 1990, "Xotch, the Xenopus homolog of *Drosophila Notch*", *Science* 249:1438–1441.

Cybulsky & Gimbrone, 1991, "Endothelial expression of a mononuclear leukocyte adhesion molecule during atherogenesis", *Science* 251:788–791.

Davies et al., 1986, "Turbulent fluid shear stress induces vascular endothelial cell turnover in vitro", *PNAS USA* 83:2114–2117.

Diamond et al., 1993, "Novel delayed–early and highly insulin–induced growth response genes", *J. Biol. Chem.* 268:15185–15192.

Eppert et al., 1996, "MADR2 maps to 18q21 and encodes a TGFβ–regulated MAD–related protein that is functionally mutated in colorectal carcinoma", *Cell* 86:543–552.

Farrow et al., 1995, "Cloning of a bcl–2 homologue of interaction with adenovirus E1B 19K", *Nature* 374:731–733.

M.A. Gimbrone, 1976, "Culture of vascular endothelium", *Progress in Hemostasis and Thrombosis* Spaet (ed.), Grune & Stratton, Inc., NY, 3:1–28.

Grainger et al., 1993, "Proliferation of human smooth muscle cells promoted by lipoprotein(a)", *Science* 260:1655–1658.

Grainger et al., 1995, "Tamoxifen elevates transforming growth factor–β and suppresses diet–induced formation of lipid lesions in mouse aorta", *Nature Med.* 1:1067–1073.

Gromadzinska & Sklodowska, 1990, "Erythrocyte glutathione peroxidase and myocardial infarction", *JAMA* 263:949–950.

Guidi et al., 1986, "Platelet glutathione peroxidase activity is impaired in patients with coronary heart disease", *Scand. J. Clin. Lab Invest.* 46:549–551.

T. Gura et al., 1995, "Estrogen: Key player in heart disease among women", *Science* 269:771–773.

Hakes & Berezney, 1991, "Molecular cloning of matrin F/G: A DNA binding protein of the nuclear matrix that contains putative zinc finger motifs", *PNAS USA* 88:6186–6190.

K. Heckl, 1988, "Isolation of cDNAs encoding human manganese superoxide dismutase", *Nuc. Acids Res.* 16:6224.

Hockenberry et al., 1993, "Bcl–2 functions in an antioxidant pathway to prevent apoptosis", *Cell* 75:241–251.

Hochman et al., 1995, "Dissociation of synchronization and excitability in furosemide blockage of epileptiform activity", *Science* 270:99–102.

Hoodless et al., 1996, "MADR1, a MAD–related protein that functions BMP2 signaling pathways", *Cell* 85:489–500.

Jones et al., 1993, "Molecular cloning of human prostaglandin endoperoxide syntase type II and demonstration of expression in response to cytokines", *J. Biol. Chem.* 268:9049–9054.

Kanai et al., 1995, "Indentification and characterization of a prostaglandin transporter", *Science* 268:866–869.

Kita et al., 1987, "Probucol prevents the progression of atherosclerosis in Watanabe heritable hyperlipidemic rabbit, and animal model for familial hypercholesterolemia", *PNAS USA* 84:5928–5931.

Kojima et al., 1991, "Lipoprotein (a) inhibits the generation of transforming growth factor β: An endogenous inhibitor of smooth muscle cell migration", *J. Cell Biol.* 113:1439–1445.

Kok et al., 1989, "Decreased selenium levels in acute myocardial infarction", *JAMA* 261:1161–1164.

Kumar & Chambon, 1988, "The estrogen receptor binds tightly to its responsive element as a ligand–induced homodimer", *Cell* 55:145–156.

Kume et al., 1992, "Lysophophatidylcholine, a component of atherogenic lipoproteins, induces mononuclear leukocyte adhesion molecules in cultured human and rabbit arterial endothelial cells", *J. Clin. Invest.* 90:1138–1144.

F. Ledley, 1995, "Nonviral gene therapy: The promise of genes as pharmaceutical products", *Human Gene Therapy* 6:1129–1144.

Li et al., 1991, "Early induction of an atherosclerosis–associated endothelial–leukocyte adhesion molecule (athero–ELAM) by an atherogenic diet in rabbits", *Arterioscler. Thromb.* 11:1397a.

Luscinskas et al., 1989, "Endothelial–leukocyte adhesion molecule–1–dependent and leukocyte (CD11/CD18)–dependent mechanisms contribute to polymorphonuclear leukocyte adhesion to cytokine–activated human vascular endothelium", *J. Immunol.* 142:2257–2263.

Majesky et al., 1990, "PDGF ligand and receptor gene expression during repair of arterial injury", *J. Cell Biol.* 111:2149–2158.

Malden et al., 1991, "The influence of oxidatively modified low density lipoproteins on expression of platelet–derived growth factor by human monocyte–derived macrophages", *J. Biol. Chem.* 266:13901–13907.

E. Marshall, , "Less hype, more biology needed for gene therapy".

E. Marshall, 1995, "Gene therapy's growing pains", *Science* 269:1050–1055.

Nagel et al., 1994, "Shear stress selectively upregulates intercellular adhesion molecule–1 expression in cultured human vascular endothelial cells", *J. Clin Invest.* 94:885–891.

Navab et al., 1988, "Monocyte migration into the subendothelial space of a coculture of adult human aortic endothelial and smooth muscle cells", *J. Clin. Invest.* 82:1853–1863.

Nikol et al., 1992, "Expression of transforming growth factor–β1 is increased in human vascular restenosis lesions", *J. Clin. Invest.* 90:1582–1592.

Ohno et al., 1994, "Gene therapy for vascular smooth muscle cell proliferation after arterial injury", *Science* 265:781–784.

Oltvai et al., 1993, "Bcl–2 heterodimerizes in vivo with a conserved homology, Bax, that accelerates programmed cell death", *Cell* 74:609–619.

Orkin & Motulsky, 1995, "Report and recommendations of the panel to assess the NIH investment in research on gene therapy", *NIH Report*.

Osborn et al., 1989, "Direct expression cloning of vascular cell adhesion molecule 1, a cytokine–induced endothelial protein that binds to lymphocytes", *Cell* 59:1203–1211.

Plump et al., 1992, "Severe hypercholesterolemia and atherosclerosis in apolipoprotein e–deficient mice created by homologous recombination in ES cells", *Cell* 71:343–353.

Porter et al., 1992, "Plasma, platelet and erythrocyte glutathione peroxidases as risk factors in ischaemic heart disease in man", *Clinical Science* 83:343–345.

Poston et al., 1992, "Expression of intercellular adhesion molecule–1 in atherosclerotic plaques", *Am. J. Pathol.* 149:665–673.

Puolakkainen et al., 1993, "Serological response to *Chlamydia pneumoniae* in adults with coronary arterial fatty streaks and fibrolipid plaques", *J. of Clinical Microbiol.* 31:2212–2214.

Raftery et al., 1988, "Genetic screens to identify elements of the decapentaplegic signaling pathway in Drosophila", *Genetics* 139:241–254.

Rapacz et al., 1986, "Lipoprotein mutations in pigs are associated with elevated plasma cholesterol and atherosclerosis", *Science* 234:1573–1577.

Resnick et al., 1993, "Platelet–derived growth factor B chain promoter contains a cis–acting fluid shear–stress–responsive element", *PNAS USA* 90:4591–4595.

R. Ross, 1993, "The pathogenesis of atherosclerosis: A perspective for the 1990s" *Nature* 362:801–809.

Sambrook et al.(eds), 1989, "Estimating the Effects of Mismatches", *Molecular Cloning—A Laboratory Manual $2^{nd}$ Edition,* p. 11.47.

Sekelsky et al., 1995, "Genetic characterization and cloning of Mothers against dpp, a gene required for decapentaplegic function in *Drosophila melanogaster*", *Genetics* 139:1347–1358.

Serra & Moses, 1996, "Tumor suppressor genes in the TGF–β signaling pathway?", *Nature Med.* 2:390–391.

Shreeniwas et al., 1991, "Reoxygenation stimulates IL–1a production, increasing leukocyte adherence to endothelium via expression of ICAM–1 and ELAM–1", *Arteriocsler. Council Abstracts* 11:1397a.

Simmons et al., 1988, "ICAM, an adhesion ligand of LFA–1, is homologous to the neural cell adhesion molecule NCAM", *Nature* 331:624–627.

Speir et al., 1994, "Potential role of human cytomegalovirus and p53 interaction in coronary restenosis", *Science* 265:391–394.

Takahashi et al., 1990, "Primary structure of human plasma glutathione peroxidase deduced from cDNA sequences", *J. Biochem.* 108:145–148.

Takayama et al., 1995, "Cloning and functional analysis of BAG–1: A novel bcl–2 binding protein with anti–cell death activity", *Cell* 80:279–284.

Tanaka et al., 1993, "Sustained activation of vascular cells and leukocytes in the rabbit aorta after balloon injury", *Circulation* 88:1788–1803.

Tsujmoto et al., 1984, "Cloning of the chromosome breakpoint of neoplastic α cells with the t(14;18) chromosome translocation", *Science* 226:1097–1099.

Wallace and Miyada, 1987, "Oligonucleotide probes for the screening of recombinant DNA libraries", *Methods in Enzymology* 152:432–443.

Wang et al., 1981, "Selenium and myocardial infarction: Glutathione peroxidase in platelets", *Klin. Wochenschr.* 59:817–818.

Wieser et al., 1995, "GS domain mutation that constitutively activate TβR–1, the downstream signaling component in the TGF–β receptor complex", *EMBO J.* 14:2199–2208.

Wilson et al., 1994, "2.2 Mb of contiguous nucleotide sequence from chromosome III of *C. elegans*", *Nature* 368:32–38.

Wrana et al., 1994, "Mechanism of activation of the TFG–β receptor", *Nature* 370:341–347.

Xu et al., 1994, "Molecular cloning and functional expression of the bumetanide–sensitive Na–K–Cl cotransporter", *PNAS USA* 91:2201–2205.

Yoshimura et al., 1994, "The human plasma glutathione peroxidase–encoding gene: Organization, sequence and localization of chromosome 5q32", *Gene* 145:293–297.

Patrick Jr., et al. ,1995, "Shear stress and cyclic strain moduclation of gene expression in vascular endothelial cells", *Blood Purification* 13:112–124.

Shyy et al., 1995, "Multiple cis–elements mediate shear stress–induced gene expression", *J. Biomechanics* 28:1451–1457.

Weatherall, D.J., 1995, "Scope and limitations of gene therapy", *British Medical Bulletin* 51:1–11.

International Search Report, Application No. PCT/US97/02291, dated Jul. 11, 1997.

Fuller et al., 1996, "Genetic Engineering of Cardiac Muscle Cells: In Vitro and In Vivo", *Seminars in Oncology*, 23:4–21.

Mastrangelo et al., 1994, "Gene Therapy for Human Cancer: An Essay for Clinicians", 16:17–25.

Ngo et al., 1994, "Computational Complexity, Protein Structure Prediction, and the Levinthal Paradox", The Protein Folding Problem and Tertiary Structure Prediction, Merz et al., (ed.), Birkhauser, Boston, MA pp. 433 and 492–495.

Papadaki et al., 1997, Effects of Fluid Shear Stress on Gene Regulation of Vascular Cells, Biotechnol. Prog. 13:209–221.

Liew et al., Gene Bank (AN:T20268, D345F *Homo sapiens* cDNA clone D345, Nov. 28, 1994).

Liew et al., "A catalogue of genes in the cardiovascular system as identified by expressed sequence tags" 1994, *PNAS,* 91:10645–10649.

Kondratyev, et al., 1996, "Identification and Characterization of a Radiation–inducible Glycosylated Human Early–Response Gene", *Cancer Research* 56:1498–1502.

Afrakhte et al., 1998, *Biochem. Biophys. Res. Commun.* 249, 505–511.

Boon et al., 1997, *Heart* 78(5):472–474.

Boyer et al., 1999, *Dev. Dyn.* 214:81–91.

Cohen et al., 1988, *J. Pharmacol. Exp. Ther.* 244: 550–555.

Eisenberg et al., 1995, *Circ. Res.* 77:1–6.

Hata et al., 1998, *Genes Dev.* 12:186–197.

Huang et al., 1995, *Ann. N.Y. Acad. Sci.* 752:317–330.

Imamura et al., 1997, *Nature* 389:622–626.

Kaartinen et al., 1995, *Nat. Genet.* 11:415–421.

Li et al., 1998, *Hypertension* 33:271–275.

Lindroos et al., 1993, *J. Am. Coll. Cardiol.* 21(5):1220–1225.

Marchuk, D.A., 1998, *Curr. Opin Hematol* 5:332–338.

Mohler et al., 1997, *Arterioscler. Thromb. Vasc. Biol.* 17(3):547–552.

Moore et al., 1998, *Dev. Dyn.* 212:548–562.

Nakajima et al., 1998, *Dev. Bio.* 194:99–113.

Nomura et al., 1988, *Nature* 393:786–790.

Oshima et al., 1996, *Dev. Biol.* 179:297–302.

Perrella et al., 1998, *Miner Electrolyte Metab* 24:136–143.

Proetzel et al., 1995, *Nat. Genet.* 11:409–414.

Ramsdell et al., 1997, *Dev. Biol.* 188:64–74.

Sanford et al., 1997, *Development* 124:2659–2670.

Schulick et al., 1998, *Proc. Natl. Acad. Sci.* 95:6983–6988.

Takase et al., 1998, *Biochem. Biophys. Res. Commun.* 244:26–29.

Topper et al., 1997, *Proc. Natl. Acad. Sci.* 94:9314–9319.

Watson et al., 1994, *J. Clin. Invest.* 93:2106–2113.

* cited by examiner

```
                                                                                                            4
GGCACGAGTCGGAGCCGGG                                                                                        12

CGGAGGGGAGGGGGAAAGAGGAGCGCAGGGTGAGAGTGAGCCGCAGGCTTCGGGAGGGCGAGGGGCGGGGGGAGCAGC

M   P   G   E                                                                              24
GCCGAGGYCGCCGCCTCCGCCTCCGCGCCTAGGACTAGGGGGTGGGGACGGACAAGCCCCG ATG CCG GGG GAG                              72

T   E   P   R   P   P   E   Q   Q   D   Q   E   G   E   A   A   K   A                                    44
ACG GAA GAG CCG AGA CCC CCG GAG CAG CAG GAC CAG GAA GGG GAG GCC AAG GCG                                   132

A   P   E   E   P   Q   Q   R   P   P   E   A   V   A   A   A   P   A   G   T                            64
GCT CCG GAG GAG CCC CAA CAA CGG CCC CCT GAG GCG GTC GCG GCG GCG CCT GCA GGG ACC                           192

T   S   S   R   V   L   R   G   G   D   R   G   R   A   A   A   A   A                                    84
ACT AGC AGC CGC GTG CTG AGG GGA GGT CGG GAC CGG GGC CGG GCC GCT GCG GCC GCC                               252

A   A   V   S   R   R   K   A   E   Y   P   R   R   A   K   S   P                                       104
GCC GCA GCT GTG TCC CGC AGG AAG GCC GAG TAT CCC CGC CGG AGG AAG AGC CCC                                  312

S   A   R   P   P   D   V   P   G   Q   Q   P   Q   A   A   K   V   T   T   D   K   P                   124
AGC GCC AGG CCT CCC GAC GTC CCC GGG CAG CAG CCC CAG GCC GCG AAG GTA ACA ACT GAT AAA CCG                  372

V   Q   G   K   K   S   P   R   L   L   C   I   E   K   V   T   Q   P   L                                144
GTT CAG GGC AAG AAG AGT CCG CGA CTC CTA TGC ATA GAA AAA GTA ACA CAG CCT CTC                              432

P   K   E   E   K   E   E   D   D   S   A   L   P   Q   E   V   S   I   A
CCC AAG GAA GAA AAA GAG GAA GAC GAT TCT GCC CTC CCT CAG GAA GTT TCC ATT GCT
```

FIG.1A

```
  A   S   R   P   S   R   G   W   R   S   S   R   T   S   V   S   R   H   R   D    164
  GCA TCT AGA CCT AGC CGG GGC TGG CGT AGT AGT AGG ACA TCT GTT TCT CGC CAT CGT GAT   492

T   E   N   T   R   S   R   S   K   T   G   S   L   Q   L   I   C   K   S         184
  ACA GAG AAC ACC CGA AGC TCT CGG TCC AAG ACC GGT TCA CAG CTC ATT TGC AAG TCA        552

E   P   N   T   D   Q   L   D   Y   D   V   G   E   H   Q   S   P   G   G         204
  GAA CCA AAT ACA GAC CAA CTT GAT TAT GAT GTT GGA GAG CAT CAG TCT CCA GGT GGC        612

I   S   G   E   E   E   E   E   E   E   E   E   M   L   I   S   E   E   I         224
  ATT AGT GGT GAA GAG GAA GAG GAA GAA GAG GAA GAG ATG TTA ATC AGT GAA GAG ATA        672

P   F   K   D   D   P   R   D   E   T   Y   K   E   E   H   L   E   T   P         244
  CCA TTC AAA GAT GAT CCA AGA GAT GAG ACC TAC AAA GAA GAG CAC TTA GAA ACC CCA        732

K   P   R   R   K   S   G   K   V   K   E   E   N   E   K   E   I   K   V         264
  AAG CCA CGG AGA AAA TCA GGG AAG GTA AAA GAA GAG AAT GAA AAG GAA ATT AAA GTG        792

E   V   E   V   K   E   V   K   E   E   D   K   S   P   R   L   P   E   P         284
  GAA GTA GAG GTG AAA GAG GTA AAA GAA GAG GAT AAA AGT CCA CGT TTA CCC GAG CCT        852

R   K   R   G   R   R   R   K   D   K   E   M   E   G   T   G   R   R   K         304
  AGG AAG AGA GGA AGA AGA CGA AAA GAT GAC AAA AGT GAA GGA ACT CGT AGG AGA AAA        912

K   P   P   I   Q   Y   V   R   C   E   M   E   G   C   G   T   V   L   A   H     324
  AAG CCT CCA ATC CAG TAT GTC CGT TGT GAG ATG GAA GGA TGT GGA ACT GTC CTT GCC CAT    972
```

FIG. 1B

| | | | | | | | | | | |
|---|---|---|---|---|---|---|---|---|---|---|
| P | R | Y | L | Q | H | H | I | K | Y | Q | H | L | L | K | K | Y | V | C | 344 |
| CCT | CGC | TAT | TTG | CAG | CAC | CAC | ATT | AAA | TAC | CAG | CAT | TTG | CTG | AAG | AAG | TAT | GTA | TGT | 1032 |
| P | H | P | S | C | R | G | L | F | R | L | Q | K | Q | L | R | H | A | K | 364 |
| CCC | CAT | CCC | TCC | TGT | GGA | CGA | CTC | TTC | AGG | CTT | CAG | AAG | CAA | CTT | CGA | CAT | GCC | AAA | 1092 |
| H | T | D | Q | R | D | Y | I | C | E | Y | C | A | R | A | F | K | S | S | 384 |
| CAT | ACA | GAT | CAA | AGG | GAT | TAT | ATC | TGT | GAA | TAT | TGT | GCT | CGG | GCC | TTC | AAG | AGT | TCC | 1152 |
| H | N | L | A | V | H | R | M | I | H | T | G | E | K | P | L | Q | C | E | I | 404 |
| CAC | AAT | CTG | GCA | GTG | CAC | CGG | ATG | ATT | CAC | ACT | GGC | GAG | AAG | CCA | TTA | CAA | TGT | GAG | ATC | 1212 |
| C | G | F | T | C | R | Q | C | K | A | S | L | N | W | H | M | K | K | F | E | I | A | 424 |
| TGT | GGA | TTT | ACT | TGT | CGA | CAA | AAG | GCA | TCT | CTT | AAT | TGG | CAC | ATG | AAG | AAA | TTT | GAG | ATC | GCA | 1272 |
| D | S | F | Y | Q | H | K | A | I | T | S | C | N | I | C | G | K | V | F | E | K | D | S | 444 |
| GAC | TCC | TTC | TAC | CAG | CAC | AAG | GCA | ATC | ACC | AGC | TGC | AAT | ATC | TGT | GGC | AAA | GTG | TTT | GAG | AAG | GAC | AGC | 1332 |
| V | A | H | K | A | L | I | T | D | I | L | G | T | N | P | E | K | A | L | A | 464 |
| GTA | GCA | CAC | AAG | GCA | CTC | ATC | ACC | GAT | ATC | TTG | GGC | ACT | AAC | CCA | GAG | AAG | GCT | CTG | GCT | 1392 |
| N | A | G | A | D | G | Q | L | L | P | E | L | P | E | S | T | A | 484 |
| AAT | GCA | GGC | GCC | GAT | GGT | CAG | CTT | CTT | CCT | GAG | CCC | TTG | GAG | TCC | ACG | GCC | 1452 |
| Q | P | S | D | G | Q | L | P | L | L | G | N | S | T | S | 504 |
| CAG | CCT | TCA | GAT | GGT | CAG | CCC | CTT | CTT | GGA | AAC | TCA | ACC | TCT | 1512 |

FIG.1C

```
G   E   C   L   L   L   E   A   E   G   M   S   K   S   Y   C   S   G   T   E     524
GGA GAG TGC CTA CTG TTA GAA GCT GAA GGG ATG TCA AAG TCA TAC TGC AGT GGG ACG GAA    1572

R   V   S   L   M   A   D   G   K   I   F   V   G   S   S   G   S   G   G   T     544
CGG GTG AGC CTG ATG GCT GAT GGG AAG ATC TTT GTG GGA AGC GGC AGT GGA GGC ACT        1632

E   G   L   V   M   N   S   D   I   L   G   A   T   E   V   L   I   E   D         564
GAA GGG CTG GTT ATG AAC TCA GAT ATA CTC GGT GCT ACC ACA GAG GTT CTG ATT GAA GAT    1692

S   D   S   A   G   P   *                                                          570
TCA GAC TCT GCC GGA CCT TAG TGGACAGGAAGACTTGGGGCATGGGACAGCTCAGACTTTGTATTTAAAAGT    1761

TAAAAAGGACAAAAAAAAAAAAAAAAAA                                                       1791
```

FIG.1D

```
                                                                                              2
                                                                                      M   F   6
CGACTCACAAAGAAACATCATGTTCGCTCCTTAGCAGGCAAAGGACTTTTCTCCTGCCCTCCTGCCCCGC ATG TTC

R   T   K   R   S   A   L   V   R   R   L   W   R   S   R   A   P   G   G   E      22
AGG ACC AAA CGA TCT GCG CTC GTC CGG CGT CTC TGG AGG AGC CGT GCG CCC GGC GGG GAG      66

D   E   E   G   G   A   H   G   G   G   G   G   P   G   R   A   G   C   L          42
GAC GAG GAG GGC GCA CAT GGT GGC GGA GGT GGC GGC CCG AGG GCT GGA TGC CTG             126

T   D   S   R   A   V   R   G   G   A   K   G   H   H   H   P   H   P   A   L      62
ACG GAC AGC CGA GCG GTG CGA GGT GCC AAA GGT CAC CAC CAT CCC CAC CCG GCT           186

G   K   A   V   R   G   A   E   G   A   E   D   L   K   A   L   T   H   S   V   L   K   A   82
GGC AAG GCG GTG CGA GGT GCC GAG GGC GCC GAG GCG GAT CTG AAG GCG CTC ACG CAC TCG GTG CTC AAG GCG  246

G   A   G   G   A   E   D   L   Q   L   L   A   V   E   S   R   G   A        102
GGC GCC GGG GCC GAG GCG GAT CTG CAG CTC CTG GCC GTG GAG TCC CGC GGC GCC          306

L   K   E   R   Q   L   E   L   Q   L   L   E   L   Q   L   L   Q   L   K   T   R      122
CTG AAG GAG CGG CAG CTG GAG CTG CAG CTC CTG GAG CTG CAG CTC CTG CAG CTG AAG ACG CGC       366
```

FIG.2A

```
T   A   C   L   L   P   G   R   L   D   C   R   L   G   P   G   A   P   A
ACC GCG TGC CTC CTG CCC GGC CGC CTG GAC TGC AGG CTG GGC CCG GGG GCG CCC GCC    142
                                                                               426

G   A   Q   P   A   Q   P   P   S   Y   S   L   P   L   L   C   L   K   V
GGC GCG CAG CCT GCG CAG CCG CCC TCG TCC TAC TCG CTC CCC CTC TGC CTG AAA GTG    162
                                                                               486

F   R   W   P   D   L   R   H   S   S   E   V   K   R   L   C   C   E   S
TTC AGG TGG CCG GAT CTC AGG CAT TCC TCG GAA GTC AAG AGG CTG TGT TGT GAA TCT    182
                                                                               546

Y   G   K   I   N   P   E   L   V   C   N   P   H   H   L   C   S   L   C
TAC GGG AAG ATC AAC CCC GAG CTG GTG TGC AAC CCC CAT CAC CTG TGC AGC CTC TGC    202
                                                                               606

E   L   E   S   P   P   P   P   Y   S   R   Y   P   M   D   F   L   P   T
GAA CTA GAG TCT CCC CCT CCT CCT TAC TCC AGA TAC CCG ATG GAT TTT CTC AAA CCA ACT 222
                                                                               666

A   D   C   P   D   A   V   P   S   A   L   L   T   G   G   D   R   S   Y   L   A
GCA GAC TGT CCA GAT GCT GTG CCT TCC CAA CTT CTT CTG GCT GAA ACA GGG GAT CGG TCA ACG AAT TAT CTG GCC 242
                                                                               726

P   G   G   L   S   D   E   E   K   T   R   V   G   R   L   Y   C   V   E   P
CCT GGG GGG CTT TCA GAT GAG GAG AAG ACG AGA GTG GGG AGG CTC TAC TGT GTC CAG GAG CCC    262
                                                                               786

V   V   A   Y   W   E   P   G   R   L   Y   C   L   G   Q   N   C   H   W   C
GTG GTG GCA TAC TGG GAG CCT CGG AGG CTC TGT CAC TGC TGG CAG CAG CCC    282
                                                                               846

S   L   D   I   F   Y   D   L   P   Q   G   N   G   F   C   L   G   Q   L   N
TCT CTG GAT ATC TTC TAT GAT CTA CCT CAG GGG AAT GGC TTT TGC CTC GGA CAG CTC AAT 302
                                                                               906
```

FIG.2B

```
  S   D   N   K   S   Q   L   V   Q   K   V   R   S   K   I   G   C   G   I   Q   322
TCG GAC AAC AAG AGT CAG CTG GTG CAG AAG GTG CGG AGC AAA ATC GGC TGC GGC ATC CAG   966

L   T   R   E   V   D   G   V   W   V   Y   N   R   S   S   Y   P   I   F   I   342
CTG ACG CGG GAG GTG GAT GGT GTG TGG GTG TAC AAC CGC AGC AGT TAC CCC ATC TTC ATC  1026

K   S   A   T   L   D   N   P   D   S   R   T   L   L   V   H   K   V   F   P   362
AAG TCC GCC ACA CTG GAC AAC CCT GAC TCC AGG ACG CTG TTG GTA CAC AAG GTG TTC CCC  1086

G   F   S   I   K   A   F   D   Y   E   K   A   Y   S   L   Q   R   P   N   D   382
GGT TTC TCC ATC AAG GCT TTC GAC TAC GAG AAG GCG TAC AGC CTG CAG CGG CCC AAT GAC  1146

H   E   F   M   Q   Q   P   W   T   G   F   T   V   Q   I   S   F   V   K   G   402
CAC GAG TTT ATG CAG CAG CCG TGG ACG GGC TTT ACC GTG CAG ATC AGC TTT GTG AAG GGC  1206

W   G   Q   C   Y   T   R   Q   F   I   S   S   C   P   C   W   L   E   V   I   422
TGG GGT CAG TGC TAC ACC CGC CAG TTC ATC AGC AGC TGC CCG TGC TGG CTA GAG GTC ATC  1266

F   N   S   R   *                                                               426
TTC AAC AGC CGG TAG   CCGCGTGCGGAGGGGACAGAGGCGTGAGCTGAGCAGGCCACACTTCAAACTACTTTGCT 1278

GCTAATATTTCCTCCTGAGTGCTTGCTTTTCATGCAAACTCTTTGGTCTTTTTTTTGTTGTTGGTTGGTTTTCT

TCTTCTCGTCCTCGTTTGTGTTCTGTTTGTTTGCTCTTTGAGAAATAGCTTATGAAAAGAATTGTTGGGGTTTTT

TGGAAGAAGGGGCAGGTATGATCGGCAGGACACCCTGATAGGAAGAGGGGAAGCAGAAATCCAAGCACCACCAAACACA
```

FIG.2C

```
GTGTATGAAGGGGGGGGTCATCATTTCACTTGTGTCAGGAGTGTGTGTGAGTGTGAGTGTGCGGCTGTGTGTGCACGCGT
GTGCAGGAGCGGCAGATGGGGAGACAACGTGCTCTTTGTTTGTGTCTCTTATGGATGTCCCAGCAGAGAGGTTTGCA
GTCCCAAGCGGTGTCTCCTGCCCCTTGGACACGCTCAGTGGGGCAGAGGCAGTACCTGGGCAAGCTGGGCGGCTGGGG
TCCCAGCAGCTGCCAGGAGCACGGCTCTGTCCCCAGCCTGGGAAAGCCCCTGCCCCTCCTCCTCCTCATCAAGGACACG
GGCCTGTCCACAGGCTTCTGAGCAGCGAGCCTGTAGTGGCCGAACCAGAACCAATTATTTCATCCTTGTCTTATTCC
CTTCCTGCCAGCCCTGCCATTGTAGGGTCTTTCTTTTTGGCCATCTGCTCCTGGATCTCCCTGAGATGGGCTTCCCA
AGGGCTGCCGGGGCAGCCCCTCACAGTATTGCTCACCCAGTGCCCTCTCCCCTCAGCCTCTCCCCTGCCTGCCCTGGT
GACATCAGGTTTTTCCCGGACTTAGAAAAACCAGCTCCTGGGAGGACATGCTTAGCAGTCCCCTTCCCTCCAAGAGGATTTGGTCCGTCATAAC
GCCAGCAAGCGGGGATGTCCCTGGGAGGACATGCTTAGCAGTCCCCTTCCCTCCAAGAGGATTTGGTCCGTCATAAC
CCAAGGTACCATCCTAGGCTGACACCTAACTCTTCTTTCATTTCTTCTACAACTCATACACTCGTATGATACTTCGACA
CTGTTCTTAGCTCAATGAGCATGTTTAGACTTTAACATAAGCTATTTTTCTAACTACAAAGGTTTAAATGAACAAGAGA
AGCATTCTCATTGGAAATTTAGCATTGTAGTGCTTTGAGAGAGAAAGGACTCCTGAAAAAAAAAACCTGAGATTTATTAAA
GAAAAAAATGTATTTTATGTTATATATAAATATATTATTACTTGTAAATATAAAGACGTTTTATAAGCATCATTATTTA
```

FIG.2D

TGTATTGTGCAATGTGTATAAACAAGAGAAAAATAAAGAAAAAGATGCACTTTGCTTTAATATAAATGCAAATAACAAATGC

CAAATTAAAAAGATAAACACAAGATTGGTGTTTTTTCCTATGGGTGTTATCACCTAGCTGAATGTTTTTCTAAAGGAG

TTTATGTTCCATTAAAACGATTTTTAAAATGTACACTTGAAAAAAAAAAAAAAAAA

FIG.2E

```
                      GGCACGAGGTTGCCCTGGCGGAGCAGAGACAGGCCCTCGGGGTGGAGGTC

M   C   N   T   P   T   Y   C   D   L          10
                     ATG TGT AAC ACA CCA ACG TAC TGT GAC CTA         30

G   K   A   A   K   D   V   F   N   K   G   Y   G   F   G   M   V   K   I   D          30
GGA AAG GCT GCT AAG GAT GTC TTC AAC AAA GGA TAT GGC TTT GGC ATG GTC AAG ATA GAC         90

L   K   T   K   S   C   S   G   V   E   F   S   T   S   G   H   A   Y   T   D          50
CTG AAA ACC AAG TCT TGT AGT GGA GTG GAA TTT TCT ACT TCT GGT CAT GCT TAC ACT GAT        150

T   G   K   A   S   G   N   L   E   T   L   K   Y   K   V   C   N   Y   G   L   T      70
ACA GGG AAA GCA TCA GGC AAC CTA GAA ACC CTA AAA TAT AAG GTC TGT AAC TAT GGA CTT ACC    210

F   T   Q   K   W   N   T   D   N   T   L   G   T   E   I   S   W   E   N   K          90
TTC ACC CAG AAA TGG AAC ACA GAC AAT ACT CTA GGG ACA GAA ATC TCT TGG GAG AAT AAG        270

L   A   E   G   L   K   L   L   D   T   I   F   V   P   N   T   G   K   K            110
TTG GCT GAA GGG TTG AAA CTG CTG GAT ACC ATA TTT GTA CCG AAC ACA GGA AAG AAG            330

S   G   K   L   K   A   S   Y   K   R   D   C   F   S   V   G   S   N   V   D        130
AGT GGG AAA TTG AAG GCC TCC TAT AAA CGG GAT TGT TTT AGT GTT GGC AGT AAT GTT GAT        390

I   D   F   S   G   P   T   I   Y   G   W   A   V   L   A   F   E   G   W   L        150
ATA GAT TTT TCT GGA CCA ACC ATC TAT GGC TGG GCT GTG TTG GCC TTC GAA GGG TGG CTT        450
```

FIG. 3A

```
 A   G   Y   Q   M   S   F   D   T   A   K   S   K   L   S   Q   N   N   F   A    170
GCT GGC TAT CAG ATG AGT TTT GAC ACA GCC AAA TCC AAA CTG TCA CAG AAT AAT TTC GCC   510

L   G   Y   K   A   A   D   F   Q   L   H   T   H   V   N   D   G   T   E   F    190
CTG GGT TAC AAG GCT GCG GAC TTC CAG CTG CAC ACA CAT GTG AAC GAT GGC ACT GAA TTT   570

G   G   S   I   Y   Q   K   V   N   E   K   I   E   T   S   I   N   L   A   W    210
GGA GGT TCT ATC TAC CAG AAG GTG AAT GAG AAG ATT GAA ACA TCC ATA AAC CTT GCT TGG   630

T   A   G   S   N   N   T   R   F   G   I   A   A   K   Y   M   L   D   C   R    230
ACA GCT GGG AGT AAC AAC ACC CGT TTT GGC ATT GCT GCT AAG TAC ATG CTG GAT TGT AGA   690

T   S   L   S   A   K   V   N   N   A   S   L   I   G   L   Y   T   Q   T        250
ACT TCT CTC TCT GCT AAA GTA AAT AAT GCC AGC CTG ATT GGA CTG TAT ACT CAG ACC       750

L   R   P   G   V   K   L   T   L   S   A   L   F   E   L   E   A   *            270
CTT CGA CCA GGA GTC AAA TTG ACT TTA TCA GCT TTA GAA CTG GAA GCT TAA               810

G   G   H   K   V   G   L   G   F                                                283
GGA GGT CAC AAG GTT GGC TTG GGA TTT                                               849
```

TTTGTCCCTGGAAGTGAAGAGAAATGAACCCACTATGTTTTGGCCTTAAAATTCTTCTGTGAAATTTCAAAAGTGTGAA

CTTTTTATTCTTCCAAAGAATTGTAATCCTCCCACACTGAAGTCTAGGGGTTGCGAATCCCTCCTGAGGGAGACGCTT

GAAGGCATGCCTGAAGTTGTCATGTTTGTGCCACGTTTCAGTTCTCGAAGTTCAGTTGTTATTAAATGTGTCCTCAGCG

FIG.3B

ACAGTGTAGGCGTCATGTGTTAGAGAGGAGACGATCTGACCCACCACCAGTTTGTACATCACGTCCTGCATGTCCCACACCATTTTT

TCATGACCCTTGTAATATACTGGTCTCTGTGTGCTATAGTGGAATCTTTGGTTTTGCATCATCATAGTAAAATAAAATAAACCCA

TCACATTTGGAACATAAAAAAAAAAAAAAAAAAA

FIG.3C

```
T   S   L   A   L   V   L   N   L   L   Q   I   Q   R   N   V   T   L   F   P          20
ACG AGC CTA GCC CTG GTG CTC AAC CTG CTG CAG ATC CAG AGG AAT GTC ACT CTC TTC CCC         60

E   E   V   I   A   T   I   F   S   S   A   W   V   P   C   G   T                       40
GAG GTG ATC GCC ACC ATC TTT TCC TCC GCC TGG TGG TGC CCC TGC GGG ACA                     120

A   A   V   V   G   L   Y   P   C   I   D   S   H   L   G   E   P   H                   60
GCA GCT GTT GTT GGC CTA CTG TAC CCC TGT ATC GAC AGT CAC CTC GGA GAA CCC CAC             180

K   F   K   R   E   W   A   S   V   M   R   C   I   A   F   V   G   I   N              80
AAA TTT AAG AGA GAA TGG GCC AGT GCC ATG CGC ATA GCA GTT TTT GGC ATT AAC                 240

H   A   S   A   K   L   D   F   N   V   Q   L   S   L   T   L   A   A                  100
CAC AGT GCC GCT AAA TTG GAT TTT GCC AAT AAT GTC CAG CTG TCC TTG ACT TTA GCA GCC         300

L   S   L   G   L   W   T   F   D   R   S   G   R   S   G   L   G                      120
CTA TCT TTG GGC CTT TGG ACA TTT GAT CGT TCC AGA AGT GGC GGG CTG GGG ATC                 360

T   I   A   F   L   A   T   L   Y   I   R   S   W   L   P   V   N   G   Y   Q          140
ACC ATA GCT TTT CTA GCT ACG CTG TAT ATT CGT TCT TGG CTC CCT GTG AAT GGT TAT CAG         420

Y   T   S   P   D   F   L   Y   L   I   C   I   F   F   S   G                          160
TAT ACA TCC CCA GAT TTC CTC TAT CTT TGT ATA TTC TTC TCA GGA                             480

G   V   T   V   G   N   I   G   R   Q   L   A   M   G   V   P   E   K   P   H          180
GGC GTC ACG GTG GGG AAC ATA GGA CGA CAG CAG TTA GCT ATG GGT GTT CCT GAA AAG CCC CAT     540
```

FIG. 4A 182
546

S    D    *
AGT GAT TGA GTCTTCAAAACCACCGATTCTGAGAGCAAGGAAGATTTGGAAGAAATCTGACTGTGGATTATGAC

AAGATTATCTTTTTCTTAAGTAATCTATTTAGATCGGGCTGACTGTACAAATGACTCCTGGAAAAACTCTTCACCT

AGTCTAGAATAGGGAGGTGGAGAATGATGACTTACCCTGAAGTCTTCCCTTGACTGCCCGCCACTGGCGCCTGTCTGTGC

CCTGGAGCATTCTGCCCCAGGCTACGTGGGTTCAGGCAGGTGGCAGCTTCCCAAGTATTCGATTTCATTCATGTGATTAA

AACAAGTTGCCATATTTCAAAAAAAAAAAAMCTCGAGACCAACCGCAGTTTTGTGTCAGTGCCCAAAGGAGGT

AGGTTGATGGTGCTTAACAAACATGAAGTATGGTGTAATAGGAATAATATTTATCCNAAAGATTTTTAAAAATAGGGCT

GTGTTTAAAAAAAAAAAAAAAAAAA

FIG.4B

```
      M   C   H   S   R   S   C   H   P   T   M   T   I   L   Q   A   P   T   P   A      20
      ATG TGT CAC AGC CGC TCT TGC CAC CCG ACC ATG ACC ATC CTG CAG GCC CCG ACC CCG GCC      60

P   S   T   I   P   G   P   R   R   G   S   G   P   E   I   F   T   F   D   P      40
      CCC TCC ACC ATC CCG GGA CCC CGG CGG GGC TCC GGT CCT GAG ATC TTC ACC TTC GAC CCT      120

L   P   E   P   A   A   A   P   A   G   R   P   S   A   S   R   G   H   R   K      60
      CTC CCG GAG CCC GCA GCA GCG GCC CCT GCC GGG CGC CCC AGC GCC TCT CGC GGG CAC CGA AAG  180

R   S   R   R   V   L   Y   P   R   V   V   R   Q   L   P   C   P   V   E   E   P   80
      CGC AGC CGC AGG GTT CTC TAC CCT CGA GTG GTC CGG CAG CTG CCA GTC TGC GAG GAA CCG      240

N   P   A   K   R   L   L   F   L   L   T   L   I   V   F   Q   I   L   M      100
      AAC CCA GCC AAA AGG CTT CTC TTT CTG CTC ACC CTG ATC GTC TTC CAG ATC CTG ATG          300

A   E   G   V   P   A   L   P   A   P   P   E   D   A   P   N   A   A   S   L      120
      GCT GAA GAG GGT GTG CCG GCG CTG CCC CCT CCA GAG GAC GCC CCT AAC GCC GCA TCC CTG      360

A   P   T   P   V   S   P   V   L   E   P   L   Q   P   F   N   L   T   S   E   P   S   D  140
      GCG CCC ACC CCT GTG TCC CCC GTC CTC GAG CCC CTC CAG CCC TTT AAT CTG ACT TCG GAG CCC TCG GAC 420

Y   A   L   D   L   S   T   F   L   Q   Q   H   P   A   A   F   *                 157
      TAC GCT CTG GAC CTC AGC ACT TTC CTC CAG CAA CAC CCG GCC GCC TTC TAA                 471

CTGTGACTCCCCGCACTCCCCAAAAGAATCGAAAAGAACACAAGAAAACCACCAGGCGTACCTGGTGCCGAGAGCGTA      550
```

FIG.5A

```
TCCCCAACTGGGACTTCCGAGGCAACTTGAACTCAGAGAACACTACAGCGGAGACGCCACCCGGTGCTTGAGGCGGGGACCG    629

AGGCGCACAGAGACCGAGGCGCATAGAGACCGAGGCACAGCCCAGCTGGGGCTAGGCCCGGTGGGAAGGAGAGAGGCGTCGT    708

TAATTTATTTCTTATTGCTCCTAATTAATATATTTATGTATTTATGTACGTCCTCCTAGGTGATGGAGATGTGTACGTA      787

ATATTTATTTTAACTTATGCAAGGGTGTGAGATGTTCCCTCTGCTAAATGCAGGTCTCTTGGTATTTATTGAGCTTT         866

GTGGGACTGGTGGAAGCAGGACACCTGGAACTGCGGCAAAGTAGGAGAAGAATGGGAGGACTCGGGTGGGGGAGGAC        945

GTCCCGGCTGGATGAAGTCTGGTGGTGGGTCGTAAGTTTAGGAGAGGTGACTGCCATCCTCCAGCATCTCAACTCCGTCTG   1024

TCTACTGTGTGAGACTTCGGCGGACCATTAGGAATGAGATCCGTGAGATCCTTCCATCTTCTTGAAGTCGCCTTTAGGG     1103

TGGCTGCGAGGTAGAGGGTTGGGGGTTGGTGGGCTGTCACGGAGCGACTGTCGAGATCGCCTAGTATGTTCTGTGAACA     1182

CAAATAAAATTGATTTACTGTCAAAAAAAAAAAAAAAAAACTCGAG                                      1228
```

FIG.5B

```
GAATTCGGCACGAGGMCAGGAGCTCCTTWCTGGTCTCCCATCATGGGGCTTAGGGTTGAGTCTTCA      68

GGTTCTGGGGGCAGGAAGGACGGGCACTCAGGAGGCCCCCTCCCCATCCACAGCCCCTCTTTGGGAGGGGGAAACTTG     147

GCAACCCGGGAGGCATGTGGATCTTTTCCTAAGCAAGATGCTGAGCTGGAAAGATGGGGGTGTAAGGTAATGTCCCAAA     226

CTGAAACTTTGCCAGGCACTGGGAGAGGCTGTGAACTCTTTCTGGCTTAGAATTTAGGTCTAGATCCCAAAAGGCTA     305

AGTACCCCCTGGGGGCTAACCAGAGGCATGCCTGGGCTGAGCTGAACCTTCTGGTGCACTGGCCCCTGGCTGACTGCTC     384

TTCTGCAGGAAGTTGGAGGAGATTCCTGAAGTTGATTCCTCAGGCTGGAGTTTCTGATGTCT     463

TTCTGTCTCCCCTCTCTTTCTTCTCCTACCAGGTCCACTTCTTTCAGAGGGGCCTGCGGTGCTCTAAAAGTTCTC     542

CTGTTAAAGTTTAGAGCAAATTGGTTATTATATTTTAAAATCAATAAAACTTTTAAAAGTACTAAGACAACTTCTAAGAGG     621

GGAGTGGACAGAGGGCCTGGTGGCAGCTCACAGTTTCTTTTCTGACCTTTGGTCTCACCCACCAAGTGTCCCACCTGAG     700

TGCCCACCTTGCCCACCTGAGGTAATGCCCTGGGGCTCCACCAGTCCAGATCCACAGGGCGCAGCCATGTGGGAGTGGC     779

GGCTGATTGTTACCCAGTAGTGTTGATAGCACATTATTCATAACAGCCAAGAGAGGAAGCAACCCAAATGTCCATTAG     858

CTGATAAATGGATAAATGAAATATGGTACGTCCGAAGAATGGAATATCATTCACCCTGAAAAAGAACGAAGTCCAGCA     937

CCAAAACGTGCTACAACATGGATGAACTTGTGCCACATGAAAGAAGAGGCCAGCCACAAAGGCCATAT    1016
```

FIG.6A

```
                            M   S   R   M   G   K   P   I   E   T   Q   K   P   P   P       16
ATTGTATGAAATGAA ATG TCC AGA ATG GGC AAA CCC ATA GAG ACA CAA AAA TCT CCG CCA CCT        1079

P   Y   S   R   L   S   P   R   D   E   Y   K   P   L   D   L   S   T                 36
CCC TAC TCT CGG CTG TCT CCT CGC GAC GAG TAC AAG CCA CTG GAT CTG TCC ACA               1139

L   S   Y   T   E   T   E   A   T   N   S   L   I   T   A   P   G   E   F   S         56
TTG TCT TAC ACT GAA ACG GAG GCT ACC AAC TCC CTC ATC ACT GCT CCG GGT GAA TTC TCA       1199

D   A   S   M   S   P   D   A   T   K   P   S   H   W   C   S   V   A   Y   W         76
GAC GCC AGC ATG TCT CCG GAC GCC ACC AAG CCG AGC CAC TGG TGC AGC GTG GCG TAC TGG       1259

E   H   R   T   R   V   G   R   L   Y   A   V   D   Q   A   V   S   I   F            96
GAG CAC CGG ACG CGC GTG GGC CGC CTC TAT GCG GTG TAC GAC CAG GCC GTC AGC ATC TTC       1319

Y   D   L   P   Q   G   S   G   F   C   L   G   Q   L   N   L   E   Q   R   S        116
TAC GAC CTA CCT CAG GGC AGC GGC TTC TGC CTG GGC CAG CTC AAC CTG GAG CAG CGC AGC       1379

E   S   V   R   R   T   S   K   I   G   E   H   P   I   F   V   N   S   K   E   P    136
GAG TCG GTG CGG CGA ACG AGC AAG ATC GGC GAG CAC CCC ATC TTC GTC AAC TCC AAG GAG CCC   1439

D   G   V   W   A   Y   N   R   G   E   H   P   I   F   V   N   S   P   T   L        156
GAC GGC GTG TGG GCC TAC AAC CGC GGC GAG CAC CAC CCC ATC TTC GTC CCG ACG CTG           1499

D   A   P   G   G   R   A   L   V   R   K   V   P   P   G   Y   S   I   K            176
GAC GCG CCC GGC GGC CGC GCC CTG GTC CGC AAG GTG CCC CCC GGC TAC TCC ATC AAG           1559
```

FIG.6B

```
  V   F   D   F   E   R   S   G   L   Q   H   A   P   E   P   D   A   A   D   G    196
GTG TTC GAC TTC GAG CGC TCG GGC CTG CAG CAC GCG CCC GAG CCC GAC GCC GCC GAC GGC    1619

P   Y   D   P   N   S   V   R   I   S   F   A   K   G   W   G   P   C   Y   S    216
CCC TAC GAC CCC AAC AGC GTC CGC ATC AGC TTC GCC AAG GGC TGG GGG CCC TGC TAC TCC    1679

R   Q   F   I   T   S   C   P   C   W   L   E   I   L   L   N   P   R   *         236
CGG CAG TTC ATC ACC TCC TGC CCC TGC TGG CTG GAG ATC CTC CTC AAC CCC AGA TAG        1739

TGGCGGCCCCGGCGAGGGCGGGTGGGAGGCCGGGCCACCTGCCGGCCTCGAGAGGGGCCGATGCCCAGA              1818

GACACAGCCCCCACGGACACAAACCCCCAGATATCATCTACCTAGATTAATATAAAGTTTATATATTATATGGAAAT      1897

ATATATTATACTTGTAATTATGGAGTCATTTTTACAATGTAATTATTTATGTATGGTGCAATGTGTGTATATGGACAAA    1976

ACAAGAAAGACGCACTTTGGCTTATAATTCTTTCAATACAGATATATTTCTTCCTCCTTCCTTACT                 2055

TTTATATATATATAAAGAAAATGATACAGAGCTAGGTGGAAAAGCCTGGGTTTGGTGTATGGTTTTTGAGATA          2134

TTAATGCCAGACAAAAGCTAATACCAGTCACTCGATAATAAAGTATTCGCATTATAGTTTTTTAAACTGTCTTCT        2213

TTTTACAAAGAGGGGCAGGTAGGGCTTCAGGGATTTCTGACCCATCSGTACCTTGAAACTTGACCTCAGTTTTCAAG      2292

TTTTACTTTTATTGGATAAAGACAGAACAAATTGAAAAGGGAGGAAAGTCACATTACTCTTAAGTAAACCAGAGAAAG     2371
```

FIG.6C

```
TTCTGTTGTTCCTTCCTGCCCATGGCTATGGGGTGTCCAGTGGATGGCGGTGGGGAAAAGGAGAATACACTGG    2450
CCATTTATCCTGGACAAGCTCTTCCAGTCTGATGGAGGAGGTTCATGCCCTAGCCTAGAAAGGCCCAGTCCATGACCC 2529
CCATCTTTGAGTTATGAGCAAGCTAAAAGAGAAGACACTATTTCTCACCATTTGTGGAAATGGCCTGGGGAACAAAGACT 2608
GAAATGGGCCTTGAGCCCACCTGCTACCTTGCAGAGAACCATCTCGAGCCCGTAGATCTTTTAGGACCTCCACAGGC    2687
TATTTCCCACCCCCCAGCCAAAAATAGCTCAGAATCTGCCCATCCAGGGCTGTATTAATGATTTATGTAAAGGCAGATG 2766
GTTTATTTCTACTTTGTAAAAGGGAAAAGTTGAGGTTCTGGAAGGATAAATGATTGCTCATGAGACAAATCAAGGTT    2845
AGAAGTTACATGGAATTGTAGGACCAGAGCCCATATCATTAGATCAGCTTTCTGAAGAATATTCTCMAAAAAGAAAGTC 2924
TCCTTGGCCAGATAACTAAGAGAGGAATGTTTCATTGTATATCTTTTTTCTTGGAGATTTATATTAACATATTAAGTGCTC 3003
TGAGAAGTCCTGTGTATTATCTCTTGCTGCATAATAAATTATCCCCAAACTTAAAAAAAAAAAAAAAAACTCGA    3082
G    3083
```

FIG.6D

PstI  StuI

```
ACGAGGACGACAGGCTGTGCGCGGTCTGCACGGCGCTCCGCGGCGGAGCTTCATGTGGGGCTGCGACCCGCGCAGCCGG  79

M      1
CCCCTCGCTGAGGGAACGGACCCCCGGTAACCGGAGACCGCCTTCCCCCCCACCCCTGGCGCCAAAGGATATCGT ATG  157

F   R   S   K   R   S   G   L   V   R   R   L   W   R   S   R   V   V   P   D    21
 TTC AGG TCC AAA CGC TCG GGG CTG GTG CGG CGA CTT TGG CGA AGT CGT GTG GTC CCC GAC  217

R   E   E   G   G   S   G   G   G   G   G   D   E   D   G   S   L   G   S        41
 CGG GAG GAA GGC GCC AGC GGC GGC GGC GGT GGC GGC GAC GAG GAT GGG AGC TTG GGC AGC  277

R   A   E   P   A   P   R   A   R   E   G   G   C   G   R   S   E   V   R        61
 CGA GCT GAG CCG GCC CCG CGG GCA AGA GAG GGC GGA GGC TGC GGC CGC TCC GAA GTC CGC  337

P   V   A   P   R   R   P   R   D   A   V   G   Q   R   G   A   Q   G   A   G    81
 CCG GTA GCC CCG CGG CGG CCC CGG GAC GCA GTG GGA CAG CGA GGC GCC CAG GGC CCG GGG  397

R   R   R   A   G   G   P   P   R   P   M   S   E   P   G   A   G   A   G       101
 AGG CGC CGG CGC GCA GGG GGC CCC CCG AGG CCC ATG TCG GAG CCA GGG GCC GGC GCT GGG  457

S   S   L   L   D   V   A   E   P   G   G   P   G   W   L   P   E   S   D   C   121
 AGC TCC CTG CTG GAC GTG GCG GAG CCG GGA GGC CCG GGC TGG CTG CCC GAG AGT GAC TGC  517

E   T   V   T   C   C   L   F   S   E   R   D   A   A   G   A   P   R   D   A   141
 GAG ACG GTG ACC TGC TGT CTC TTT TCG GAG CGG GAC GCC GCC GGC GCG CCC CGG GAC GCC  577

S   D   P   L   A   G   A   A   L   E   P   A   G   G   R   S   R   E   A       161
 AGC GAC CCC CTG GCC GGG GCG GCC CTG GAG CCG GCG GGC GGC GGG CGG AGT CGC GAA GCG  637

R   S   R   L   L   L   L   E   Q   E   L   K   T   V   T   Y   S   L   L   K   181
 CGC TCG CGG CTG CTG CTG CTG GAG CAG GAA CTC AAA ACC GTC ACG TAC TCG CTG CTG AAG  697

R   L   K   E   R   S   L   D   T   L   L   E   A   V   E   S   R   G   G   V   201
 CGG CTC AAG GAG CGC TCG CTG GAC ACG CTG CTG GAG GCG GTG GAG TCC CGC GGC GGC GTG  757

P   G   G   C   V   L   V   P   R   A   D   L   R   L   G   G   Q   P   A   P   221
 CCG GGC GGC TGC GTG CTG GTG CCG CGC GCC GAC CTC CGC CTG GGC GGC CAG CCC GCG CCG  817

P   Q   L   L   L   G   R   L   F   R   W   P   D   L   Q   H   A   V   E   L   241
 CCG CAG CTG CTG CTC GGC CGC CTC TTT CGC TGG CCC GAC CTG CAG CAC GCC GTG GAG CTG  877

K   P   L   C   G   C   H   S   F   A   A   A   A   D   G   P   T   V   C   C   261
 AAG CCC CTG TGC GGC TGC CAC AGC TTC GCC GCC GCC GCC GAC GGC CCT ACC GTG TGC TGC  937

N   P   Y   H   F   S   R   L   C   G   P   E   S   P   P   P   P   Y   S   R   281
 AAC CCC TAC CAC TTC AGC CGG CTC TGC GGG CCC GAA TCT CCG CCA CCT CCC TAC TCT CGG  997

L   S   P   R   D   E   Y   K   P   L   D   L   S   D   S   T   L   S   Y   T   301
 CTG TCT CCT CGC GAC GAG TAC AAG CCA CTG GAT CTG TCC GAT TCC ACA TTG TCT TAC ACT 1057
```

FIG.10A

```
  E    T    E    A    T    N    S    L    I    T    A    P    G    E    F    S    D    A    S    M   321
GAA  ACG  GAG  GCT  ACC  AAC  TCC  CTC  ATC  ACT  GCT  CCG  GGT  GAA  TTC  TCA  GAC  GCC  AGC  ATG  1117

S    P    D    A    T    K    P    S    H    W    C    S    V    A    Y    W    E    H    R    T   341
TCT  CCG  GAC  GCC  ACC  AAG  CCG  AGC  CAC  TGG  TGC  AGC  GTG  GCG  TAC  TGG  GAG  CAC  CGG  ACG  1177

R    V    G    R    L    Y    A    V    Y    D    Q    A    V    S    I    F    Y    D    L    P   361
CGC  GTG  GGC  CGC  CTC  TAT  GCG  GTG  TAC  GAC  CAG  GCC  GTC  AGC  ATC  TTC  TAC  GAC  CTA  CCT  1237

Q    G    S    G    F    C    L    G    Q    L    N    L    E    Q    R    S    E    S    V    R   381
CAG  GGC  AGC  GGC  TTC  TGC  CTG  GGC  CAG  CTC  AAC  CTG  GAG  CAG  CGC  AGC  GAG  TCG  GTG  CGG  1297

R    T    R    S    K    I    G    F    G    I    L    L    S    K    E    P    D    G    V    W   401
CGA  ACG  CGC  AGC  AAG  ATC  GGC  TTC  GGC  ATC  CTG  CTC  AGC  AAG  GAG  CCC  GAC  GGC  GTG  TGG  1357

A    Y    N    R    G    E    H    P    I    F    V    N    S    P    T    L    D    A    P    G   421
GCC  TAC  AAC  CGC  GGC  GAG  CAC  CCC  ATC  TTC  GTC  AAC  TCC  CCG  ACG  CTG  GAC  GCG  CCC  GGC  1417

G    R    A    L    V    V    R    K    V    P    P    G    Y    S    I    K    V    F    D    F   441
GGC  CGC  GCC  CTG  GTC  GTG  CGC  AAG  GTG  CCC  CCC  GGC  TAC  TCC  ATC  AAG  GTG  TTC  GAC  TTC  1477

E    R    S    G    L    Q    H    A    P    E    P    D    A    A    D    G    P    Y    D    P   461
GAG  CGC  TCG  GGC  CTG  CAG  CAC  GCG  CCC  GAG  CCC  GAC  GCC  GCC  GAC  GGC  CCC  TAC  GAC  CCC  1537

N    S    V    R    I    S    F    A    K    G    W    G    P    C    Y    S    R    Q    F    I   481
AAC  AGC  GTC  GCG  ATC  AGC  TTC  GCC  AAG  GGC  TGG  GGG  CCC  TGC  TAC  TCC  CGG  CAG  TTC  ATC  1597

T    S    C    P    C    W    L    E    I    L    L    N    N    P    R    *                       497
ACC  TCC  TGC  CCC  TGC  TGG  CTG  GAG  ATC  CTC  CTC  AAC  AAC  CCC  AGA  TAG                       1645

TGGCGGCCCCGGCGGGAGGGGCGGGTGGGAGGCCGCGGCCACCGCCACCTGCCGGCCTCGAGAGGGGCCGATGCCCAGA  1724

GACACAGCCCCCACGGACAAAACCCCCCAGATATCATCTACCTAGATTTAATATAAAGTTTTATATATTATATGGAAAA  1803

AAAAAAAAAAAAAA                                                                    1817
```

FIG.10B

COMPOSITIONS AND METHODS FOR THE TREATMENT AND DIAGNOSIS OF CARDIOVASCULAR DISEASE

CROSS-REFERENCE TO RELATED APPLICATIONS

This application is a continuation-in-part of application Ser. No. 08/870,434, filed Jun. 6, 1997, which is a continuation-in-part of co-pending application Ser. No. 08/799,910, filed Feb. 13, 1997, which claims priority benefit under 35 U.S.C. §119(e) of provisional Application Ser. No. 60/011,787, filed Feb. 16, 1996; and this application is a continuation-in-part of application Ser. No. 08/485,573, now U.S. Pat. No. 5,968,770 filed Jun. 7, 1995, which is a continuation-in-part of application Ser. No. 08/386,844, now U.S. Pat. No. 6,156,522 filed Feb. 10, 1995, each of which is incorporated herein by reference in its entirety.

1. INTRODUCTION

The present invention relates to methods and compositions for the treatment and diagnosis of cardiovascular disease, including, but not limited to, atherosclerosis, ischemia/reperfusion, hypertension, restenosis, arterial inflammation, and aortic and valvular calcification. The present invention further relates to screening methods to identify compositions and their therapeutic use for the treatment of fibro-proliferative and oncogenic disorders, including diabetic retinopathy, artherosclerosis, angiogenesis, inflammation, fibrosis, tumor growth and vascularization. Genes which are differentially expressed in cardiovascular or oncogenic disease states, relative to their expression in normal, or non-disease states are identified. Genes are also identified via the ability of their gene products to interact with other gene products involved in cardiovascular or oncogenic disease. The genes identified may be used diagnostically or as targets for therapeutic intervention. In this regard, the present invention provides methods for the identification and therapeutic use of compounds in the treatment and diagnosis of cardiovascular disease. Additionally, methods are provided for the diagnostic monitoring of patients undergoing clinical evaluation for the treatment of cardiovascular disease, for monitoring the efficacy of compounds in clinical trials, and for identifying subjects who may be predisposed to cardiovascular disease.

2. BACKGROUND OF THE INVENTION

Cardiovascular disease is a major health risk throughout the industrialized world. Atherosclerosis, the most prevalent of cardiovascular diseases, is the principal cause of heart attack, stroke, and gangrene of the extremities, and thereby the principal cause of death in the, United States. Atherosclerosis is a complex disease involving many cell types and molecular factors (for a detailed review, see Ross, 1993, Nature 362: 801–809). The process, in normal circumstances a protective response to insults to the endothelium and smooth muscle cells (SMCs) of the wall of the artery, consists of the formation of fibrofatty and fibrous lesions or plaques, preceded and accompanied by inflammation. The advanced lesions of atherosclerosis may occlude the artery concerned, and result from an excessive inflammatory-fibroproliferative response to numerous different forms of insult. For example, shear stresses are thought to be responsible for the frequent occurrence of atherosclerotic plaques in regions of the circulatory system where turbulent blood flow occurs, such as branch points and irregular structures.

The first observable event in the formation of an atherosclerotic plaque occurs when blood-borne monocytes adhere to the vascular endothelial layer and transmigrate through to the sub-endothelial space. Adjacent endothelial cells at the same time produce oxidized low density lipoprotein (LDL). These oxidized LDL's are then taken up in large amounts by the monocytes through scavenger receptors expressed on their surfaces. In contrast to the regulated pathway by which native LDL (nLDL) is taken up by nLDL specific receptors, the scavenger pathway of uptake is not regulated by the monocytes.

These lipid-filled monocytes are called foam cells, and are the major constituent of the fatty streak. Interactions between foam cells and the endothelial and SMCs which surround them lead to a state of chronic local inflammation which can eventually lead to smooth muscle cell proliferation and migration, and the formation of a fibrous plaque. Such plaques occlude the blood vessel concerned and thus restrict the flow of blood, resulting in ischemia.

Ischemia is a condition characterized by a lack of oxygen supply in tissues of organs due to inadequate perfusion. Such inadequate perfusion can have number of natural causes, including atherosclerotic or restenotic lesions, anemia, or stroke, to name a few. Many medical interventions, such as the interruption of the flow of blood during bypass surgery, for example, also lead to ischemia. In addition to sometimes being caused by diseased cardiovascular tissue, ischemia may sometimes affect cardiovascular tissue, such as in ischemic heart disease. Ischemia may occur in any organ, however, that is suffering a lack of oxygen supply.

The most common cause of ischemia in the heart is atherosclerotic disease of epicardial, coronary arteries. By reducing the lumen of these vessels, atherosclerosis causes an absolute decrease in myocardial perfusion in the basal state or limits appropriate increases in perfusion when the demand for flow is augmented. Coronary blood flow can also be limited by arterial thrombi, spasm, and, rarely, coronary emboli, as well as by ostial narrowing due to luetic aortitis. Congenital abnormalities, such as anomalous origin of the left anterior descending coronary artery from the pulmonary artery, may cause myocardial ischemia and infarction in infancy, but this cause is very rare in adults. Myocardial ischemia can also occur if myocardial oxygen demands are abnormally increased, as in severe ventricular hypertrophy due to hypertension or aortic stenosis. The latter can be present with angina that is indistinguishable from that caused by coronary atherosclerosis. A reduction in the oxygen-carrying capacity of the blood, as in extremely severe anemia or in the presence of carboxy-hemoglobin, is a rare cause of myocardial ischemia. Not infrequently, two or more causes of ischemia will coexist, such as an increase in oxygen demand due to left ventricular hypertrophy and a reduction in oxygen supply secondary to coronary atherosclerosis.

The principal surgical approaches to the treatment of ischemic atherosclerosis are bypass grafting, endarterectomy, and percutaneous translumenal angioplasty (PCTA). The failure rate after these approaches due to restenosis, in which the occlusions recur and often become even worse, is extraordinarily high (30–50%). It appears that much of the restenosis is due to further inflammation, smooth muscle accumulation, and thrombosis.

A modified balloon angioplasty approach was used to treat arterial restenosis in pigs by gene therapy (Ohno et al., 1994, Science 265: 781–784). A specialized catheter was used to introduce a recombinant adenovirus carrying the gene encoding thymidine kinase (tk) into the cells at the site of arterial blockage. Subsequently, the pigs were treated with ganciclovir, a nucleoside analog which is converted by tk into a toxic form which kills cells when incorporated into DNA. Treated animals had a 50% to 90% reduction in arterial wall thickening without any observed local or systemic toxicities.

Because of the presumed role of the excessive inflamnmatory-fibroproliferativeresponse in atherosclerosis and ischemia, a number of researchers have investigated, in the context of arterial injury, the expression of certain factors involved in inflammation, cell recruitment and proliferation. These factors include growth factors, cytokines, and other chemicals, including lipids involved in cell recruitment and migration, cell proliferation and the control of lipid and protein synthesis.

For example, the expression of PDGF (platelet derived growth factor) or its receptor was studied: in rats during repair of arterial injury (Majesky et al., 1990, J. Cell Biol. 111: 2149); in adherent cultures of human monocyte-derived macrophages treated with oxidized LDL (Malden et al., 1991, J. Biol. Chem. 266: 13901); and in bovine aortic endothelial cells subjected to fluid shear stress (Resnick et al., 1993, Proc. Natl. Acad. Sci. USA 90:4591–4595). Expression of IGF-I (insulin-like growth factor-I) was studied after balloon deendothelialization of rat aorta (Cercek et al., 1990, Circulation Research 66: 1755–1760).

Other studies have focused on the expression of adhesion-molecules on the surface of activated endothelial cells which mediate monocyte adhesion. These adhesion molecules include intracellular adhesion molecule-1, ICAM-1 (Simmons et al., 1988, Nature, 331: 624–627), ELAM (Bevilacqua et al., 1989, Science 243: 1160–1165; Bevilacqua et al., 1991, Cell 67: 233), and vascular cell adhesion molecule, VCAM-1 (Osborn et al., 1989, Cell 59: 1203–35 1211); all of these surface molecules are induced transcriptionally in the presence of IL-1. Histological studies reveal that ICAM-1, ELAM and VCAM-1 are expressed on endothelial cells in areas of lesion formation in vivo (Cybulsky et al., 1991, Science 251: 788–791; 1991, Arterioscler. Thromb. 11: 1397a; Poston et al., 1992, Am. J. Pathol. 140: 665–673). VCAM-1 and ICAM-1 were shown to be induced in cultured rabbit arterial endothelium, as well as in cultured human iliac artery endothelial cells by lysophophatidylcholine, a major phospholipid component of atherogenic lipoproteins. (Kume et al., 1992, J. Clin. Invest. 90: 1138–1144). VCAM-I, ICAM-1, and class II major histocompatibility antigens were reported to be induced in response to injury to rabbit aorta (Tanaka, et al., 1993, Circulation 88: 1788–1803).

Cytomegalovirus (CMV) has been implicated in restenosis as well as atherosclerosis in general (Speir, et al., 1994, Science 265: 391–394). It was observed that the CMV protein IE84 apparently predisposes smooth muscle cells to increased growth at the site of restenosis by combining with and inactivating p53 protein, which is known to suppress tumors in its active form.

Cardiac valve calcification often results in obstruction of blood flow, which eventually leads to valve replacement. The molecular mechanisms resulting in valve calcification are unknown. Collagen and specific bone matrix proteins are thought to provide the framework for ectopic tissue calcification (Mohler E R 3rd, Adam L P, McClelland P, Graham L, Hathaway D R, Arterioscler. Thromb. Vasc. Biol. 1997, 17(3):547–52). Mohler et al. showed that osteopontin is present in calcified human aortic valves which suggests that osteopontin is a regulatory protein in pathological calcification.

Calcific aortic valve stenosis constitutes a significant health problem in the elderly. Only a minority of those with potentially operable aortic valve stenosis undergo surgery (Lindroos M, Kupari M, Heikkila J, Tilvis R, Lindroos M, Kupari M, Heikkila J, Tilvis R J, Am. Coll. Cardiol. 1993, 21(5):1220–5). In a study to determine whether mitral annular calcification and aortic valve calcification, with or without stenosis, are expressions of atherosclerotic disease, Boon et al. noted that individuals with mitral annular calcification and stenotic or non-stenotic aortic valve calcification have a high incidence of atherosclerotic risk factors, suggesting they should be considered as manifestations of generalised atherosclerosis (Boon A, Cheriex E, Lodder J, Kessels F, Heart 1997, 78(5):472–4). In another study aimed at identifying factors influencing aortic valve calcification in old age, Lindroos et al. noted that gender, smoking, diabetes, serum lipids and insulin were unrelated to valvular calcification. Their data suggested that leanness and a history of hypertension increase the likelihood of senile aortic valve calcification, and that calcium metabolism may also be of significance (Lindroos M, Kupari M, Valvanne J, Strandberg T, Heikkila J, Tilvis R, Eur. Heart J. 1994, 15(7):865–70).

The foregoing studies are aimed at defining the role of particular gene products presumed to be involved in the excessive inflammatory-fibroproliferative response leading to atherosclerotic plaque formation. However, such approaches cannot identify the full panoply of gene products that are involved in the disease process, much less identify those which may serve as therapeutic targets for the diagnosis and treatment of various forms of cardiovascular disease.

3. SUMMARY OF THE INVENTION

The present invention relates to methods and compositions for the treatment and diagnosis of cardiovascular disease, including but not limited to, atherosclerosis, ischemia/reperfusion, hypertension, restenosis, and arterial inflammation. Specifically, genes are identified and described which are differentially expressed in cardiovascular disease states, relative to their expression in normal, or non-cardiovascular disease states.

The present invention further relates to screening methods to identify compositions and their therapeutic use for the treatment of fibroproliferative and oncogenic disorders, including diabetic retinopathy, cancer, tumorigenesis, vascularization of tumors, angiogenesis artherosclerosis inflammation and fibrosis.

"Differential expression", as used herein, refers to both quantitative as well as qualitative differences in the genes' temporal and/or tissue expression patterns. Differentially expressed genes may represent "fingerprint genes," and/or "target genes." "Fingerprint gene," as used herein, refers to a differentially expressed gene whose expression pattern may be utilized as part of a prognostic or diagnostic cardiovascular disease evaluation, or which, alternatively, may be used in methods for identifying compounds useful for the treatment of cardiovascular disease. "Target gene", as used herein, refers to a differentially expressed gene involved in cardiovascular disease such that modulation of the level of target gene expression or of target gene product activity may act to ameliorate a cardiovascular disease condition. Compounds that modulate target gene expression or activity of the target gene product can be used in the treatment of cardiovascular disease.

Further, "pathway genes" are defined via the ability of their products to interact with other gene products involved in cardiovascular disease. Pathway genes may also exhibit target gene and/or fingerprint gene characteristics. Although the genes described herein may be differentially expressed with respect to cardiovascular disease, and/or their products may interact with gene products important to cardiovascular disease, the genes may also be involved in mechanisms important to additional cardiovascular processes.

The invention includes the products of such fingerprint, target, and pathway genes, as well as antibodies to such gene products. Furthermore, the engineering and use of cell- and animal-based models of cardiovascular disease to which such gene products may contribute are also described.

The present invention encompasses methods for prognostic and diagnostic evaluation of cardiovascular disease conditions, and for the identification of subjects exhibiting a predisposition to such conditions. Furthermore, the invention provides methods for evaluating the efficacy of drugs, and monitoring the progress of patients, involved in clinical trials for the treatment of cardiovascular disease.

The invention also provides methods for the identification of compounds that modulate the expression of genes or the activity of gene products involved in cardiovascular disease, as well as methods for the treatment of cardiovascular disease which may involve the administration of such compounds to individuals exhibiting cardiovascular disease symptoms or tendencies.

The invention also provides methods for the identification of compounds that modulate the expression of genes or the activity of gene products involved in fibroproliferative or oncogenic disorders, including tumorigenesis and the vascularization of tumors.

The invention is based, in part, on systematic search strategies involving in vivo and in vitro cardiovascular disease paradigms coupled with sensitive and high throughput gene expression assays. In contrast to approaches that merely evaluate the expression of a given gene product presumed to play a role in a disease process, the search strategies and assays used herein permit the identification of all genes, whether known or novel, that are expressed or repressed in the disease condition, as well as the evaluation of their temporal regulation and function during disease progression. This comprehensive approach and evaluation permits the discovery of novel genes and gene products, as well as the identification of an array of genes and gene products (whether novel or known) involved in novel pathways that play a major role in the disease pathology. Thus, the invention allows one to define targets useful for diagnosis, monitoring, rational drug screening and design, and/or other therapeutic intervention.

In the working examples described herein, five novel human genes are identified that are demonstrated to be differentially expressed in different cardiovascular disease states. The identification of these genes and the characterization of their expression in particular disease states provide newly identified roles in cardiovascular disease for these genes.

Specifically, fchd53 1, fchd540, and fchd545 are novel genes that are each differentially regulated in endothelial cells subjected to shear stress. fchd531 and fchd545 are each down-regulated, whereas fchd540 is up-regulated by shear stress. fchd602 and fchd605 are novel genes that are each up-regulated in monocytes treated with oxidized LDL. Accordingly, methods are provided for the diagnosis, monitoring in clinical trials, screening for therapeutically effective compounds, and treatment of cardiovascular disease based upon the discoveries herein regarding the expression patterns of fchd53 1, fchd540, fchd545, fchd602, and fchd605.

Both fchd540 and rchd534 are up-regulated in response to laminar shear stress and are specifically expressed in vascular tissue. These findings combined with the observations that both fchd540 and rchd534 specifically inhibit TGF-β signalling and that these genes are located in an area of the human genome implicated in the pathogenesis of several human malignancies indicates that they are excellent and specific targets for therapeutic intervention in the treatment of fibroproliferative and oncogenic disorders including tumorigenesis and vascularization.

The characteristic up-regulation of genes fchd540, fchd602, and fchd605 can be used to design cardiovascular disease treatment strategies. For those up-regulated genes that have a causative effect on the disease conditions, treatment methods can be designed to reduce or eliminate their expression, particularly in endothelial cells or monocytes. Alternatively, treatment methods include inhibiting the activity of the protein products of these genes. For those up-regulated genes that have a protective effect, treatment methods can be designed for enhancing the activity of the products of such genes.

In either situation, detecting expression of these genes in excess of normal expression provides for the diagnosis of cardiovascular disease. Furthermore, in testing the efficacy of compounds during clinical trials, a decrease in the level of the expression of these genes corresponds to a return from a disease condition to a normal state, and thereby indicates a positive effect of the compound. The cardiovascular diseases that may be so diagnosed, monitored in clinical trials, and treated include but are not limited to atherosclerosis, ischemia/reperfusion, hypertension, restenosis, and arterial inflammation.

The characteristic down-regulation of fchd531 and fchd545 can also be used to design cardiovascular disease treatment strategies. For those genes whose down-regulation has a pathogenic effect, treatment methods can be designed to restore or increase their expression, particularly in endothelial cells. Alternatively, treatment methods include increasing the activity of the protein products of these genes. For those genes whose down-regulation has a protective effect, treatment methods can be designed for decreasing the amount or activity of the products of such genes.

In either situation, detecting expression of these genes in below normal expression provides for the diagnosis of cardiovascular disease. Furthermore, in testing the efficacy of compounds during clinical trials, an increase in the level of the expression of these genes corresponds to a return from a disease condition to a normal state, and thereby indicates a positive effect of the compound. The cardiovascular diseases that may be so diagnosed, monitored in clinical trials, and treated include but are not limited to atherosclerosis, ischemia/reperfusion, hypertension, restenosis, and arterial inflammation.

The invention encompasses methods for screening compounds and other substances for treating cardiovascular disease by assaying their ability to modulate the expression of the target genes disclosed herein or activity of the protein products of the target genes. The invention further encompasses methods for screening compounds and other substances for treating fibroproliferative disorders and oncogenic disorders by assaying their ability to modulate the expression of the target genes disclosed herein or activity of the protein products of the target genes. Such screening methods include, but are not limited to, assays for identifying compounds and other substances that interact with (e.g., bind to) the target gene protein products.

In addition, the invention encompasses methods for treating cardiovascular disease by administering compounds and other substances that modulate the overall activity of the target gene products. Compounds and other substances can effect such modulation either on the level of target gene expression or target protein activity.

The invention is based in part on the identification of novel protein-protein interactions of the rchd534 protein with itself and with the fchd540 protein, as well as interactions of the rchd534 protein or the fchd540 protein with other protein members of the TGF-$\beta$ signalling pathway. The rchd534 gene was described in Applicant's co-pending application Ser. No. 08/485,573, filed Jun. 7, 1995, which is hereby incorporated by reference in its entirety. Screening methods are provided for identifying compounds and other substances for treating cardiovascular disease by assaying their ability to inhibit these interactions. Furthermore, methods are provided for identifying compounds and other substances that enhance the TGF-$\beta$ response by modulating the activity of the expression of the rchd534 or fchd540 genes or the activity of their gene products. In addition, methods are provided for treating cardiovascular disease by administering compounds and other substances that inhibit these protein interactions.

The invention is based in part on the identification of the endothelial cell specific expression pattern of two genes, rchd534 and fchd540, whose protein products inhibit the TGF-$\beta$ response. The fchd540 gene has been mapped to regions of the human genome that have been implicated in the pathogenesis of several human malignancies. The invention is further based on the finding that these genes and mutants thereof may be used to modulate TGF-$\beta$ induced signalling in endothelial cells. Accordingly, the rchd534 and rchd540 genes may be targets for intervention in a variety of inflammatory and fibroproliferative disorders that involve endothelial cells, including, but not limited to, oncology related disorders, disorders related to vascularization, such as cancer angiogenesis, inflammation, and fibrosis.

Membrane bound target gene products containing extracellular domains can be a particularly useful target for treatment methods as well as diagnostic and clinical monitoring methods. The fchd602 gene, for example, encodes a transmembrane protein, which contains multiple transmembrane domains and, therefore, can be readily contacted by other compounds on the cell surface. Accordingly, natural ligands, derivatives of natural ligands, and antibodies that bind to the fchd602 gene product can be utilized to inhibit its activity, or alternatively, to target the specific destruction of cells that express the gene. Furthermore, the extracellular domains of the fchd602 gene product provide targets which allow for the design of especially efficient screening systems for identifying compounds that bind to the fchd602 gene product.

Such an assay system can also be used to screen and identify antagonists of the interaction between the fchd602 gene product and ligands that bind to the fchd602 gene product. For example, the compounds can act as decoys by binding to the endogenous (i.e., natural) ligand for the fchd602 gene product. The resulting reduction in the amount of ligand-bound fchd602 gene transmembrane protein will modulate the activity of disease state cells, such as monocytes. Soluble proteins or peptides, such as peptides comprising one or more of the extracellular domains, or portions and/or analogs thereof of the fchd602 gene product, including, for example, soluble fusion proteins such as Ig-tailed fusion proteins, can be particularly useful for this purpose.

Similarly, antibodies that are specific to one or more of the extracellular domains of the fchd602 product provide for the ready detection of this target gene product in diagnostic tests or in clinical test monitoring. Accordingly, endothelial cells can be treated, either in vivo or in vitro, with such a labeled antibody to determine the disease state of endothelial cells. Because the fchd602 gene product is up-regulated in monocytes in the disease state, its detection positively corresponds with cardiovascular disease.

Such methods for treatment, diagnosis, and clinical test monitoring which use the fchd602 gene product as described above can also be applied to other target genes that encode transmembrane gene products, including but not limited to the fchd545 gene, which encodes multiple transmembrane domains and extracellular domains.

The invention is further based in part on the generation and phenotypic characterization of transgenic knockout homozygous rchd534 mutant mice. Such homozygous rchd534 mutant mice display characteristic cardiovascular disease symptoms, wherein said characteristic cardiovascular disease symptom is hyperplasia and/or thickening of at least one cardiac valve, cardiac outflow tract development defects, cardiac calcification, including but not limited to, aortic and valvular calcification, epicardial and/or endocardial vascular malformations, or defects in the regulation of vascular tone. Such homozygous rchd534 mutant mice serve as useful models for the analysis and characterization of rchd534 protein involvement in development and homeostasis of the cardiovascular system and tissue-specific regulation of the TGF-$\beta$ signaling pathways.

Such homozygous rchd534 mutant mice are additionally useful as animal models for studying human diseases and syndromes including, without limitation, vascular malformations attributable to hereditary Hemorrhagic Telangiectasia, advanced athersclerosis and/or plaque rupture, cardiovascular calcification, including but not limited to, aortic and valvular calcification, allo/xenograft valvular calcifications, sclero-calcific aortic valve disease, calcific aortic valve stenosis, mitral annular calcification, stenotic or non-stenotic aortic valve calcification, and senile aortic valve calcification.

The present invention further relates to methods for the generation of such homozygous rchd534 mutant mice. Disclosed herein are materials and methods for inactivating ("knocking out") the rchd534 gene in mammalian cells and embryos. Included are nucleic acid constructs useful for inactivating the rchd534 gene in a mammalian target cell. The present invention also includes methods for generating a mammalian totipotent cell having at least one inactivated (non-functional) rchd534 allele, where the totipotent cell is derived from a mammalian species in which alleles for the rchd534 gene normally are present and functional. A "functional" allele is capable of being transcribed and translated to produce a polypeptide having an activity the same as or substantially similar to the rchd534. The methods include providing a plurality of cells characterized as totipotent cells of various mammalian species, introducing into the totipotent cells a nucleic acid construct effective for inactivating the rchd534 gene by insertion of a desired DNA sequence into an insertion site of the gene through homologous recombination, and then identifying a totipotent cell having at least one inactivated rchd534 allele.

The invention encompasses methods for screening compounds and other substances for treating cardiovascular disease symptoms, including but not limited to, hyperplasia and/or thickening of at least one cardiac valve, cardiac outflow tract development defects, cardiac calcification (e.g., including but not limited to, aortic and valvular calcification), epicardial and/or endocardial vascular malformations, or defects in the regulation of vascular tone, by assaying the ability of such compounds and other substances to modulate the expression of the rchd534 gene disclosed herein or activity of the protein products of the rchd534 genes. The invention further encompasses methods for screening compounds and other substances for treating human diseases and syndromes including, without limitation, vascular malformations attributable to hereditary Hemorrhagic Telangiectasia, advanced atherosclerosis and/or plaque rupture, cardiovascular calcification, including but not limited to, aortic and valvular calcification, allo/xenograft valvular calcifications, and sclero-calcific aortic valve disease, by assaying the ability of such compounds and other substances to modulate the expression of the target genes disclosed herein or activity of the protein products of the target genes. Such screening methods include, but are not limited to, assays for identifying compounds and other substances that interact with (e.g., bind to) the rchd534 gene protein product.

The examples presented in Sections 6 and 7, below, demonstrate the use of the cardiovascular disease paradigms of the invention to identify cardiovascular disease target genes.

The example presented in Section 8, below, demonstrates the use of fingerprint genes in diagnostics and as surrogate markers for testing the efficacy of candidate drugs in basic research and in clinical trials.

The example presented in Section 9, below, demonstrates the use of fingerprint genes, particularly fchd545, in the imaging of a diseased cardiovascular tissue.

The example presented in Section 11, below, demonstrates the interaction of two target gene products, the rchd534 and fchd540 proteins, and the further characterization of their roles in oncology, angiogenesis, cardiovascular disease and the TGF-β signalling pathway.

The example presented in section 13, below, demonstrates the generation and phenotypic characterization of transgenic knockout homozygous rchd534 mutant mice which are useful models for the analysis and characterization of rchd534 protein involvement in development and homeostasis of the cardiovascular system and tissue-specific regulation of the add TGF-β signaling pathways.

4. DESCRIPTION OF THE FIGURES

FIGS. 1A–1D. Nucleotide sequence and encoded amino acid sequence of the fchd531 gene.

FIGS. 2A–2E. Nucleotide sequence and encoded amino acid sequence of the fchd540 gene.

FIGS. 3A–3C. Nucleotide sequence and encoded amino acid sequence of the fchd545 gene.

FIGS. 4A–4B. Nucleotide sequence and encoded amino acid sequence from the fchd602 gene.

FIGS. 5A–5B. Nucleotide sequence and encoded amino acid sequence from the fchd605 gene.

FIGS. 6A–6D. Nucleotide sequence and encoded amino acid sequence of the rchd534 gene.

FIG. 7A–D. Generation of rchd534mutant mice. (A) Targeted disruption of the rchd534 locus. The location of the flanking probe is indicated. (B) The predicted genome structure of three targeted ES cell clones (182, 338, 343), identified by Southern blot hybridization of EcoRI-digested DNA (not shown) with the indicated probe, was verified with additional digestions. c denotes wild type ES cell DNA. (C) Genotyping by Southern blot of tail DNA (EcoRI digest, flanking probe). +/+ indicates wild-type, +/– indicates heterozygous, –/– indicates homozygous mutant. (D) Expression of rchd534-LacZ fusion transcript. (top) Diagram of rchd534 and rchd534LacZ fusion transcripts. Probes used for northern analysis are indicated. The dark rectangle indicates the targeted MH2-encoding exon. (bottom) Nothem blot analysis of RNA prepared from lungs. A wild-type rchd534 transcript of approximately 2.7 kb was detected with 5' or 3' probes. The 2.7 kb message was detected at a reduced level in the +/– sample, and was absent in the –/– sample. The 5' probe hybridized to an additional 5.5 kb transcript in the +/– and –/– samples. To confirm that this 5.5 kb transcript was the expected rchd534-LacZ fusion, the blot was rehybridized with a LacZ probe.

Figure 8:
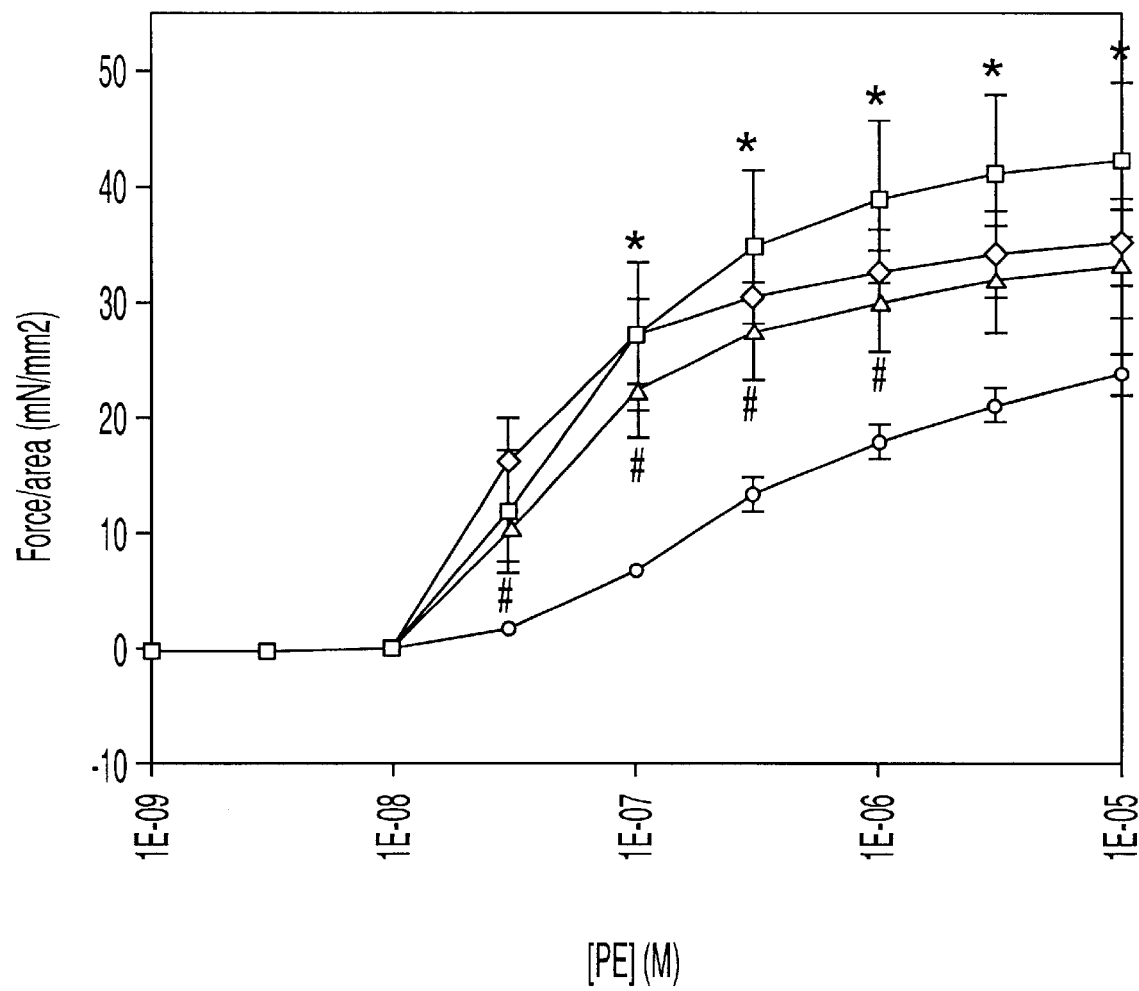

FIG. 8. Contractile responses of aortic ring preparations to the vasoconstrictor phenylephrine. (1) Forces measured in response to each PE dose and normalized for aortic ring area (means +/–SEM, n=7 or 8; (○), intact wild-type rings; (Δ), de-endothelialized wild-type rings; (□), intact mutant rings; (◊), de-endothelialized mutant rings). Symbols indicate that the intact mutant value (*) or the de-endothelialized wild-type value (#) is significantly different from the intact wild-type value ($p<0.05$). (2) Mean arterial blood pressure in wild-type (+/+) and rchd534 homozygous mutant mice. Error bars indicate S.E.M. The difference is statistically significant ($p <0.05$).

Figure 9:
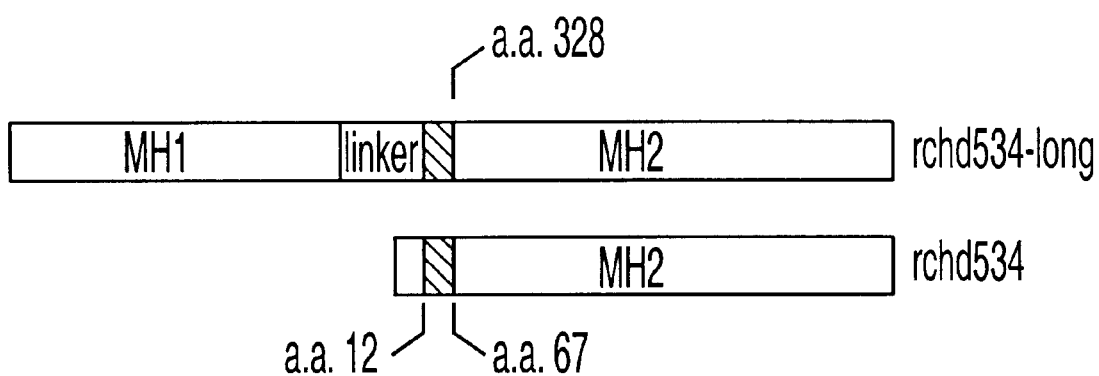

FIG. 9. Schematic comparison of the rchd534 protein and the rchd534-long protein.

FIGS. 10A–B. DNA (SEQ ID NO:45) and encoded amino acid sequence (SEQ ID NO:46) of the rchd534-long cDNA encoding the rchd534-long protein.

5. DETAILED DESCRIPTION OF THE INVENTION

Methods and compositions for the diagnosis and treatment of cardiovascular disease, including but not limited to atherosclerosis, ischemia/reperfusion, hypertension, restenosis, and arterial inflammation, are described. Methods and compositions for the treatment of oncogenic related disorders, including tumorigenesis and the vascularization of tumors, are also described. The invention is based, in part, on the evaluation of the expression and role of all genes that are differentially expressed in paradigms that are physiologically relevant to the disease condition. This permits the definition of disease pathways and the identification of targets in the pathway that are useful both diagnostically and therapeutically.

Genes, termed "target genes" and/or "fingerprint genes" which are differentially expressed in cardiovascular disease conditions, relative to their expression in normal, or non-cardiovascular disease conditions, are described in Section 5.4. Additionally, genes, termed "pathway genes" whose gene products exhibit an ability to interact with gene products involved in cardiovascular disease are also described in Section 5.4. Pathway genes may additionally have fingerprint and/or target gene characteristics. Methods for the identification of such fingerprint, target, and pathway genes are described in Sections 5.1, 5.2, and 5.3.

Further, the gene products of such fingerprint, target, and pathway genes are described in Section 5.4.2, antibodies to such gene products are described in Section 5.4.3, as are cell- and animal-based models of cardiovascular disease and oncogenic related disorders to which such gene products may contribute, in Section 5.4.4.

Methods for the identification of compounds which modulate the expression of genes or the activity of gene products involved in cardiovascular disease and fibroproliferative and oncogenic related disorders including tumorigenesis are described in Section 5.5. Methods for monitoring the efficacy of compounds during clinical trials are described in Section 5.5.4. Additionally described below, in Section 5.6, are methods for the treatment of cardiovascular disease and oncogenic related disorders.

Also discussed below, in Section 5.8, are methods for prognostic and diagnostic evaluation of cardiovascular disease, including the identification of subjects exhibiting a predisposition to this disease, and the imaging of cardiovascular disease conditions.

5.1. Identification of Differentially Expressed Genes

This section describes methods for the identification of genes which are involved in cardiovascular disease, including but not limited to atherosclerosis, ischemia/reperfusion, hypertension, restenosis, and arterial inflammation. Such genes may represent genes which are differentially expressed in cardiovascular disease conditions relative to their expression in normal, or non-cardiovascular disease conditions. Such differentially expressed genes may represent "target" and/or "fingerprint" genes. Methods for the identification of such differentially expressed genes are described, below, in this section. Methods for the further characterization of such differentially expressed genes, and for their identification as target and/or fingerprint genes, are presented, below, in Section 5.3.

"Differential expression" as used herein refers to both quantitative as well as qualitative differences in the genes' temporal and/or tissue expression patterns. Thus, a differentially expressed gene may have its expression activated or completely inactivated in normal versus cardiovascular disease conditions (ea., treated with oxidized LDL versus untreated), or under control versus experimental conditions. Such a qualitatively regulated gene will exhibit an expression pattern within a given tissue or cell type which is detectable in either control or cardiovascular disease subjects, but is not detectable in both. Alternatively, such a qualitatively regulated gene will exhibit an expression pattern within a given tissue or cell type which is detectable in either control or experimental subjects, but is not detectable in both. "Detectable", as used herein, refers to an RNA expression pattern which is detectable via the standard techniques of differential display, reverse transcriptase-(RT-) PCR and/or Northern analyses, which are well known to those of skill in the art.

Alternatively, a differentially expressed gene may have its expression modulated, quantitatively increased or decreased, in normal versus cardiovascular disease states, or under control versus experimental conditions. The degree to which expression differs in normal versus cardiovascular disease or control versus experimental states need only be large enough to be visualized via standard characterization techniques, such as, for example, the differential display technique described below. Other such standard characterization techniques by which expression differences may be visualized include but are not limited to quantitative RT-PCR and Northern analyses.

Differentially expressed genes may be further described as target genes and/or fingerprint genes. "Fingerprint gene," as used herein, refers to a differentially expressed gene whose expression pattern may be utilized as part of a prognostic or diagnostic cardiovascular disease evaluation, or which, alternatively, may be used in methods for identifying compounds useful for the treatment of cardiovascular disease. A fingerprint gene may also have the characteristics of a target gene.

"Target gene", as used herein, refers to a differentially expressed gene involved in cardiovascular disease in a manner by which modulation of the level of target gene expression or of target gene product activity may act to ameliorate symptoms of cardiovascular disease. A target gene may also have the characteristics of a fingerprint gene.

A variety of methods may be utilized for the identification of genes which are involved in cardiovascular disease. These methods include but are not limited to the experimental paradigms described, below, in Section 5.1.1. Material from the paradigms may be characterized for the presence of differentially expressed gene sequences as discussed, below, Bin Section 5.1.2.

5.1.1. Paradigms for the Identification of Differentially Expressed Genes

One strategy for identifying genes that are involved in cardiovascular disease is to detect genes that are expressed differentially under conditions associated with the disease versus non-disease conditions. The sub-sections below describe a number of experimental systems, called paradigms, which may be used to detect such differentially expressed genes. In general, the paradigms include at least one experimental condition in which subjects or samples are treated in a manner associated with cardiovascular disease, in addition to at least one experimental control condition lacking such disease associated treatment. Differentially expressed genes are detected, as described herein, below, by comparing the pattern of gene expression between the experimental and control conditions.

Once a particular gene has been identified through the use of one such paradigm, its expression pattern may be further characterized by studying its expression in a different paradigm. A gene may, for example, be regulated one way in a given paradigm (e.g., up-regulation), but may be regulated differently in some other paradigm (e.g., down-regulation). Furthermore, while different genes may have similar expression patterns in one paradigm, their respective expression patterns may differ from one another under a different paradigm. Such use of multiple paradigms may be useful in distinguishing the roles and relative importance of particular genes in cardiovascular disease.

5.1.1.1. Foam Cell Paradigmy-1

Among the paradigms which may be utilized for the identification of differentially expressed genes involved in atherosclerosis, for example, are paradigms designed to analyze those genes which may be involved in foam cell formation. Such paradigms may serve to identify genes involved in the differentiation of this cell type, or their uptake of oxidized LDL.

One embodiment of such a paradigm, hereinafter referred to as Paradigm A, is carried out as follows: First, human blood is drawn and peripheral monocytes are isolated by methods routinely practiced in the art. These human monocytes can then be used immediately or cultured in vitro, using methods routinely practiced in the art, for 5 to 9 days where they develop more macrophage-like characteristics such as the up-regulation of scavenger receptors. These cells are then treated for various lengths of time with agents thought to be involved in foam cell formation. These agents include but are not limited to oxidized LDL, acetylated LDL, lysophosphatidylcholine, and homocysteine. Control monocytes that are untreated or treated with native LDL are grown in parallel. At a certain time after addition of the test agents, the cells are harvested and analyzed for differential expression as described in detail in Section 5.1.2., below. The Example presented in Section 6, below, demonstrates in detail the use of such a foam cell paradigm to identify genes which are differentially expressed in treated versus control cells.

5.1.1.2. Foam Cell Paradigm-2

Alternative paradigms involving monocytes for detecting differentially expressed genes associated with atherosclerosis involve the simulation of the phenomenon of transmigration. When monocytes encounter arterial injury, they adhere to the vascular endothelial layer, transmigrate across this layer, and locate between the endothelium and the layer of smooth muscle cells that ring the artery. This phenomenon can be mimicked in vitro by culturing a layer of endothelial cells isolated, for example, from human umbilical cord. Once the endothelial monolayer forms, monocytes drawn from peripheral blood are cultured on top of the endothelium in the presence and absence of LDL. After several hours, the monocytes transmigrate through the endothelium and develop into foam cells after 3 to 5 days when exposed to LDL. In this system, as in vivo, the endothelial cells carry out the oxidation of LDL which is then taken up by the monocytes. As described in sub-section 5.1.2. below, the pattern of gene expression can then be compared between these foam cells and untreated monocytes.

5.1.1.3. Foam Cell Paradigm-3

Yet another system includes the third cell type, smooth muscle cell, that plays a critical role in atherogenesis (Navab et al., 1988, J. Clin. Invest., 82: 1853). In this system, a multilayer of human aortic smooth muscle cells was grown on a micropore filter covered with a gel layer of native collagen, and a monolayer of human aortic endothelial cells was grown on top of the collagen layer. Exposure of this coculture to human monocytes in the presence of chemotactic factor rFMLP resulted in monocyte attachment to the endothelial cells followed by migration across the endothelial monolayer into the collagen layer of the subendothelial space. This type of culture can also be treated with LDL to generate foam cells. The foam cells can then be harvested and their pattern of gene expression compared to that of untreated cells as explained below in sub-section 5.1.2.

5.1.1.4. In Vivo Monocyte Paradigm

An alternative embodiment of such paradigms for the study of monocytes, hereinafter referred to as Paradigm B, involves differential treatment of human subjects through the dietary control of lipid consumption. Such human subjects are held on a low fat/low cholesterol diet for three weeks, at which time blood is drawn, monocytes are isolated according to the methods routinely practiced in the art, and RNA is purified, as described below, in sub-section 5.1.2. These same patients are subsequently switched to a high fat/high cholesterol diet and monocyte RNA is purified again. The patients may also be fed a third, combination diet containing high fat/low cholesterol and monocyte RNA may be purified once again. The order in which patients receive the diets may be varied. The RNA derived from patients maintained on two of the diets, or on all three diets, may then be compared and analyzed for differential gene expression as, explained below in sub-section 5.1.2.

5.1.1.5. Endothelial Cell-Il-1-Paradigm

In addition to the detection of differential gene expression in monocytes, paradigms focusing on endothelial cells may be used to detect genes involved in cardiovascular disease. In one such paradigm, hereinafter referred to as Paradigm C, human umbilical vein endothelial cells HUVEC's) are grown in vitro. Experimental cultures are treated with human IL-1p, a factor known to be involved in the inflammatory response, in order to mimic the physiologic conditions involved in the atherosclerotic state. Alternatively experimental HUVEC cultures may be treated with lysophosphatidylcholine, a major phospholipid component of atherogenic lipoproteins or oxidized human LDL. Control cultures are grown in the absence of these compounds.

After a certain period of treatment, experimental and control cells are harvested and analyzed for differential gene expression as described in sub-section 5.1.2, below.

5.1.1.6. Endothelial Cell-Shear Stress Paradigm

In another paradigm involving endothelial cells, hereinafter referred to as Paradigm D, cultures are exposed to fluid shear stress which is thought to be responsible for the prevalence of atherosclerotic lesions in areas of unusual circulatory flow. Unusual blood flow also plays a role in the harmful effects of ischemia/reperfusion, wherein an organ receiving inadequate blood supply is suddenly reperfused with an overabundance of blood when the obstruction is overcome.

Cultured HUVEC monolayers are exposed to laminar shear stress by rotating the culture in a specialized apparatus containing liquid culture medium (Nagel et al., 1994, J. Clin. Invest. 94: 885–891). Static cultures grown in the same medium serve as controls. After a certain period of exposure to shear stress, experimental and control cells are harvested and analyzed for differential gene expression as described in sub-section 5.1.2, below. The Example presented in Section 7, below, demonstrates the use of such a shear stressed endothelial cell paradigm to identify sequences which are differentially expressed in exposed versus control cells.

In all such paradigms designed to identify genes which are involved in cardiovascular disease, including but not limited to those described above in Sections 5.1.1.1 through 5.1.1.6, compounds such as drugs known to have an ameliorative effect on the disease symptoms may be incorporated into the experimental system. Such compounds may include known therapeutics, as well as compounds that are not useful as therapeutics due to their harmful side effects. Test cells that are cultured as explained in the paradigms described in Sections 5.1.1.1 through 5.1.1.6, for example, may be exposed to one of these compounds and analyzed for differential gene expression with respect to untreated cells, according to the methods described below in Section 5.1.2. In principle, according to the particular paradigm, any cell type involved in the disease may be treated at any stage of the disease process by these compounds.

Test cells may also be compared to unrelated cells (e.g., fibroblasts) that are also treated with the compound, in order to screen out generic effects on gene expression that might not be related to the disease. Such generic effects might be manifest by changes in gene expression that are common to the test cells and the unrelated cells upon treatment with the compound.

By these methods, the genes and gene products upon which these compounds act can be identified and used in the assays described below to identify novel therapeutic compounds for the treatment of cardiovascular disease.

5.1.2. Analysis of Paradigm Material

In order to identify differentially expressed genes, RNA, either total or mRNA, may be isolated from one or more tissues of the subjects utilized in paradigms such as those described earlier in this Section. RNA samples are obtained from tissues of experimental subjects and from corresponding tissues of control subjects. Any RNA isolation technique which does not select against the isolation of mRNA may be utilized for the purification of such RNA samples. See, for example, Sambrook et al., 1989, Molecular Cloning, A Laboratory Manual, Cold Spring Harbor Press, N.Y.; and Ausubel, F. M. et al., eds., 1987–1993, Current Protocols in Molecular Biology, John Wiley & Sons, Inc. New York, both of which are incorporated herein by reference in their entirety. Additionally, large numbers of tissue samples may readily be processed using techniques well known to those of skill in the art, such as, for example, the single-step RNA isolation process of Chomczynski, P. (1989, U.S. Pat. No. 4,843,155), which is incorporated herein by reference in its entirety.

Transcripts within the collected RNA samples which represent RNA produced by differentially expressed genes may be identified by utilizing a variety of methods which are well known to those of skill in the art. For example, differential screening (Tedder, T. F. et al., 1988, Proc. Natl. Acad. Sci. USA 85:208–212), subtractive hybridization (Hedrick, S. M. et al., 1984, Nature 308:149–153; Lee, S. W. et al., 1984, Proc. Natl. Acad. Sci. USA 88:2825), and, preferably, differential display (Liang, P., and Pardee, A. B., 1993, U.S. Pat. No. 5,262,311, which is incorporated herein by reference in its entirety), may be utilized to identify nucleic acid sequences derived from genes that are differentially expressed.

Differential screening involves the duplicate screening of a cDNA library in which one copy of the library is screened with a total cell cDNA probe corresponding to the mRNA population of one cell type while a duplicate copy of the cDNA library is screened with a total cDNA probe corresponding to the mRNA population of a second cell type. For example, one cDNA probe may correspond to a total cell cDNA probe of a cell type derived from a control subject, while the second cDNA probe may correspond to a total cell cDNA probe of the same cell type derived from an experimental subject. Those clones which hybridize to one probe but not to the other potentially represent clones derived from genes differentially expressed in the cell type of interest in control versus experimental subjects.

Subtractive hybridization techniques generally involve the isolation of mRNA taken from two different sources, e.g., control and experimental tissue, the hybridization of the mRNA or single-stranded cDNA reverse-transcribed from the isolated mRNA, and the removal of all hybridized, and therefore double-stranded, sequences. The remaining non-hybridized, single-stranded cDNAs, potentially represent clones derived from genes that are differentially expressed in the two mRNA sources. Such single-stranded cDNAs are then used as the starting material for the construction of a library comprising clones derived from differentially expressed genes.

The differential display technique describes a procedure, utilizing the well known polymerase chain reaction (PCR; the experimental embodiment set forth in Mullis, K. B., 1987, U.S. Pat. No. 4,683,202) which allows for the identification of sequences derived from genes which are differentially expressed. First, isolated RNA is reverse-transcribed into single-stranded cDNA, utilizing standard techniques which are well known to those of skill in the art. Primers for the reverse transcriptase reaction may include, but are not limited to, oligo dT-containing primers, preferably of the reverse primer type of oligonucleotide described below. Next, this technique uses pairs of PCR primers, as described below, which allow for the amplification of clones representing a random subset of the RNA transcripts present within any given cell. Utilizing different pairs of primers allows each of the mRNA transcripts present in a cell to be amplified. Among such amplified transcripts may be identified those which have been produced from differentially expressed genes.

The reverse oligonucleotide primer of the primer pairs may contain an oligo dT stretch of nucleotides, preferably eleven nucleotides long, at its 5' end, which hybridizes to the poly(A) tail of mRNA or to the complement of a cDNA reverse transcribed from an mRNA poly(A) tail. Second, in order to increase the specificity of the reverse primer, the primer may contain one or more, preferably two, additional nucleotides at its 3' end. Because, statistically, only a subset of the mRNA derived sequences present in the sample of interest will hybridize to such primers, the additional nucleotides allow the primers to amplify only a subset of the mRNA derived sequences present in the sample of interest. This is preferred in that it allows more accurate and complete visualization and characterization of each of the bands representing amplified sequences.

The forward primer may contain a nucleotide sequence expected, statistically, to have the ability to hybridize to cDNA sequences derived from the tissues of interest. The nucleotide sequence may be an arbitrary one, and the length of the forward oligonucleotide primer may range from about 9 to about 13 nucleotides, with about 10 nucleotides being preferred. Arbitrary primer sequences cause the lengths of the amplified partial cDNAs produced to be variable, thus allowing different clones to be separated by using standard denaturing sequencing gel electrophoresis. PCR reaction conditions should be chosen which optimize amplified product yield and specificity, and, additionally, produce amplified products of lengths which may be resolved utilizing standard gel electrophoresis techniques. Such reaction conditions are well known to those of skill in the art, and important reaction parameters include, for example, length and nucleotide sequence of oligonucleotide primers as discussed above, and annealing and elongation step temperatures and reaction times.

The pattern of clones resulting from the reverse transcription and amplification of the mRNA of two different cell types is displayed via sequencing gel electrophoresis and compared. Differences in the two banding patterns indicate potentially differentially expressed genes.

Once potentially differentially expressed gene sequences have been identified via bulk techniques such as, for example, those described above, the differential expression of such putatively differentially expressed genes should be corroborated. Corroboration may be accomplished via, for example, such well known techniques as Northern analysis and/or RT-PCR.

Upon corroboration, the differentially expressed genes may be further characterized, and may be identified as target and/or fingerprint genes, as discussed, below, in Section 5.3.

Also, amplified sequences of differentially expressed genes obtained through, for example, differential display may be used to isolate full length clones of the corresponding gene. The fall length coding portion of the gene may readily be isolated, without undue experimentation, by molecular biological techniques well known in the art. For example, the isolated differentially expressed amplified fragment may be labeled and used to screen a cDNA library. Alternatively, the labeled fragment may be used to screen a genomic library.

PCR technology may also be utilized to isolate fall length cDNA sequences. As described, above, in this Section, the isolated, amplified gene fragments obtained through differential display have 5' terminal ends at some random point within the gene and have 3' terminal ends at a position preferably corresponding to the 3' end of the transcribed portion of the gene. Once nucleotide sequence information from an amplified fragment is obtained, the remainder of the gene (i.e., the 5' end of the gene, when utilizing differential display) may be obtained using, for example, RT-PCR.

In one embodiment of such a procedure for the identification and cloning of fall length gene sequences, RNA may be isolated, following standard procedures, from an appropriate tissue or cellular source. A reverse transcription reaction may then be performed on the RNA using an oligonucleotide primer complimentary to the mRNA that corresponds to the amplified fragment, for the priming of first strand synthesis. Because the primer is anti-parallel to the mRNA, extension will proceed toward the 5' end of the mRNA. The resulting RNA/DNA hybrid may then be "tailed" with guanines using a standard terminal transferase reaction, the hybrid may be digested with RNAase H, and second strand synthesis may then be primed with a poly-C primer. Using the two primers, the 5' portion of the gene is amplified using PCR. Sequences obtained may then be isolated and recombined with previously isolated sequences to generate a full-length cDNA of the differentially expressed genes of the invention. For a review of cloning strategies and recombinant DNA techniques, see e.g., Sambrook et al., 1989, supra; and Ausubel et al., 1989, supra.

5.2. Identification of Pathway Genes

This section describes methods for the identification of genes, termed "pathway genes" involved in cardiovascular disease. "Pathway gene", as used herein, refers to a gene whose gene product exhibits the ability to interact with gene products involved in cardiovascular disease. A pathway gene may be differentially expressed and, therefore, may additionally have the characteristics of a target and/or fingerprint gene.

Any method suitable for detecting protein-protein interactions may be employed for identifying pathway gene products by identifying interactions between gene products and gene products known to be involved in cardiovascular disease. Such known gene products may be cellular or extracellular proteins. Those gene products which interact with such known gene products represent pathway gene products and the genes which encode them represent pathway genes.

Among the traditional methods which may be employed are co-immunoprecipitation, crosslinking and co-purification through gradients or chromatographic columns. Utilizing procedures such as these allows for the identification of pathway gene products. Once identified, a pathway gene product may be used, in conjunction with standard techniques, to identify its corresponding pathway gene. For example, at least a portion of the amino acid sequence of the pathway gene product may be ascertained using techniques well known to those of skill in the art, such as via the Edman degradation technique (see, ., Creighton, 1983, Proteins: Structures and Molecular Principles, W. H. Freeman & Co., N.Y., pp.34–49). The amino acid sequence obtained maybe used as a guide for the generation of oligonucleotide mixtures that can be used to screen for pathway gene sequences. Screening may be accomplished, for example by standard hybridization or PCR techniques. Techniques for the generation of oligonucleotide mixtures and screening are well-known. (See, e.g., Ausubel, supra., and PCR Protocols: A Guide to Methods and Applications, 1990, Innis, M. et al., eds. Academic Press, Inc., New York).

Additionally, methods maybe employed which result in the simultaneous identification of pathway genes which encode the protein interacting with a protein involved in cardiovascular disease. These methods include, for example, probing expression libraries with labeled protein known or suggested to be involved in cardiovascular disease, using this protein in a manner similar to the well known technique of antibody probing of λgt11 libraries.

One such method which detects protein interactions in vivo, the two-hybrid system, is described in detail for illustration only and not by way of limitation. One version of this system has been described (Chien et al., 1991, Proc. Natl. Acad. Sci. USA, 88:9578–9582) and is commercially available from Clontech (Palo Alto, Calif.).

Briefly, utilizing such a system, plasmids are constructed that encode two hybrid proteins: one consists of the DNA-binding domain of a transcription activator protein fused to a known protein, and the other consists of the activator protein's activation domain fused to an unknown protein that is encoded by a cDNA which has been recombined into this plasmid as part of a cDNA library. The plasmids are transformed into a strain of the yeast Saccharomyces cerevisiae that contains a reporter gene (e.g., lacZ) whose regulatory region contains the activator's binding sites. Either hybrid protein alone cannot activate transcription of the reporter gene; the DNA-binding domain hybrid, because it does not provide activation function and the activation domain hybrid, because it cannot localize to the activator's binding sites. Interaction of the two proteins reconstitutes the functional activator protein and results in expression of the reporter gene, which is detected by an assay for the reporter gene product.

The two-hybrid system or related methodology may be used to screen activation domain libraries for proteins that interact with a known "bait" gene protein. Total genomic or cDNA sequences may be fused to the DNA encoding an activation domain. Such a library and a plasmid encoding a hybrid of the bait gene protein fused to the DNA-binding domain may be cotransformed into a yeast reporter strain, and the resulting transformants may be screened for those that express the reporter gene. These colonies may be purified and the library plasmids responsible for reporter gene expression may be isolated. DNA sequencing may then be used to identify the proteins encoded by the library plasmids.

For example, and not by way of limitation, the bait gene may be cloned into a vector such that it is translationally fused to the DNA encoding the DNA-binding domain of the GAL4 protein. Also by way of example, for the isolation of genes involved in cardiovascular disease, previously isolated genes known or suggested to play a part in cardiovascular disease may be used as the bait genes. These include but are not limited to the genes for bFGF, IGF-I, VEGF, IL-1, M-CSF, TGFβ, TGFα, TNFα, HB-EGF, PDGF, IFN-γ, and GM-CSF, to name a few.

A cDNA library of the cell line from which proteins that interact with bait gene are to be detected can be made using methods routinely practiced in the art. According to the particular system described herein, for example, the cDNA fragments may be inserted into a vector such that they are translationally fused to the activation domain of GAL4. This library may be co-transformed along with the bait gene-GAL4 fusion plasmid into a yeast strain which contains a lacZ gene driven by a promoter which contains the GAL4 activation sequence. A cDNA encoded protein, fused to the GAL4 activation domain, that interacts with bait gene will reconstitute an active GAL4 protein and thereby drive expression of the lacZ gene. Colonies which express lacZ may be detected by their blue color in the presence of X-gal. The cDNA may then be purified from these strains, and used to produce and isolate the bait gene-interacting protein using techniques routinely practiced in the art.

Once a pathway gene has been identified and isolated, it may be further characterized as, for example, discussed below, in Section 5.3.

A preferred embodiment of the use of the yeast two-hybrid system is described in detail in the example in Section 12, below. As described in Section 12, the yeast two-hybrid system was used to detect the interaction between the protein products of two target genes, rchd534 and fchd540.

5.3. Characterization of Differentially Expressed and Pathway Genes

Differentially expressed genes, such as those identified via the methods discussed, above, in Section 5.1.1, pathway genes, such as those identified via the methods discussed, above, in Section 5.2, as well as genes identified by alternative means, may be further characterized by utilizing, for example, methods such as those discussed herein. Such genes will be referred to herein as "identified genes".

Analyses such as those described herein will yield information regarding the biological function of the identified genes. An assessment of the biological function of the differentially expressed genes, in addition, will allow for their designation as target and/or fingerprint genes. Specifically, any of the differentially expressed genes whose further characterization indicates that a modulation of the gene's expression or a modulation of the gene product's activity may ameliorate cardiovascular disease will be designated "target genes", as defined, above, in Section 5.1. Such target genes and target gene products, along with those discussed below, will constitute the focus of the compound discovery strategies discussed, below, in Section 5.5.

Any of the differentially expressed genes whose further characterization indicates that such modulations may not positively affect cardiovascular disease, but whose expression pattern contributes to a gene expression "fingerprint pattern" correlative of, for example, a, cardiovascular disease condition will be designated a "fingerprint gene". "Fingerprint patterns" will be more fully discussed, below, in Section 5.8. It should be noted that each of the target genes may also function as fingerprint genes, as may all or a subset of the pathway genes.

It should further be noted that the pathway genes may also be characterized according to techniques such as those described herein. Those pathway genes which yield information indicating that they are differentially expressed and that modulation of the gene's expression or a modulation of the gene products activity may ameliorate cardiovascular disease will be also be designated "target genes". Such target genes and target gene products, along with those discussed above, will constitute the focus of the compound discovery strategies discussed, below, in Section 5.5.

It should be additionally noted that the characterization of one or more of the pathway genes may reveal a lack of differential expression, but evidence that modulation of the gene's activity or expression may, nonetheless, ameliorate cardiovascular disease symptoms. In such cases, these genes and gene products would also be considered a focus of the compound discovery strategies of Section 5.5, below.

In instances wherein a pathway gene's characterization indicates that modulation of gene expression or gene product activity may not positively affect cardiovascular disease, but whose expression is differentially expressed and which contributes to a gene expression fingerprint pattern correlative of, for example, a cardiovascular disease state, such pathway genes may additionally be designated as fingerprint genes.

Among the techniques whereby the identified genes may be further characterized, the nucleotide sequence of the identified genes, which may be obtained by utilizing standard techniques well known to those of skill in the art, may be used to further characterize such genes. For example, the sequence of the identified genes may reveal homologies to one or more known sequence motifs which may yield information regarding the biological function of the identified gene product.

Second, an analysis of the tissue distribution of the mRNA produced by the identified genes may be conducted, utilizing standard techniques well known to those of skill in the art. Such techniques may include, for example, Northern analyses and RT-PCR. Such analyses provide information as to whether the identified genes are expressed in tissues expected to contribute to cardiovascular disease. Such analyses may also provide quantitative information regarding steady state mRNA regulation, yielding data concerning which of the identified genes exhibits a high level of regulation in, preferably, tissues which may be expected to contribute to cardiovascular disease.

Such analyses may also be performed on an isolated cell population of a particular cell type derived from a given tissue. Additionally, standard in situ hybridization techniques may be utilized to provide information regarding which cells within a given tissue express the identified gene. Such analyses may provide information regarding the biological function of an identified gene relative to cardiovascular disease in instances wherein only a subset of the cells within the tissue is thought to be relevant to cardiovascular disease.

Third, the sequences of the identified genes may be used, utilizing standard techniques, to place the genes onto genetic maps, e.g., mouse (Copeland & Jenkins, 1991, Trends in Genetics 7: 113–118) and human genetic maps (Cohen, et al., 1993, Nature 366: 698–701). Such mapping information may yield information regarding the genes' importance to human disease by, for example, identifying genes which map near genetic regions to which known genetic cardiovascular disease tendencies map.

Fourth, the biological function of the identified genes may be more directly assessed by utilizing relevant in vivo and in vitro systems. In vivo systems may include, but are not limited to, animal systems which naturally exhibit cardiovascular disease predisposition, or ones which have been engineered to exhibit such symptoms, including but not limited to the apoE-deficient atherosclerosis mouse model (Plump et al., 1992, Cell 71: 343–353). Such systems are discussed in Section 5.4.4.1, below.

In vitro systems may include, but are not limited to, cell-based systems comprising cell types known or suspected of involvement in cardiovascular disease. Such systems are discussed in detail, below, in Section 5.4.4.2.

In further characterizing the biological function of the identified genes, the expression of these genes may be modulated within the in vivo and/or in vitro systems, i.e., either over or underexpressed, and the subsequent effect on the system then assayed. Alternatively, the activity of the product of the identified gene may be modulated by either increasing or decreasing the level of activity in the in vivo and/or in vitro system of interest, and its subsequent effect then assayed.

The information obtained through such characterizations may suggest relevant methods for the treatment of cardiovascular disease involving the gene of interest. For example, treatment may include a modulation of gene expression and/or gene product activity. Characterization procedures such as those described herein may indicate where such modulation should involve an increase or a decrease in the expression or activity of the gene or gene product of interest.

For example, genes which are up-regulated under disease conditions may be involved in causing or exacerbating the disease condition. Treatments directed at down-regulating the activity of such harmfully expressed genes will ameliorate the disease condition. On the other hand, the up-regulation of genes under disease conditions may be part of a protective response by affected cells. Treatments directed at increasing or enhancing the activity of such up-regulated gene products, especially in individuals lacking normal up-regulation, will similarly ameliorate disease conditions. Such methods of treatment are discussed, below, in Section 5.6.

5.4. Differentially Expressed and Pathway Genes

Identified genes, which include but are not limited to differentially expressed genes such as those identified in Section 5.1.1, above, and pathway genes, such as those identified in Section 5.2, above, are described herein. Specifically, the nucleic acid sequences and gene products of such identified genes are described herein. Further, antibodies directed against the identified genes' products, and cell- and animal-based models by which the identified genes may be further characterized and utilized are also discussed in this Section.

5.4.1. Differentially Expressed and Pathway Gene Sequences

The differentially expressed and pathway genes of the invention are listed below, in Table 1. Differentially expressed and pathway gene nucleotide sequences are shown in FIGS. 1A–1D, 2A–2E, 3A–3C, 4A–4B, 5A–5B, 6A–6D and 8.

Table 1 lists differentially expressed genes identified through, for example, the paradigms discussed, above, in Section 5. 1.1, and below, in the examples presented in Sections 6 through 9. Table 1 also summarizes information regarding the further characterization of such genes.

First, the paradigm used initially to detect the differentially expressed gene is described under the column headed "Paradigm of Original Detection". The expression patterns of those genes which have been shown to be differentially expressed, for example, under one or more of the paradigm conditions described in Section 5.1.1 are summarized under the column headed "Paradigm Expression Pattern". For each of the tested genes, the paradigm which was used and the difference in the expression of the gene among the samples generated is shown. ⇑ indicates that gene expression is up-regulated (i.e., there is an increase in the amount of detectable mRNA) among the samples generated, while ⇓ indicates that gene expression is down-regulated (i.e., there is a decrease in the amount of detectable mRNA) among the samples generated. "Detectable" as used herein, refers to levels of mRNA which are detectable via, for example, standard Northern and/or RT-PCR techniques which are well known to those of skill in the art.

Cell types in which differential expression was detected are also summarized in Table 1 under the column headed "Cell Type Detected in". The column headed "Chromosomal Location" provides the human chromosome number on which the gene is located. Additionally, in instances wherein the genes contain nucleotide sequences similar or homologous to sequences found in nucleic acid databases, references to such similarities are listed.

The genes listed in Table 1 may be obtained using cloning methods well known to those skilled in the art, including but not limited to the use of appropriate probes to detect the genes within an appropriate cDNA or gDNA (genomic DNA) library. (See, for example, Sambrook et al., 1989, Molecular Cloning: A Laboratory Manual, Cold Spring Harbor Laboratories, which is incorporated by reference herein in its entirety). Probes for the novel sequences reported herein may be obtained directly from the isolated clones deposited with the ATCC, as indicated in Table 2, below. Alternatively, oligonucleotide probes for the novel genes may be synthesized based on the DNA sequences disclosed herein in FIGS. 1A–5B.

The sequence obtained from clones containing partial coding sequences or non-coding sequences can be used to obtain the entire coding region by using the RACE method (Chenchik, et al., 1995, CLONTECHniques (X) 1: 5–8; Barnes, 1994, Proc. Natl. Acad. Sci. USA 91: 2216–2220; and Cheng et al., Proc. Natl. Acad. Sci. USA 91: 5695–5699). Oligonucleotides can be designed based on the sequence obtained from the partial clone that can amplify a reverse transcribed mRNA encoding the entire coding sequence.

Alternatively, probes can be used to screen cDNA libraries prepared from an appropriate cell or cell line in which the gene is transcribed. For example, the genes described herein that were detected in monocytes may be cloned from a cDNA library prepared from monocytes isolated as described in Section 6.1.1, below.

The genes described herein that were detected in endothelial cells may also be cloned from a cDNA library constructed from endothelial cells isolated as described in Progress in Hemostasis and Thrombosis, Vol.3, P. Spaet, editor, Grune & Stratton Inc., New York, 1–28. Alternatively, the genes may be retrieved from a human placenta cDNA library (Clontech Laboratories, Palo Alto, Calif.), according to Takahashi et al., 1990, supra; a HUVEC cDNA library as described in Jones et al. 1993, supra; or an acute lymphoblastic leukemia (SUP-B2) cDNA library as described in Cleary et al., 1986, supra, for example. Genomic DNA libraries can be prepared from any source.

TABLE 1

| | | Differentially Expressed and Pathway Genes | | | | |
|---|---|---|---|---|---|---|
| Gene | Seq. ID # | Paradigm of Original Detection | Paradigm Expr. Pattern | Cell Type Detected in | Ref | Seq. |
| fchd531 | 1 | D (Section 5.1.1.6) | ⇓ | Endothelial | New,1 | FIGS. 1A–1A–1D |
| fchd540 | 3 | D | ⇑ | Endothelial | New,2 | FIGS. 2A–2E |
| fchd545 | 5 | D | ⇓ | Endothelial | New,3 | FIGS. 3A–3C |
| fchd602 | 7 | A (Section 5.1.1.1) | ⇑ | Monocytes | New,4 | FIGS. 4A–4B |
| fchd605 | 9 | A | ⇑ | Monocytes | New,5 | FIGS. 5A–5B |
| rchd534 | 10 | D | ⇑ | Endothelial | | FIGS. 6A–6B |

1. GenBank accession number U05343.
2. Drosohila Mothers against dpp (Mad), Sekelsky et al., 1995, Genetics 139: 1347–1358.

TABLE 1-continued

Differentially Expressed and Pathway Genes

| Gene | Seq. ID # | Paradigm of Original Detection | Paradigm Expr. Pattern | Cell Type Detected in | Ref | Seq. |
|------|-----------|-------------------------------|------------------------|----------------------|-----|------|

3. Human Voltage-dependent Anion Channel, Blachly-Dyson E., et al., 1993, J. Biol. Chem. 268: 1835–1841; and EST T24012
4. Rat Cl-6, Diamond, R.H., et al., 1993, J. Biol. Chem. 268: 15185–15192.
5. Mouse gly96, Charles, C.H., et al., 1993, Oncogene 8: 797–801; and EST T49532.

Table 2, below, lists the strains of *E. coli* deposited with the ATCC that contain plasmids bearing the novel genes listed in Table 1.

TABLE 2

| GENE | Strain Deposited with ATCC |
|------|---------------------------|
| fchd531 | pFCHD531 |
| fchd540 | pFCHD540 |
| fchd545 | fchd545 |
| rchd534 | FCHD534 |

As used herein, "differentially expressed gene" (i.e. target and fingerprint gene) or "pathway gene" refers to (a) a gene containing at least one of the DNA sequences disclosed herein (as shown in FIGS. 1A–6D), or contained in the clones listed in Table 2, as deposited with the ATCC; (b) any DNA sequence that encodes the amino acid sequence encoded by the DNA sequences disclosed herein (as shown in FIGS. 1A–6D), contained in the clones, listed in Table 2, as deposited with the ATCC or contained within the coding region of the gene to which the DNA sequences disclosed herein (as shown in FIGS. 1A–6D) or contained in the clones listed in Table 2, as deposited with the ATCC, belong; (c) any DNA sequence that hybridizes to the complement of the coding sequences disclosed herein, contained in the clones listed in Table 2, as deposited with the ATCC, or contained within the coding region of the gene to which the DNA sequences disclosed herein (as shown in FIGS. 1A–6D) or contained in the clones listed in Table 2, as deposited with the ATCC, belong, under highly stringent conditions, e.g., hybridization to filter-bound DNA in 0. 5 M NaHPO$_4$, 7% sodium dodecyl sulfate (SDS), 1 mM EDTA at 65° C., and washing in 0.1×SSC/0.1% SDS at 68° C. (Ausubel F. M. et al., eds., 1989, Current Protocols in Molecular Biology, Vol. I, Green Publishing Associates, Inc., and John Wiley & sons, Inc., New York, at p. 2.10.3) and encodes a gene product functionally equivalent to a gene product encoded by sequences contained within the clones listed in Table 2; and/or (d) any DNA sequence that hybridizes to the complement of the coding sequences disclosed herein, (as shown in FIGS. 1A–6D) contained in the clones listed in Table 2, as deposited with the ATCC or contained within the coding region of the gene to which DNA sequences disclosed herein (as shown in FIGS. 1A–5B) or contained in the clones, listed in Table 2, as deposited with the ATCC, belong, under less stringent conditions, such as moderately stringent conditions, e.g., washing in 0.2×SSC/ 0.1% SDS at 42° C. (Ausubel et al., 1989, supra), yet which still encodes a functionally equivalent gene product.

The invention also includes nucleic acid molecules, preferably DNA molecules, that hybridize to, and are therefore the complements of, the DNA sequences (a) through (c), in the preceding paragraph. Such hybridization conditions may be highly stringent or less highly stringent, as described above. In instances wherein the nucleic acid molecules are deoxyoligonucleotides ("oligos"), highly stringent conditions may refer, e.g., to washing in 6×SSC/0.05% sodium pyrophosphate at 37° C. (for 14-base oligos), 48° C. (for 17-base oligos), 55° C. (for 20-base oligos), and 60° C. (for 23-base oligos). These nucleic acid molecules may act as target gene antisense molecules, useful, for example, in target gene regulation and/or as antisense primers in amplification reactions of target gene nucleic acid sequences. Further, such sequences may be used as part of ribozyme and/or triple helix sequences, also useful for target gene regulation. Still further, such molecules may be used as components of diagnostic methods whereby the presence of a cardiovascular disease-causing allele, may be detected.

The invention also encompasses (a) DNA vectors that contain any of the foregoing coding sequences and/or their complements (i.e., antisense); (b) DNA expression vectors that contain any of the foregoing coding sequences operatively associated with a regulatory element that directs the expression of the coding sequences; and (c) genetically engineered host cells that contain any of the foregoing coding sequences operatively associated with a regulatory element that directs the expression of the coding sequences in the host cell. As used herein, regulatory elements include but are not limited to inducible and non-inducible promoters, enhancers, operators and other elements known to those skilled in the art that drive and regulate expression. The invention includes fragments of any of the DNA sequences disclosed herein.

In addition to the gene sequences described above, homologues of such sequences, as may, for example be present in other species, may be identified and may be readily isolated, without undue experimentation, by molecular biological techniques well known in the art. Further, there may exist genes at other genetic loci within the genome that encode proteins which have extensive homology to one or more domains of such gene products. These genes may also be identified via similar techniques.

For example, the isolated differentially expressed gene sequence may be labeled and used to screen a cDNA library constructed from mRNA obtained from the organism of interest. Hybridization conditions will be of a lower stringency when the cDNA library was derived from an organism different from the type of organism from which the labeled sequence was derived. Alternatively, the labeled fragment may be used to screen a genomic library derived from the organism of interest, again, using appropriately stringent conditions. Such low stringency conditions will be well known to those of skill in the art, and will vary predictably depending on the specific organisms from which the library and the labeled sequences are derived. For guidance regarding such conditions see, for example, Sambrook et al., 1989, Molecular Cloning, A Laboratory Manual, Cold Springs Harbor Press, N.Y.; and Ausubel et al., 1989, Current Protocols in Molecular Biology, Green Publishing Associates and Wiley Interscience, N.Y.

Further, a previously unknown differentially expressed or pathway gene-type sequence may be isolated by performing PCR using two degenerate oligonucleotide primer pools designed on the basis of amino acid sequences within the gene of interest. The template for the reaction may be cDNA obtained by reverse transcription of mRNA prepared from human or non-human cell lines or tissue known or suspected to express a differentially expressed or pathway gene allele.

The PCR product may be subcloned and sequenced to insure that the amplified sequences represent the sequences of a differentially expressed or pathway gene-like nucleic acid sequence. The PCR fragment may then be used to isolate a full length cDNA clone by a variety of methods. For example, the amplified fragment may be labeled and used to screen a bacteriophage cDNA library. Alternatively, the labeled fragment may be used to screen a genomic library.

PCR technology may also be utilized to isolate full length cDNA sequences. For example, RNA may be isolated, following standard procedures, from an appropriate cellular or tissue source. A reverse transcription reaction may be performed on the RNA using an oligonucleotide primer specific for the most 5' end of the amplified fragment for the priming of first strand synthesis. The resulting RNA/DNA hybrid may then be "tailed" with guanines using a standard terminal transferase reaction, the hybrid may be digested with RNAase H, and second strand synthesis may then be primed with a poly-C primer. Thus, cDNA sequences upstream of the amplified fragment may easily be isolated. For a review of cloning strategies which may be used, see e.g., Sambrook et al., 1989, supra.

In cases where the differentially expressed or pathway gene identified is the normal, or wild type, gene, this gene may be used to isolate mutant alleles of the gene. Such an isolation is preferable in processes and disorders which are known or suspected to have a genetic basis. Mutant alleles may be isolated from individuals either known or suspected to have a genotype which contributes to cardiovascular disease symptoms. Mutant alleles and mutant allele products may then be utilized in the therapeutic and diagnostic assay systems described below.

A cDNA of the mutant gene may be isolated, for example, by using PCR, a technique which is well known to those of skill in the art. In this case, the first cDNA strand may be synthesized by hybridizing an oligo-dT oligonucleotide to mRNA isolated from tissue known or suspected to be expressed in an individual putatively carrying the mutant allele, and by extending the new strand with reverse transcriptase. The second strand of the cDNA is then synthesized using an oligonucleotide that hybridizes specifically to the 5' end of the normal gene. Using these two primers, the product is then amplified via PCR, cloned into a suitable vector, and subjected to DNA sequence analysis through methods well known to those of skill in the art. By comparing the DNA sequence of the mutant gene to that of the normal gene, the mutation(s) responsible for the loss or alteration of function of the mutant gene product can be ascertained.

Alternatively, a genomic or cDNA library can be constructed and screened using DNA or RNA, respectively, from a tissue known to or suspected of expressing the gene of interest in an individual suspected of or known to carry the mutant allele. The normal gene or any suitable fragment thereof may then be labeled and used as a probed to identify the corresponding mutant allele in the library. The clone containing this gene may then be purified through methods routinely practiced in the art, and subjected to sequence analysis as described, above, in this Section.

Additionally, an expression library can be constructed utilizing DNA isolated from or cDNA synthesized from a tissue known to or suspected of expressing the gene of interest in an individual suspected of or known to carry the mutant allele. In this manner, gene products made by the putatively mutant tissue may be expressed and screened using standard antibody screening techniques in conjunction with antibodies raised against the normal gene product, as described, below, in Section 5.4.3. (For screening techniques, see, for example, Harlow, E. and Lane, eds., 1988, "Antibodies: A Laboratory Manual", Cold Spring Harbor Press, Cold Spring Harbor.) In cases where the mutation results in an expressed gene product with altered function (e.g., as a result of a missense mutation), a polyclonal set of antibodies are likely to cross-react with the mutant gene product. Library clones detected via their reaction with such labeled antibodies can be purified and subjected to sequence analysis as described in this Section, above.

5.4.2. Differentially Expressed and Pathway Gene Products

Differentially expressed and pathway gene products include those proteins encoded by the differentially expressed and pathway gene sequences described in Section 5.4.1, above. Specifically, differentially expressed and pathway gene products may include differentially expressed and pathway gene polypeptides encoded by the differentially expressed and pathway gene sequences contained in the clones listed in Table 2, above, as deposited with the ATCC, or contained in the coding regions of the genes to which DNA sequences disclosed herein (in FIGS. 1A–6D) or contained in the clones, listed in Table 2, as deposited with the ATCC, belong, for example.

In addition, differentially expressed and pathway gene products may include proteins that represent functionally equivalent gene products. Such an equivalent differentially expressed or pathway gene product may contain deletions, additions or substitutions of amino acid residues within the amino acid sequence encoded by the differentially expressed or pathway gene sequences described, above, in Section 5.4.1, but which result in a silent change, thus producing a functionally equivalent differentially expressed on pathway gene product. Amino acid substitutions may be made on the basis of similarity in polarity, charge, solubility, hydrophobicity, hydrophilicity, and/or the amphipathic nature of the residues involved.

For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid. "Functionally equivalent", as utilized herein, refers to a protein capable of exhibiting a substantially similar in vivo activity as the endogenous differentially expressed or pathway gene products encoded by the differentially expressed or pathway gene sequences described in Section 5.4.1, above. Alternatively, when utilized as part of assays such as those described, below, in Section 5.5, "functionally equivalent" may refer to peptides capable of interacting with other cellular or extracellular molecules in a manner substantially similar to the way in which the corresponding portion of the endogenous differentially expressed or pathway gene product would.

The differentially expressed or pathway gene products may be produced by recombinant DNA technology using techniques well known in the art. Thus, methods for preparing the differentially expressed or pathway gene polypeptides and peptides of the invention by expressing nucleic acid encoding differentially expressed or pathway gene sequences are described herein. Methods which are well known to those skilled in the art can be used to construct expression vectors containing differentially expressed or pathway gene protein coding sequences and appropriate transcriptional/translational control signals. These methods include, for example, in vitro recombinant DNA techniques, synthetic techniques and in vivo recombination/genetic recombination. See, for example, the techniques described in Sambrook et al., 1989, supra, and Ausubel et al., 1989, supra. Alternatively, RNA capable of encoding differentially expressed or pathway gene protein sequences may be chemically synthesized using, for example, synthesizers. See, for example, the techniques described in "Oligonucleotide Synthesis", 1984, Gait, M. J. ed., IRL Press, Oxford, which is incorporated by reference herein in its entirety.

A variety of host-expression vector systems may be utilized to express the differentially expressed or pathway gene coding sequences of the invention. Such host-expression systems represent vehicles by which the coding sequences of interest may be produced and subsequently purified, but also represent cells which may, when transformed or transfected with the appropriate nucleotide coding sequences, exhibit the differentially expressed or pathway gene protein of the invention in situ. These include but are not limited to microorganisms such as bacteria (e.g., *E. coli, B. subtilis*) transformed with recombinant bacteriophage DNA, plasmid DNA or cosmid DNA expression vectors containing differentially expressed or pathway gene protein coding sequences; yeast (e.g. Saccharomyces, Pichia) transformed with recombinant yeast expression vectors containing the differentially expressed or pathway gene protein coding sequences; insect cell systems infected with recombinant virus expression vectors (e.g., baculovirus) containing the differentially expressed or pathway gene protein coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing differentially expressed or pathway gene protein coding sequences; or mammalian cell systems (e.g. COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the differentially expressed or pathway gene protein being expressed. For example, when a large quantity of such a protein is to be produced, for the generation of antibodies or to screen peptide libraries, for example, vectors which direct the expression of high levels of fusion protein products that are readily purified may be desirable. Such vectors include, but are not limited to, the *E. coli* expression vector pUR278 (Ruther et al., 1983, *EMBO J.* 2:1791), in which the differentially expressed or pathway gene protein coding sequence may be ligated individually into the vector in frame with the lac Z coding region so that a fusion protein is produced; pIN vectors (Inouye & Inouye, 1985, Nucleic Acids Res. 13:3101–3109; Van Heeke & Schuster, 1989, J. Biol. Chem. 264:5503–5509); and the like. pGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the cloned target gene protein can be released from the GST moiety.

In a preferred embodiment, full length cDNA sequences are appended with in-frame Bam HI sites at the amino terminus and Eco RI sites at the carboxyl terminus using standard PCR methodologies (Innis et al., 1990, supra) and ligated into the pGEX-2TK vector (Pharmacia, Uppsala, Sweden). The resulting cDNA construct contains a kinase recognition site at the amino terminus for radioactive labelling and glutathione S-transferase sequences at the carboxyl terminus for affinity purification (Nilsson, et al., 1985, *EMBO J.* 4: 1075; Zabeau and Stanley, 1982, *EMBO J.* 1: 1217.

In an insect system, *Autographa californica* nuclear polyhedrosis virus (AcNPV) is used as a vector to express foreign genes. The virus grows in *Spodoptera frugiperda* cells. The differentially expressed or pathway gene coding sequence may be cloned individually into non-essential regions (for example the polyhedrin gene) of the virus and placed under control of an AcNPV promoter (for example the polyhedrin promoter). Successful insertion of differentially expressed or pathway gene coding sequence will result in inactivation of the polyhedrin gene and production of non-occluded recombinant virus (i.e., virus lacking the proteinaceous coat coded for by the polyhedrin gene). These recombinant viruses are then used to infect Spodoptera frugiperda cells in which the inserted gene is expressed. (E.g., see Smith et al., 1983, J. Virol. 46: 584; Smith, U.S. Pat. No. 4,215,051).

In mammalian host cells, a number of viral-based expression systems may be utilized. In cases where an adenovirus is used as an expression vector, the differentially expressed or pathway gene coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing differentially expressed or pathway gene protein in infected hosts. (E.g., See Logan & Shenk, 1984, Proc. Natl. Acad. Sci. USA 81:3655–3659). Specific initiation signals may also be required for efficient translation of inserted differentially expressed or pathway gene coding sequences. These signals include the ATG initiation codon and adjacent sequences. In cases where an entire differentially expressed or pathway gene, including its own initiation codon and adjacent sequences, is inserted into the appropriate expression vector, no additional translational control signals may be needed. However, in cases where only a portion of the differentially expressed or pathway gene coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., 1987, Methods in Enzymol. 153:516–544).

In a preferred embodiment, cDNA sequences encoding the full-length open reading frames are ligated into pCMVβ replacing the β-galactosidase gene such that cDNA expression is driven by the CMV promoter (Alam, 1990, Anal.

Biochem. 188: 245–254; MacGregor & Caskey, 1989, Nucl. Acids Res. 17: 2365; Norton & Corrin, 1985, Mol. Cell. Biol. 5: 281).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERO, BHK, HeLa, COS, MDCK, 293, 3T3, W138, etc.

For long-term, high-yield production of recombinant proteins, stable expression is preferred. For example, cell lines which stably express the differentially expressed or pathway gene protein may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1–2 days in an enriched media, and then are switched to a selective media The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the differentially expressed or pathway gene protein. Such engineered cell lines may be particularly useful in screening and evaluation of compounds that affect the endogenous activity of the differentially expressed or pathway gene protein.

A number of selection systems may be used, including but not limited to the herpes simplex virus thymidine kinase (Wigler, et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy, et al., 1980, Cell 22:817) genes can be employed in tk$^-$, hgprt$^-$ or aprt$^-$ cells, respectively. Also, antimetabolite resistance can be used as the basis of selection for dhfr, which confers resistance to methotrexate (Wigler, et al., 1980, Natl. Acad. Sci. USA 77:3567; O'Hare, et al., 1981, Proc. Natl. Acad. Sci. USA 78:1527); gpt. which confers resistance to mycophenolic acid (Mulligan & Berg, 1981, Proc. Natl. Acad. Sci. USA 78:2072); neo, which confers resistance to the aminoglycoside G-418 (Colberre-Garapin, et al., 1981, J. Mol. Biol. 150:1); and hygro, which confers resistance to hygromycin (Santerre, et al., 1984, Gene 30:147) genes.

An alternative fusion protein system allows for the ready purification of non-denatured fusion proteins expressed in human cell lines (Janknecht, et al., 1991, Proc. Natl. Acad. Sci. USA 88: 8972–8976). In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto Ni$^{2+}$ nitriloacetic acid-agarose columns and histidine-tagged proteins are selectively eluted with imidazole-containing buffers.

When used as a component in assay systems such as those described, below, in Section 5.5, the differentially expressed or pathway gene protein may be labeled, either directly or indirectly, to facilitate detection of a complex formed between the differentially expressed or pathway gene protein and a test substance. Any of a variety of suitable labeling systems may be used including but not limited to radioisotopes such as $^{125}$I; enzyme labelling systems that generate a detectable colorimetric signal or light when exposed to substrate; and fluorescent labels.

Where recombinant DNA technology is used to produce the differentially expressed or pathway gene protein for such assay systems, it may be advantageous to engineer fusion proteins that can facilitate labeling, immobilization and/or detection.

Indirect labeling involves the use of a protein, such as a labeled antibody, which specifically binds to either a differentially expressed or pathway gene product. Such antibodies include but are not limited to polyclonal, monoclonal, chimeric, single chain, Fab fragments and fragments produced by an Fab expression library.

5.4.3. Differentially Expressed or Pathway Gene Product Antibodies

Described herein are methods for the production of antibodies capable of specifically recognizing one or more differentially expressed or pathway gene epitopes. Such antibodies may include, but are not limited to polyclonal antibodies, monoclonal antibodies (mAbs), humanized or chimeric antibodies, single chain antibodies, Fab fragments, F(ab')$_2$ fragments, fragments produced by a Fab expression library, anti-idiotypic (anti-Id) antibodies, and epitope-binding fragments of any of the above. Such antibodies may be used, for example, in the detection of a fingerprint, target, or pathway gene in a biological sample, or, alternatively, as a method for the inhibition of abnormal target gene activity. Thus, such antibodies may be utilized as part of cardiovascular disease treatment methods, and/or may be used as part of diagnostic techniques whereby patients may be tested for abnormal levels of fingerprint, target, or pathway gene proteins, or for the presence of abnormal forms of the such proteins.

For the production of antibodies to a differentially expressed or pathway gene, various host animals may be immunized by injection with a differentially expressed or pathway gene protein, or a portion thereof. Such host animals may include but are not limited to rabbits, mice, and rats, to name but a few. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*.

In a preferred embodiment, peptide sequences corresponding to amino sequences of target gene products were selected and submitted to Research Genetics (Huntsville, AL) for synthesis and antibody production. Peptides were modified as described (Tam, J. P., 1988, Proc. Natl. Acad. Sci. USA 85: 5409–5413; Tam, J. P., and Zavala, F., 1989, J. Immunol. Methods 124: 53–61; Tam, J. P., and Lu, Y. A., 1989, Proc. Natl. Acad. Sci. USA 86: 9084–9088), emulsified in an equal volume of Freund's adjuvant and injected into rabbits at 3 to 4 subcutaneous dorsal sites for a total volume of 1.0 ml (0.5 mg peptide) per immunization. The animals were boosted after 2 and 6 weeks and bled at weeks 4, 8, and 10. The blood was allowed to clot and serum was collected by centrifugation. The generation of polyclonal antibodies against the fchd545 gene product is described in detail in the example in Section 10, below.

Polyclonal antibodies are heterogeneous populations of antibody molecules derived from the sera of animals immunized with an antigen, such as target gene product, or an antigenic functional derivative thereof. For the production of polyclonal antibodies, host animals such as those described above, may be immunized by injection with differentially expressed or pathway gene product supplemented with adjuvants as also described above.

Monoclonal antibodies, which are homogeneous populations of antibodies to a particular antigen, may be obtained by any technique which provides for the production of antibody molecules by continuous cell lines in culture. These include, but are not limited to the hybridoma technique of Kohler and Milstein, (1975, Nature 256:495–497; and U.S. Pat. No. 4,376,110), the human B-cell hybridoma technique (Kosbor et al., 1983, Immunology Today 4:72; Cole et al., 1983, Proc. Natl. Acad. Sci. USA 80:2026–2030), and the EBV-hybridoma technique (Cole et al., 1985, Monoclonal Antibodies And Cancer Therapy, Alan R. Liss, Inc., pp. 77–96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In addition, techniques developed for the production of "chimeric antibodies" (Morrison et al., 1984, Proc. Natl. Acad. Sci., 81:6851–6855; Neubergeretal., 1984, Nature, 312:604–608; Takeda et al., 1985, Nature, 314:452–454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region.

Alternatively, techniques described for the production of single chain antibodies (U.S. Pat. No. 4,946,778; Bird, 1988, Science 242:423–426; Huston et al., 1988, Proc. Natl. Acad. Sci. USA 85:5879–5883; and Ward et al., 1989, Nature 334:544–546) can be adapted to produce differentially expressed or pathway gene-single chain antibodies. Single chain antibodies are formed by linking the heavy and light chain fragments of the Fv region via an amino acid bridge, resulting in a single chain polypeptide.

Antibody fragments which recognize specific epitopes may be generated by known techniques. For example, such fragments include but are not limited to: the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed (Fuse et al., 1989, Science, 246:1275–1281) to allow rapid and easy identification of monoclonal Fab fragments with the desired specificity.

5.4.4. Cell- and Animal-based Model Systems

Described herein are cell- and animal-based systems which act as models for cardiovascular disease. These systems maybe used in a variety of applications. For example, the cell- and animal-based model systems may be used to further characterize differentially expressed and pathway genes, as described, above, in Section 5.3. Such further characterization may, for example, indicate that a differentially expressed gene is a target gene. Second, such assays may be utilized as part of screening strategies designed to identify compounds which are capable of ameliorating cardiovascular disease symptoms, as described, below, in Section 5.5.4. Thus, the animal- and cell-based models may be used to identify drugs, pharmaceuticals, therapies and interventions which may be effective in treating cardiovascular disease. In addition, as described in detail, below, in Section 5.7. 1, such animal models may be used to determine the $LD_{50}$ and the $ED_{50}$ in animal subjects, and such data can be used to determine the in vivo efficacy of potential cardiovascular disease treatments.

5.4.4.1. Animal-based Systems

Animal-based model systems of cardiovascular disease may include, but are not limited to, non-recombinant and engineered transgenic animals.

Non-recombinant animal models for cardiovascular disease may include, for example, genetic models. Such genetic cardiovascular disease models may include, for example, apoB or apoR deficient pigs (Rapacz, et al., 1986, Science 234:1573–1577) and Watanabe heritable hyperlipidemic (WHHL) rabbits (Kita et al., 1987, Proc. Natl. Acad. Sci USA 84: 5928–5931).

Non-recombinant, non-genetic animal models of atherosclerosis may include, for example, pig, rabbit, or rat models in which the animal has been exposed to either chemical wounding through dietary supplementation of LDL, or mechanical wounding through balloon catheter angioplasty, for example.

Additionally, animal models exhibiting cardiovascular disease symptoms may be engineered by utilizing, for example, target gene sequences such as those described, above, in Section 5.4.1, in conjunction with techniques for producing transgenic animals that are well known to those of skill in the art. For example, target gene sequences may be introduced into, and overexpressed in, the genome of the animal of interest, or, if endogenous target gene sequences are present, they may either be overexpressed or, alternatively, be disrupted in order to underexpress or inactivate target gene expression, such as described for the disruption of apoE in mice (Plump et al., 1992, Cell 71: 343–353).

In order to overexpress a target gene sequence, the coding portion of the target gene sequence may be ligated to a regulatory sequence which is capable of driving gene expression in the animal and cell type of interest. Such regulatory regions will be well known to those of skill in the art, and may be utilized in the absence of undue experimentation.

For underexpression of an endogenous target gene sequence, such a sequence may be isolated and engineered such that when reintroduced into the genome of the animal of interest, the endogenous target gene alleles will be inactivated. Preferably, the engineered target gene sequence is introduced via gene targeting such that the endogenous target sequence is disrupted upon integration of the engineered target gene sequence into the animal's genome. Gene targeting is discussed, below, in this Section.

Animals of any species, including, but not limited to, mice, rats, rabbits, guinea pigs, pigs, micro-pigs, goats, and non-human primates, e.g. baboons, monkeys, and chimpanzees may be used to generate cardiovascular disease animal models.

Any technique known in the art may be used to introduce a target gene transgene into animals to produce the founder lines of transgenic animals. Such techniques include, but are not limited to pronuclear microinjection (Hoppe, P. C. and Wagner, T. E., 1989, U.S. Pat. No. 4,873,191); retrovirus mediated gene transfer into germ lines (Van der Putten et al., 1985, Proc. Natl. Acad. Sci., USA 82:6148–6152); gene targeting in embryonic stem cells (Thompson et al., 1989, Cell 56:313–321); electroporation of embryos (Lo, 1983, Mol Cell. Biol. 3:1803–1814); and sperm-mediated gene transfer (Lavitrano et al., 1989, Cell 57:717–723); etc. For a review of such techniques, see Gordon, 1989, Transgenic Animals, Intl. Rev. Cytol. 115:171–25 229, which is incorporated by reference herein in its entirety.

The present invention provides for transgenic animals that carry the transgene in all their cells, as well as animals which carry the transgene in some, but not all their cells, i.e., mosaic animals. The transgene may be integrated as a single transgene or in concatamers, e.g., head-to-head tandems or head-to-tail tandems. The transgene may also be selectively introduced into and activated in a particular cell type by following, for example, the teaching of Lasko et al. (Lasko, M. et al., 1992, Proc. Natl. Acad. Sci. USA 89: 6232–6236). The regulatory sequences required for such a cell-type specific activation will depend upon the particular cell type of interest, and will be apparent to those of skill in the art. When it is desired that the target gene transgene be integrated into the chromosomal site of the endogenous target gene, gene targeting is preferred. Briefly, when such a technique is to be utilized, vectors containing some nucleotide sequences homologous to the endogenous target gene of interest are designed for the purpose of integrating, via homologous recombination with chromosomal sequences, into and disrupting the function of the nucleotide sequence of the endogenous target gene. The transgene may also be selectively introduced into a particular cell type, thus inactivating the endogenous gene of interest in only that cell type, by following, for example, the teaching of Gu et al. (Gu, et al., 1994, Science 265: 103–106). The regulatory sequences required for such a cell-type specific inactivation will depend upon the particular cell type of interest, and will be apparent to those of skill in the art. Recombinant methods for expressing target genes are described in Section 5.4.2, above.

Once transgenic animals have been generated, the expression of the recombinant target gene and protein may be assayed utilizing standard techniques. Initial screening may be accomplished by Southern blot analysis or PCR techniques to analyze animal tissues to assay whether integration of the transgene has taken place. The level of mRNA expression of the transgene in the tissues of the transgenic animals may also be assessed using techniques which include but are not limited to Northern blot analysis of tissue samples obtained from the animal, in situ hybridization analysis, and RT-PCR. Samples of target gene-expressing tissue, may also be evaluated immunocytochemically using antibodies specific for the target gene transgene gene product of interest.

The target gene transgenic animals that express target gene mRNA or target gene transgene peptide (detected immunocytochemically, using antibodies directed against the target gene product's epitopes) at easily detectable levels should then be further evaluated to identify those animals which display characteristic cardiovascular disease symptoms. Such symptoms may include, for example, increased prevalence and size of fatty streaks and/or cardiovascular disease plaques.

Additionally, specific cell types within the transgenic animals may be analyzed and assayed for cellular phenotypes characteristic of cardiovascular disease. In the case of monocytes, such phenotypes may include but are not limited to increases in rates of LDL uptake, adhesion to endothelial cells, transmigration, foam cell formation, fatty streak formation, and production of foam cell specific products. Cellular phenotype assays are discussed in detail in Section 5.4.4.2, below. Further, such cellular phenotypes may include a particular cell type's fingerprint pattern of expression as compared to known fingerprint expression profiles of the particular cell type in animals exhibiting cardiovascular disease symptoms. Fingerprint profiles are described in detail in Section 5.8.1, below. Such transgenic animals serve as suitable model systems for cardiovascular disease.

Once target gene transgenic founder animals are produced, they may be bred, inbred, outbred, or crossbred to produce colonies of the particular animal. Examples of such breeding strategies include but are not limited to: outbreeding of founder animals with more than one integration site in order to establish separate lines; inbreeding of separate lines in order to produce compound target gene transgenics that express the target gene transgene of interest at higher levels because of the effects of additive expression of each target gene transgene; crossing of heterozygous transgenic animals to produce animals homozygous for a given integration site in order both to augment expression and eliminate the possible need for screening of animals by DNA analysis; crossing of separate homozygous lines to produce compound heterozygous or homozygous lines; breeding animals to different inbred genetic backgrounds so as to examine effects of modifying alleles on expression of the target gene transgene and the development of cardiovascular disease symptoms. One such approach is to cross the target gene transgenic founder animals with a wild type strain to produce an F1 generation that exhibits cardiovascular disease symptoms. The F1 generation may then be inbred in order to develop a homozygous line, if it is found that homozygous target gene transgenic animals are viable.

The example presented in section 13, below, demonstrates the generation and phenotypic characterization of transgenic knockout homozygous rchd534 mutant mice. Such homozygous rchd534 mutant mice display characteristic cardiovascular disease symptoms comprising one or more of the following: (a) hyperplasia and/or thickening of at least one cardiac valve; (b) cardiac outflow tract development defects; (c) aortic ossification; (d) epicardial and/or endocardial vascular malformations; and (e) defects in the regulation of vascular tone. Such homozygous rchd534 mutant mice serve as useful models for the analysis and characterization of rchd534 protein involvement in development and homeostasis of the cardiovascular system and tissue-specific regulation of the TGF-β signaling pathways.

Such homozygous rchd534 mutant mice are useful as animal models for the analysis and characterization of rchd534 protein involvement in development and homeostasis of the cardiovascular system and tissue-specific regulation of the TGF-β signaling pathways. In particular, these mice are also useful models for studying human diseases and syndromes including, without limitation, vascular malformations attributable to hereditary Hemorrhagic Telangiectasia, advanced athereosclerosis and/or plaque rupture, cardiac calcification, allo/xenograft valvular calcifications, and sclero-calcific aortic valve disease.

The present invention also includes methods for generating a mammalian totipotent cell having at least one inactivated (non-functional) rchd534 allele, where the totipotent cell is derived from a mammalian species in which alleles for the rchd534 gene normally are present and functional. A "functional" allele is capable of being transcribed and translated to produce a polypeptide having an activity the same as or substantially similar to the rchd534 gene product. The methods include providing a plurality of cells characterized as totipotent cells of various mammalian species, introducing into the totipotent cells a nucleic acid construct effective for inactivating the rchd534 gene by insertion of a desired DNA sequence into an insertion site of the gene through homologous recombination, and then identifying a totipotent cell having at least one inactivated rchd534 allele.

As used herein, hyperplasia refers to an increase in the number of cells in a tissue or organ, excluding tumor formation, whereby the bulk of the part or organ may be increased.

As used herein, calcification refers to a process in which tissue or non-cellular material in the body becomes hardened as the result of precipitates or larger deposits of insoluble salts calcium (and also magnesium), especially calcium carbonate and phosphate (hydroxyapatite) normally occurring only in the formation of bone and teeth. The term calcification is synonymous with calcareous infiltration.

As used herein, ossification refers to either the formation of bone or a change of tissue or non-cellular material of the body into bone.

5.4.4.2. Cell-based Assays

Cells that contain and express target gene sequences which encode target gene protein, and, further, exhibit cellular phenotypes associated with cardiovascular disease, maybe utilized to identify compounds that exhibit anti-cardiovascular disease activity.

Such cells may include non-recombinant monocyte cell lines, such as U937 (ATCC# CRL-1593), THP-1 (ATCC# TIB-202), and P388D1 (ATCC# TIB-63); endothelial cells such as HUVEC's and bovine aortic endothelial cells (BAEC's); as well as generic mammalian cell lines such as HeLa cells and COS cells, e.g., COS-7 (ATCC# CRL-165 1). Further, such cells may include recombinant, transgenic cell lines. For example, the cardiovascular disease animal models of the invention, discussed, above, in Section 5.4.4.1, may be used to generate cell lines, containing one or more cell types involved in cardiovascular disease, that can be used as cell culture models for this disorder. While primary cultures derived from the cardiovascular disease transgenic animals of the invention may be utilized, the generation of continuous cell lines is preferred. For examples of techniques which may be used to derive a continuous cell line from the transgenic animals, see Small et al., 1985, Mol. Cell Biol. 5:642–648.

Alternatively, cells of a cell type known to be involved in cardiovascular disease may be transfected with sequences capable of increasing or decreasing the amount of target gene expression within the cell. For example, target gene sequences may be introduced into, and overexpressed in, the genome of the cell of interest, or, if endogenous target gene sequences are present, they may be either overexpressed or, alternatively disrupted in order to underexpress or inactivate target gene expression.

In order to overexpress a target gene sequence, the coding portion of the target gene sequence may be ligated to a regulatory sequence which is capable of driving gene expression in the cell type of interest. Such regulatory regions will be well known to those of skill in the art, and may be utilized in the absence of undue experimentation. Recombinant methods for expressing target genes are described in Section 5.4.2, above.

For underexpression of an endogenous target gene sequence, such a sequence may be isolated and engineered such that when reintroduced into the genome of the cell type of interest, the endogenous target gene alleles will be inactivated. Preferably, the engineered target gene sequence is introduced via gene targeting such that the endogenous target sequence is disrupted upon integration of the engineered target gene sequence into the cell's genome. Transfection of host cells with target genes is discussed, above, in Section 5.4.4.1.

Cells treated with compounds or transfected with target genes can be examined for phenotypes associated with cardiovascular disease. In the case of monocytes, such phenotypes include but are not limited to increases in rates of LDL uptake, adhesion to endothelial cells, transmigration, foam cell formation, fatty streak formation, and production by foam cells of growth factors such as bFGF, IGF-1, VEGF, IL-1, M-CSF, TGFβ, TGFα, TNFα, HB-EGF, DGF, IFN-γ, and GM-CSF. Transmigration rates, for example, may be measured using the in vitro system of Navab et al., described in Section 5.1.1.3, above, by quantifying the number of monocytes that migrate across the endothelial monolayer and into the collagen layer of the subendothelial space.

Similarly, HUVEC's can be treated with test compounds or transfected with genetically engineered target genes described in Section 5.4.2, above. The HUVEC's can then be examined for phenotypes associated with cardiovascular disease, including, but not limited to changes in cellular morphology, cell proliferation, cell migration, and mononuclear cell adhesion; or for the effects on production of other proteins involved in cardiovascular disease such as ICAM, VCAM, PDGF-β, and E-selectin.

Transfection of target gene sequence nucleic acid may be accomplished by utilizing standard techniques. See, for example, Ausubel, 1989, supra. Transfected cells should be evaluated for the presence of the recombinant target gene sequences, for expression and accumulation of target gene mRNA, and for the presence of recombinant target gene protein production. In instances wherein a decrease in target gene expression is desired, standard techniques may be used to demonstrate whether a decrease in endogenous target gene expression and/or in target gene product production is achieved.

5.5. Screening Assays for Compounds That Interact with the Target Gene Product and/or Modulate Target Gene Expression The following assays are designed to identify compounds that bind to target gene products, bind to other cellular or extracellular proteins that interact with a target gene product, and interfere with the interaction of the target gene product with other cellular or extracellular proteins. Such compounds can act as the basis for amelioration of such cardiovascular diseases as atherosclerosis, ischemia/reperfusion, hypertension, restenosis, and arterial inflammation by modulating the activity of the protein products of target genes. Such compounds may also act as the basis forth amelioration of fibroproliferative and oncogenic related disorders, including tumorigenesis and the vascularization of tumors. Such compounds may include, but are not limited to peptides, antibodies, or small organic or inorganic compounds. Methods for the identification of such compounds are described in Section 5.5.1, below. Such compounds may also include other cellular proteins. Methods for the identification of such cellular proteins are described, below, in Section 5.5.2.

Compounds identified via assays such as those described herein may be useful, for example, in elaborating the biological function of the target gene product, and for ameliorating cardiovascular disease. In instances whereby a cardiovascular disease condition results from an overall lower level of target gene expression and/or target gene product in a cell or tissue, compounds that interact with the target gene product may include compounds which accentuate or amplify the activity of the bound target gene protein. Such compounds would bring about an effective increase in the level of target gene product activity, thus ameliorating symptoms.

In some cases, a target gene observed to be up-regulated under disease conditions may be exerting a protective effect. Compounds that enhance the expression of such up-regulated genes, or the activity of their gene products, would also ameliorate disease symptoms, especially in individuals whose target gene is not normally up-regulated.

In other instances mutations within the target gene may cause aberrant types or excessive amounts of target gene proteins to be made which have a deleterious effect that leads to cardiovascular disease. Similarly, physiological conditions may cause an excessive increase in target gene expression leading to cardiovascular disease. In such cases, compounds that bind target gene protein may be identified that inhibit the activity of the bound target gene protein. Assays for testing the effectiveness of compounds, identified by, for example, techniques such as those described in this Section are discussed, below, in Section 5.5.4.

5.5.1. In Vitro Screening Assays for Compounds That Bind to the Target Gene Product In vitro systems may be designed to identify compounds capable of binding the target gene of the invention. Such compounds may include, but are not limited to, peptides made of D-and/or L-configuration amino acids (in, for example, the form of random peptide libraries; see e.g., Lam, K. S. et al., 1991, Nature 354:82–84), phosphopeptides (in, for example, the form of random or partially degenerate, directed phosphopeptide libraries; see, e.g., Songyang, Z. et al., 1993, Cell 72:767–778), antibodies, and small organic or inorganic molecules. Compounds identified may be useful, for example, in modulating the activity of target gene proteins, preferably mutant target gene proteins, may be useful in elaborating the biological function of the target gene protein, may be utilized in screens for identifying compounds that disrupt normal target gene interactions, or may in themselves disrupt such interactions. For instance, the example in Section 12, below, describes the interaction between the rchd534 protein and the fchd540 protein. Compounds that disrupt the interaction between these two proteins may be useful in the treatment of cardiovascular disease.

The principle of the assays used to identify compounds that bind to the target gene protein involves preparing a reaction mixture of the target gene protein and the test compound under conditions and for a time sufficient to allow the two components to interact and bind, thus forming a complex which can be removed and/or detected in the reaction mixture. These assays can be conducted in a variety of ways. For example, one method to conduct such an assay would involve anchoring the target gene or the test substance onto a solid phase and detecting target gene/test substance complexes anchored on the solid phase at the end of the reaction. In one embodiment of such a method, the target gene protein may be anchored onto a solid surface, and the test compound, which is not anchored, may be labeled, either directly or indirectly.

In practice, microtitre plates are conveniently utilized. The anchored component may be immobilized by non-covalent or covalent attachments. Non-covalent attachment may be accomplished simply by coating the solid surface with a solution of the protein and drying. Alternatively, an immobilized antibody, preferably a monoclonal antibody, specific for the protein may be used to anchor the protein to the solid surface. The surfaces may be prepared in advance and stored.

In order to conduct the assay, the nonimmobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously nonimmobilized component is pre-labeled, the detection of label immobilized on the surface indicates that complexes were formed. Where the previously nonimmobilized component is not pre-labeled, an indirect label can be used to detect complexes anchored on the surface; e.g., using a labeled antibody specific for the previously nonimmobilized component (the antibody, in turn, may be directly labeled or indirectly labeled with a labeled anti-Ig antibody).

Alternatively, a reaction can be conducted in a liquid phase, the reaction products separated from unreacted components, and complexes detected; e.g., using an immobilized antibody specific for target gene product or the test compound to anchor any complexes formed in solution, and a labeled antibody specific for the other component of the possible complex to detect anchored complexes.

Compounds that are shown to bind to a particular target gene product through one of the methods described above can be further tested for their ability to elicit a biochemical response from the target gene protein. A particular embodiment is described herein for receptor proteins involved in signal transduction. Compounds that interact with a target gene product receptor domain, can be screened for their ability to function as ligands, i.e., to bind to the receptor protein in a manner that triggers the signal transduction pathway. Useful receptor fragments or analogs in the invention are those which interact with ligand. The receptor component can be assayed functionally, i.e., for its ability to bind ligand and mobilize $Ca^{++}$ (see below). These assays include, as components, ligand and a recombinant target gene product (or a suitable fragment or analog) configured to permit detection of binding.

For example, and not by way of limitation, a recombinant receptor may be used to screen for ligands by its ability to mediate ligand-dependent mobilization of calcium. Cells, preferably myeloma cells or Xenopus oocytes, transfected with a target gene expression vector (constructed according to the methods described in Section 5.4.2, above) are loaded with FURA-2 or INDO-1 by standard techniques. Mobilization of $Ca^{2+}$ induced by ligand is measured by fluorescence spectroscopy as previously described (Grynkiewicz et al., 1985, *J. Biol. Chem.* 260:3440). Ligands that react with the target gene product receptor domain, therefore, can be identified by their ability to produce a fluorescent signal. Their receptor binding activities can be quantified and compared by measuring the level of fluorescence produced over background. Identification of ligand, and measuring the activity of the ligand-receptor complex, leads to the identification of antagonists of this interaction, as described in Section 5.5.3, below. Such antagonists are useful in the treatment of cardiovascular disease.

5.5.2. Assays for Cellular or Extracellular Proteins that Interact with the Target Gene Product Any method suitable for detecting protein-protein interactions may be employed for identifying novel target protein-cellular or extracellular protein interactions. These methods are outlined in Section 5.2., supra, for the identification of pathway genes, and may be utilized herein with respect to the identification of proteins which interact with identified target proteins. In such a case, the target gene serves as the known "bait" gene.

The example presented in Section 12, below, demonstrates the use of this method to detect the interaction between the rchd534 protein and the fchd540 protein, which both had been identified as target proteins.

5.5.3. Assays for Compounds that Interfere with Interaction Between Target Gene Product and Other Compounds The target gene proteins of the invention may, in vivo, interact with one or more cellular or extracellular proteins. Such proteins may include, but are not limited to, those proteins identified via methods such as those described, above, in Section 5.5.2. For the purposes of this discussion, target gene products and such cellular and extracellular proteins are referred to herein as "binding partners". Compounds that disrupt such interactions may be useful in regulating the activity of the target gene proteins, especially mutant target gene proteins. Such compounds may include, but are not limited to molecules such as antibodies, peptides, and the like described in Section 5.5.1. above.

The basic principle of the assay systems used to identify compounds that interfere with the interaction between the target gene protein, and its cellular or extracellular protein binding partner or partners involves preparing a reaction mixture containing the target gene protein and the binding partner under conditions and for a time sufficient to allow the two proteins to interact and bind, thus forming a complex. In order to test a compound for inhibitory activity, the reaction mixture is prepared in the presence and absence of the test compound. The test compound may be initially included in the reaction mixture or may be added at a time subsequent to the addition of target gene and its cellular or extracellular binding partner. Control reaction mixtures are incubated without the test compound or with a placebo. The formation of any complexes between the target gene protein and the cellular or extracellular binding partner is then detected. The formation of a complex in the control reaction, but not in the reaction mixture containing the test compound, indicates that the compound interferes with the interaction of the target gene protein and the interactive binding partner protein. Additionally, complex formation within reaction mixtures containing the test compound and a normal target gene protein may also be compared to complex formation within reaction mixtures containing the test compound and mutant target gene protein. This comparison may be important in those cases wherein it is desirable to identify compounds that disrupt interactions of mutant but not normal target gene proteins.

The assay for compounds that interfere with the interaction of the binding partners can be conducted in a heterogeneous or homogeneous format. Heterogeneous assays involve anchoring one of the binding partners onto a solid phase and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the binding partners, e.g., by competition, can be identified by conducting the reaction in the presence of the test substance; i.e., by adding the test substance to the reaction mixture prior to or simultaneously with the target gene protein and interactive cellular or extracellular protein.

Alternatively, test compounds that disrupt preformed complexes, e.g. compounds with higher binding constants that displace one of the binding partners from the complex, can be tested by adding the test compound to the reaction mixture after complexes have been formed. The various formats are described briefly below.

In a heterogeneous assay system, either the target gene protein or the interactive cellular or extracellular binding partner protein, is anchored onto a solid surface, and its binding partner, which is not anchored, is labeled, either directly or indirectly. In practice, microtitre plates are conveniently utilized. The anchored species may be immobilized by non-covalent or covalent attachments. Non-covalent attachment may be accomplished simply by coating the solid surface with a solution of the protein and drying. Alternatively, an immobilized antibody specific for the protein may be used to anchor the protein to the solid surface. The surfaces may be prepared in advance and stored.

In order to conduct the assay, the binding partner of the immobilized species is exposed to the coated surface with or without the test compound. After the reaction is complete, unreacted components are removed (e.g., by washing) and any complexes formed will remain immobilized on the solid surface. The detection of complexes anchored on the solid surface can be accomplished in a number of ways. Where the binding partner was pre-labeled, the detection of label immobilized on the surface indicates that complexes were formed. Where the binding partner is not pre-labeled, an indirect label can be used to detect complexes anchored on the surface; e.g., using a labeled antibody specific for the binding partner (the antibody, in turn, may be directly labeled or indirectly labeled with a labeled anti-Ig antibody). Depending upon the order of addition of reaction components, test compounds which inhibit complex formation or which disrupt preformed complexes can be detected.

Alternatively, the reaction can be conducted in a liquid phase in the presence or absence of the test compound, the reaction products separated from unreacted components, and complexes detected; e.g., using an immobilized antibody specific for one binding partner to anchor any complexes formed in solution, and a labeled antibody specific for the other binding partner to detect anchored complexes. Again, depending upon the order of addition of reactants to the liquid phase, test compounds which inhibit complex or which disrupt preformed complexes can be identified.

In an alternate embodiment of the invention, a homogeneous assay can be used. In this approach, a preformed complex of the target gene protein and the interactive cellular or extracellular protein is prepared in which one of the binding partners is labeled, but the signal generated by the label is quenched due to complex formation (see, e.g., U.S. Pat. No. 4,109,496 by Rubenstein which utilizes this approach for immunoassays). The addition of a test substance that competes with and displaces one of the binding partners from the preformed complex will result in the generation of a signal above background. In this way, test substances which disrupt target gene protein-cellular or extracellular protein interaction can be identified.

In a particular embodiment, the target gene protein can be prepared for immobilization using recombinant DNA techniques described in Section 5.4.2, supra. For example, the target gene coding region can be fused to a glutathione-S-transferase (GST) gene, using a fusion vector such as pGEX-5X-1, in such a manner that its binding activity is maintained in the resulting fusion protein. The interactive cellular or extracellular protein can be purified and used to raise a monoclonal antibody, using methods routinely practiced in the art and described above, in Section 5.4.3. This antibody can be labeled with the radioactive isotope $^{125}$I, for example, by methods routinely practiced in the art. In a heterogeneous assay, e.g., the GST-target gene fusion protein can be anchored to glutathione-agarose beads. The interactive cellular or extracellular binding partner protein can then be added in the presence or absence of the test compound in a manner that allows interaction and binding to occur. At the end of the reaction period, unbound material can be washed away, and the labeled monoclonal antibody can be added to the system and allowed to bind to the complexed binding partners. The interaction between the target gene protein and the interactive cellular or extracellular binding partner protein can be detected by measuring the amount of radioactivity that remains associated with the glutathione-agarose beads. A successful inhibition of the interaction by the test compound will result in a decrease in measured radioactivity.

Alternatively, the GST-target gene fusion protein and the interactive cellular or extracellular binding partner protein can be mixed together in liquid in the absence of the solid glutathione-agarose beads. The test compound can be added either during or after the binding partners are allowed to interact. This mixture can then be added to the glutathione-agarose beads and unbound material is washed away. Again the extent of inhibition of the binding partner interaction can be detected by adding the labeled antibody and measuring the radioactivity associated with the beads.

In another embodiment of the invention, these same techniques can be employed using peptide fragments that correspond to the binding domains of the target gene protein and the interactive cellular or extracellular protein, respectively, in place of one or both of the fall length proteins. Any number of methods routinely practiced in the art can be used to identify and isolate the protein's binding site. These methods include, but are not limited to, mutagenesis of one of the genes encoding the proteins and screening for disruption of binding in a co-immunoprecipitation assay. Compensating mutations in the target gene can be selected. Sequence analysis of the genes encoding the respective proteins will reveal the mutations that correspond to the region of the protein involved in interactive binding. Alternatively, one protein can be anchored to a solid surface using methods described in this Section above, and allowed to interact with and bind to its labeled binding partner, which has been treated with a proteolytic enzyme, such as trypsin. After washing, a short, labeled peptide comprising the binding domain may remain associated with the solid material, which can be isolated and identified by amino acid sequencing. Also, once the gene coding for the for the cellular or extracellular protein is obtained, short gene segments can be engineered to express peptide fragments of the protein, which can then be tested for binding activity and purified or synthesized.

For example, and not by way of limitation, target gene can be anchored to a solid material as described above in this Section by making a GST-target gene fusion protein and allowing it to bind to glutathione agarose beads. The interactive cellular or extracellular binding partner protein can be labeled with a radioactive isotope, such as $^{35}$S, and cleaved with a proteolytic enzyme such as trypsin. Cleavage products can then be added to the anchored GST-target gene fusion protein and allowed to bind. After washing away unbound peptides, labeled bound material, representing the cellular or extracellular binding partner protein binding domain, can be eluted, purified, and analyzed for amino acid sequence by techniques well known in the art; e.g., using the Edman degradation procedure (see e.g., Creighton, 1983, Proteins: Structures and Molecular Principles, W. H. Freeman & Co., N.Y., pp. 34–49). Peptides so identified can be produced, using techniques well known in the art, either synthetically (see e.g., Creighton, 1983, supra at pp. 50–60) or, if the gene has already been isolated, by using recombinant DNA technology, as described in Section 5.4.2, supra.

A particular embodiment of the invention features a method of screening candidate compounds for their ability to antagonize the interaction between ligand and the receptor domain of a target gene product. The method involves: a) mixing a candidate antagonist compound with a first compound which includes a recombinant target gene product comprising a receptor domain (or ligand-binding fragment or analog) on the one hand and with a second compound which includes ligand on the other hand; b) determining whether the first and second compounds bind; and c) identifying antagonistic compounds as those which interfere with the binding of the first compound to the second compound and/or which reduce the ligand-mediated release of intracellular $C^{++}$.

By an "antagonist" is meant a molecule which inhibits a particular activity, in this case, the ability of ligand to interact with a target gene product receptor domain and/or to trigger the biological events resulting from such an interaction (e.g., release of intracellular Ca). Preferred therapeutics include antagonists, e.g., peptide fragments (particularly, fragments derived from the N-terminal extracellular domain), antibodies Particularly, antibodies which recognize and bind the N-terminal extracellular domain), or drugs, which block ligand or target gene product function by interfering with the ligand-receptor interaction.

Because the receptor component of the target gene product can be produced by recombinant techniques and because candidate antagonists may be screened in vitro, the instant invention provides a simple and rapid approach to the identification of useful therapeutics.

Specific receptor fragments of interest include any portions of the target gene products that are capable of interaction with ligand, for example, all or part of the N-terminal extracellular domain. Such portions include the transmembrane segments and portions of the receptor deduced to be extracellular. Such fragments may be useful as antagonists (as described above), and are also useful as immunogens for producing antibodies which neutralize the activity of the target gene product in vivo (e.g., by interfering with the interaction between the receptor and ligand; see below). Extracellular regions may be identified by comparison with related proteins of similar structure, useful regions are those exhibiting homology to the extracellular domains of well-characterized members of the family.

Alternatively, from the primary amino acid sequence, the secondary protein structure and, therefore, the extracellular domain regions may be deduced semi-empirically using a hydrophobicity/hydrophilicity calculation such as the Chou-Fasman method (see, e.g., Chou and Fasman, *Ann. Rev. Biochem.* 47:251, 1978). Hydrophilic domains, particularly ones surrounded by hydrophobic stretches (e.g., transmembrane domains) present themselves as strong candidates for extracellular domains. Finally, extracellular domains may be identified experimentally using standard enzymatic digest analysis, e.g., tryptic digest analysis.

Candidate fragments (e.g., all or part of the transmembrane segments or any extracellular fragment) are tested for interaction with ligand by the assays described herein (e.g., the assay described above). Such fragments are also tested for their ability to antagonize the interaction between ligand and its endogenous receptor using the assays described herein. Analogs of useful receptor fragments (as described above) may also be produced and tested for efficacy as screening components or antagonists (using the assays described herein); such analogs are also considered to be useful in the invention.

Of particular interest are receptor fragments encompassing the extracellular main-terminal domain (or a ligand binding fragment thereof). Also of interest are the target gene product extracellular loops. Peptide fragments derived from these extracellular loops may also be used as antagonists, particularly if the loops cooperate with the amino-terminal domain to facilitate ligand binding. Alternatively, such loops and extracellular N-terminal domain (as well as the full length target gene product) provide immunogens for producing anti-target gene product antibodies.

Binding of ligand to its receptor may be assayed by any of the methods described above in Section 5.5.1. Preferably, cells expressing recombinant target gene product (or a suitable target gene product fragment or analog) are immobilized on a solid substrate (e.g., the wall of a microtitre plate or a column) and reacted with detectably-labelled ligand (as described above). Binding is assayed by the detection label in association with the receptor component (and, therefore, in association with the solid substrate). Binding of labelled ligand to receptor-bearing cells is used as a "control" against which antagonist assays are measured. The antagonist assays involve incubation of the target gene product-bearing cells with an appropriate amount of candidate antagonist. To this mix, an equivalent amount to labelled ligand is added. An antagonist useful in the invention specifically interferes with labelled ligand binding to the immobilized receptor-expressing cells.

An antagonist is then tested for its ability to interfere with ligand function, i.e., to specifically interfere with labelled ligand binding without resulting in signal transduction normally mediated by the receptor. To test this using a functional assay, stably transfected cell lines containing the target gene product can be produced as described herein and reporter compounds such as the calcium binding agent, FURA-2, loaded into the cytoplasm by standard techniques. Stimulation of the heterologous target gene product with ligand or another agonist leads to intracellular calcium release and the concomitant fluorescence of the calcium-FURA-2 complex. This provides a convenient means for measuring agonist activity. Inclusion of potential antagonists along with ligand allows for the screening and identification of authentic receptor antagonists as those which effectively block ligand binding without producing fluorescence (i.e., without causing the mobilization of intracellular $Ca^{++}$). Such an antagonist may be expected to be a useful therapeutic agent for cardiovascular disorders.

Appropriate candidate antagonists include target gene product fragments, particularly fragments containing a ligand-binding portion adjacent to or including one or more transmembrane segments or an extracellular domain of the receptor (described above); such fragments would preferably including five or more amino acids. Other candidate antagonists include analogs of ligand and other peptides as well as non-peptide compounds and anti-target gene product antibodies designed or derived from analysis of the receptor.

5.5.3. Assays for Amelioration of Cardiovascular Disease Symptoms

Any of the binding compounds, including but not limited to compounds such as those identified in the foregoing assay systems, may be tested for the ability to ameliorate cardiovascular disease symptoms. Cell-based and animal model-based assays for the identification of compounds exhibiting such an ability to ameliorate cardiovascular disease symptoms are described below.

First, cell-based systems such as those described, above, in Section 5.4.4.2., may be used to identify compounds which may act to ameliorate cardiovascular disease symptoms. For example, such cell systems may be exposed to a compound, suspected of exhibiting an ability to ameliorate cardiovascular disease symptoms, at a sufficient concentration and for a time sufficient to elicit such an amelioration of cardiovascular disease symptoms in the exposed cells. After exposure, the cells are examined to determine whether one or more of the cardiovascular disease cellular phenotypes has been altered to resemble a more normal or more wild type, non-cardiovascular disease phenotype. For example, and not by way of limitation, in the case of monocytes, such more normal phenotypes may include but are not limited to decreased rates of LDL uptake, adhesion to endothelial cells, transmigration, foam cell formation, fatty streak formation, and production by foam cells of growth factors such as bFGF, IGF-1, VEGF, IL-1, M-CSF, TGFβ, TGFα, TNFα, HB-EGF, PDGF, IFN-γ, and GM-CSF. Transmigration rates, for example, may be measured using the in vitro system of Navab et al., described in Section 5.1.1.3, above, by quantifying the number of monocytes that migrate across the endothelial monolayer and into the collagen layer of the subendothelial space.

In addition, animal-based cardiovascular disease systems, such as those described, above, in Section 5.4.4.1, may be used to identify compounds capable of ameliorating cardiovascular disease symptoms. Such animal models may be used as test substrates for the identification of drugs, pharmaceuticals, therapies, and interventions which may be effective in treating cardiovascular disease. For example, animal models may be exposed to a compound, suspected of exhibiting an ability to ameliorate cardiovascular disease symptoms, at a sufficient concentration and for a time sufficient to elicit such an amelioration of cardiovascular disease symptoms in the exposed animals. The response of the animals to the exposure may be monitored by assessing the reversal of disorders associated with cardiovascular disease, for example, by counting the number of atherosclerotic plaques and/or measuring their size before and after treatment.

Further, both cell-based systems and animal-based systems as described herein may be used to identify compounds which act to ameliorate symptoms of fibroproliferative and oncogenic related disorders, including tumorigenesis and the vascularization of tumors. Such cell-based and animal-based systems may be exposed to a compound, suspected of exhibiting an ability to ameliorate fibroproliferative disease symptoms, at a sufficient concentration and for a time sufficient to elicit such an amelioration of fibroproliferative disease symptoms in the exposed system. The response may be monitored by assessing the reversal of disorders associated with fibroproliferative disease, for example by measuring the size and growth of tumors or vascularization of tumors before and after treatment.

With regard to intervention, any treatments which reverse any aspect of cardiovascular disease symptoms should be considered as candidates for human cardiovascular disease therapeutic intervention. Dosages of test agents maybe determined by deriving dose-response curves, as discussed in Section 5.7.1, below.

Additionally, gene expression patterns may be utilized to assess the ability of a compound to ameliorate cardiovascular disease symptoms. For example, the expression pattern of one or more fingerprint genes may form part of a "fingerprint profile" which may be then be used in such an assessment. "Fingerprint profile", as used herein, refers to the pattern of mRNA expression obtained for a given tissue or cell type under a given set of conditions. Such conditions may include, but are not limited to, atherosclerosis, ischemia/reperfusion, hypertension, restenosis, and arterial inflammation, including any of the control or experimental conditions described in the paradigms of Section 5.1.1, above. Fingerprint profiles may be generated, for example, by utilizing a differential display procedure, as discussed, above, in Section 5.1.2, Northern analysis and/or RT-PCR. Any of the gene sequences described, above, in Section 5.4.1. may be used as probes and/or PCR primers for the generation and corroboration of such fingerprint profiles.

Fingerprint profiles maybe characterized for known states, either cardiovascular disease or normal, within the cell- and/or animal-based model systems. Subsequently, these known fingerprint profiles may be compared to ascertain the effect a test compound has to modify such fingerprint profiles, and to cause the profile to more closely resemble that of a more desirable fingerprint.

For example, administration of a compound may cause the fingerprint profile of a cardiovascular disease model system to more closely resemble the control system. Administration of a compound may, alternatively, cause the fingerprint profile of a control system to begin to mimic a cardiovascular disease state. Such a compound may, for example, be used in further characterizing the compound of interest, or may be used in the generation of additional animal models.

5.5.4. Monitoring of Effects During Clinical Trials

Monitoring the influence of compounds on cardiovascular disease states maybe applied not only in basic drug screening, but also in clinical trials. In such clinical trials, the expression of a panel of genes that have been discovered in one of the paradigms described in Section 5.1.1.1 through 5.1.1.6 may be used as a "read out" of a particular drug's effect on a cardiovascular disease state.

For example, and not by way of limitation, Paradigm A provides for the identification of fingerprint genes that are up-regulated in monocytes treated with oxidized LDL. Thus, to study the effect of anti-oxidant drugs, for example, in a clinical trial, blood may be drawn from patients before and at different stages during treatment with such a drug. Their monocytes may then be isolated and RNA prepared and analyzed by differential display as described in Sections 6.1.1 and 6.1.2. The levels of expression of these fingerprint genes maybe quantified by Northern blot analysis or RT-PCR, as described in Section 6.1.2, or by one of the methods described in Section 5.8.1, or alternatively by measuring the amount of protein produced, by one of the methods described in Section 5.8.2. In this way, the fingerprint profiles may serve as surrogate markers indicative of the physiological response of monocytes that have taken up oxidized LDL. Accordingly, this response state may be determined before, and at various points during, drug treatment. This method is described in further detail in the example in Section 8, below. Specifically, the up-regulation of fchd602 and fchd605 under treatment with oxidized LDL provides a fingerprint profile for monocytes under oxidative stress. The fchd602 and fchd605 genes can serve, therefore, as surrogate markers during clinical treatment of cardiovascular disease. Accordingly, the influence of anti-oxidant drugs on oxidative potential is measured by recording the differential display of fchd602 and fchd605 in the monocytes of patients undergoing clinical treatment.

5.5.5. Assays for Compounds that Modulate Expression of Target Genes

Compounds and other substances that modulate expression of target genes can be screened using in vitro cellular systems. In a manner analogous to the monitoring of compounds clinical samples described in Section 5.5.5, above, a sample of cells, such as a tissue culture is exposed to a test substance. Appropriate tissue culture cells include, but are not limited to, human umbilical vein endothelial cells (HUVECs), bovine aortic endothelial cells (BAECs), and 293 cells (embryonic human kidney cells). The RNA is then extracted from the cells. The level of transcription of a specific target gene can be detected using, for example, standard RT-PCR amplification techniques and/or Northern analysis (as described in the example in Section 6.1.2, below). Alternatively, the level of target protein production can be assayed by using antibodies that detect the target gene protein, as described in Section 5.5.1, above. The level of expression is compared to a control cell sample which was not exposed to the test substance.

Compounds that can be screened for modulation of expression of the target gene include, but are not limited to, small inorganic or organic molecules, peptides, such as peptide hormones analogs, steroid hormones, analogs of such hormones, and other proteins. Compounds that downregulate expression include, but are not limited to, oligonucleotides that are complementary to the 5'-end of the mRNA of the target gene and inhibit transcription by forming triple helix structures, and ribozymes or antisense molecules which inhibit translation of the target gene mRNA. Techniques and strategies for designing such downregulating test compounds are described in detail in Section 5.6, below.

5.6. Compounds of Methods for Treatment of Cardiovascular and Fibroproliferative Disease Described below are methods and compositions whereby cardiovascular disease symptoms may be ameliorated. The methods and compositions described below may also be applied for the amelioration of symptoms associated with fibroproliferative and oncogenic disorders, but as a way of example will be discussed in the subsections below in terms of cardiovascular disease disorders. Certain cardiovascular diseases are brought about, at least in part, by an excessive level of gene product, or by the presence of a gene product exhibiting an abnormal or excessive activity. As such, the reduction in the level and/or activity of such gene products would bring about the amelioration of cardiovascular disease symptoms.

Techniques for the reduction of target gene expression levels or target gene product activity levels are discussed in Section 5.6.1, below.

Alternatively, certain other cardiovascular diseases are brought about, at least in part, by the absence or reduction of the level of gene expression, or a reduction in the level of a gene products activity. As such, an increase in the level of gene expression and/or the activity of such gene products would bring about the amelioration of cardiovascular disease symptoms.

In some cases, the up-regulation of a gene in a disease state reflects a protective role for that gene product in responding to the disease condition. Enhancement of such a target gene's expression, or the activity of the target gene product, will reinforce the protective effect it exerts. Some cardiovascular disease states may result from an abnormally low level of activity of such a protective gene. In these cases also, an increase in the level of gene expression and/or the activity of such gene products would bring about the amelioration of cardiovascular disease symptoms. Techniques for increasing target gene expression levels or target gene product activity levels are discussed in Section 5.6.2, below.

5.6.1. Compounds that Inhibit Expression, Synthesis or Activity of Mutant Target Gene Activity As discussed above, target genes involved in cardiovascular disease disorders can cause such disorders via an increased level of target gene activity. As summarized in Table 1, above, and detailed in the examples in Sections 6 and 7, below, a number of genes have been demonstrated to be up-regulated in monocytes and endothelial cells under disease conditions. Specifically, fchd602 and fchd605 are each up-regulated in monocytes treated with oxidized LDL. Furthermore, fchd540 is up-regulated in endothelial cells subjected to shear stress. In some cases, such up-regulation may have a causative or exacerbating effect on the disease state. A variety of techniques may be utilized to inhibit the expression, synthesis, or activity of such target genes and/or proteins.

For example, compounds such as those identified through assays described, above, in Section 5.5, which exhibit inhibitory activity, may be used in accordance with the invention to ameliorate cardiovascular disease symptoms. As discussed in Section 5.5, above, such molecules may include, but are not limited to small organic molecules, peptides, antibodies, and the like. Inhibitory antibody techniques are described, below, in Section 5.6.1.2.

For example, compounds can be administered that compete with endogenous ligand for a transmembrane target gene product. The resulting reduction in the amount of ligand-bound target gene transmembrane protein will modulate cell physiology. Compounds that can be particularly useful for this purpose include, for example, soluble proteins or peptides, such as peptides comprising one or more of the extracellular domains, or portions and/or analogs thereof, of the target gene product, including, for example, soluble fusion proteins such as Ig-tailed fusion proteins. (For a discussion of the production of Ig-tailed fusion proteins, see, for example, U.S. Pat. No. 5,116,964.). Alternatively, compounds, such as ligand analogs or antibodies, that bind to the target gene product receptor site, but do not activate the protein, (e.g., receptor-ligand antagonists) can be effective in inhibiting target gene product activity.

Further, antisense and ribozyme molecules which inhibit expression of the target gene may also be used in accordance with the invention to inhibit the aberrant target gene activity. Such techniques are described, below, in Section 5.6.1.1. Still further, also as described, below, in Section 5.6.1.1, triple helix molecules may be utilized in inhibiting the aberrant target gene activity.

5.6.1.1. Inhibitory Antisense, Ribozyme, Triple Helix, and Gene Inactivation Approaches Among the compounds which may exhibit the ability to ameliorate cardiovascular disease symptoms are antisense, ribozyme, and triple helix molecules. Such molecules may be designed to reduce or inhibit mutant target gene activity. Techniques for the production and use of such molecules are well known to those of skill in the art.

Antisense RNA and DNA molecules act to directly block the translation of mRNA by hybridizing to targeted mRNA and preventing protein translation.

Antisense approaches involve the design of oligonucleotides (either DNA or RNA) that are complementary to target gene mRNA. The antisense oligonucleotides will bind to the complementary target gene mRNA transcripts and prevent translation. Absolute complementary, although preferred, is not required. A sequence "complementary" to a portion of an RNA, as referred to herein, means a sequence having sufficient complementary to be able to hybridize with the RNA, forming a stable duplex; in the case of double-stranded antisense nucleic acids, a single strand of the duplex DNA may thus be tested, or triplex formation may be assayed. The ability to hybridize will depend on both the degree of complementary and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

Oligonucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs have recently shown to be effective at inhibiting translation of mRNAs as well. See generally, Wagner, R., 1994, Nature 372:333–335. Thus, oligonucleotides complementary to either the 5'- or 3'-non-translated, non-coding regions of the target gene could be used in an antisense approach to inhibit translation of endogenous target gene mRNA. Oligonucleotides complementary to the 5' untranslated region of the mRNA should include the complement of the AUG start codon. Antisense oligonucleotides complementary to mRNA coding regions are less efficient inhibitors of translation but could be used in accordance with the invention. Whether designed to hybridize to the 5'-, 3'- or coding region of target gene mRNA, antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides or at least 50 nucleotides.

Regardless of the choice of target sequence, it is preferred that in vitro studies are first performed to quantitate the ability of the antisense oligonucleotide to inhibit gene expression. It is preferred that these studies utilize controls that distinguish between antisense gene inhibition and non-specific biological effects of oligonucleotides. It is also preferred that these studies compare levels of the target RNA or protein with that of an internal control RNA or protein. Additionally, it is envisioned that results obtained using the antisense oligonucleotide are compared with those obtained using a control oligonucleotide. It is preferred that the control oligonucleotide is of approximately the same length as the test oligonucleotide and that the nucleotide sequence of the oligonucleotide differs from the antisense sequence no more than is necessary to prevent specific hybridization to the target sequence.

The oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger et al., 1989, Proc. Natl. Acad. Sci. U.S.A. 86:6553–6556; Lemaitre et al., 1987, Proc. Natl. Acad. Sci. 84:648–652; PCT Publication No. WO88/09810, published Dec. 15, 1988) or the blood-brain barrier (see, e.g., PCT Publication No. WO89/10134, published Apr. 25, 1988), hybridization-triggered cleavage agents. (See, e.g., Krol et al., 1988, BioTechniques 6:958–976) or intercalating agents. (See, e.g., Zon, 1988, Pharm. Res. 5:539–549). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including but not limited to 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

The antisense oligonucleotide may also comprise at least one modified sugar moiety selected from the group including but not limited to arabinose, 2-fluoroarabinose, xylulose, and hexose.

In yet another embodiment, the antisense oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier et al., 1987, Nucl. Acids Res. 15:6625–6641). The oligonucleotide is a 2'-β-methylhibonucleotide (Inoue et al., 1987, Nucl. Acids Res. 15:6131–6148), or a chimeric RNA-DNA analogue (Inoue et al., 1987, FEBS Lett. 215:327–330).

Oligonucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (1988, Nucl. Acids Res. 16:3209), methylphosphonate oligonucleotides can be prepared by use of controlled pore glass polymer supports (Sarin et al., 1988, Proc. Natl. Acad. Sci. U.S.A. 85:7448–7451), etc.

While antisense nucleotides complementary to the target gene coding region sequence could be used, those complementary to the transcribed untranslated region are most preferred.

Specific antisense oligonucleotides for the rchd534 gene and fchd540 gene are described in the Example in Section 12, below.

The antisense molecules should be delivered to cells which express the target gene in vivo, e.g., endothelial cells.

A number of methods have been developed for delivering antisense DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systemically.

However, it is often difficult to achieve intracellular concentrations of the antisense sufficient to suppress translation of endogenous mRNAs. Therefore a preferred approach utilizes a recombinant DNA construct in which the antisense oligonucleotide is placed under the control of a strong pol III or pol II promoter. The use of such a construct to transfect target cells in the patient will result in the transcription of sufficient amounts of single stranded RNAs that will form complementary base pairs with the endogenous target gene transcripts and thereby prevent translation of the target gene mRNA. For example, a vector can be introduced in vivo such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the antisense RNA can be by any promoter known in the art to act in mammalian, preferably human cells. Such promoters can be inducible or constitutive. Such promoters include but are not limited to: the SV40 early promoter region (Bernoist and Chambon, 1981, Nature 290:304–310), the promoter contained in the 3' long terminal repeat of Rous sarcoma virus (Yamamoto et al., 1980, Cell 22:787–797), the herpes thymidine kinase promoter (Wagner et al., 1981, Proc. Natl. Acad. Sci. U.S.A. 78:1441–1445), the regulatory sequences of the metallothionein gene (Brinster et al., 1982, Nature 296:39–42), etc. Any type of plasmid, cosmid, YAC or viral vector can be used to prepare the recombinant DNA construct which can be introduced directly into the tissue site; e.g., atherosclerotic vascular tissue. Alternatively, viral vectors can be used which selectively infect the desired tissue, in which case administration may be accomplished by another route (e.g., systemically).

Ribozymes are enzymatic RNA molecules capable of catalyzing the specific cleavage of RNA. The mechanism of ribozyme action involves sequence specific hybridization of the ribozyme molecule to complementary target RNA, followed by an endonucleolytic cleavage. Ribozyme molecules designed to catalytically cleave target gene mRNA transcripts can also be used to prevent translation of target gene mRNA and expression of target gene. (See, e.g., PCT International Publication WO90/11364, published Oct. 4, 1990; Sarver et al., 1990, Science 247:1222–1225). While ribozymes that cleave mRNA at site specific recognition sequences can be used to destroy target gene mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, 1988, Nature, 334:585–591. For example, there are hundreds of potential hammerhead ribozyme cleavage sites within the nucleotide sequence of rchd534 and fchd540 cDNA. Preferably the ribozyme is engineered so that the cleavage recognition site is located near the 5' end of the target mRNA; i.e., to increase efficiency and minimize the intracellular accumulation of non-functional mRNA transcripts.

Specific hammerhead ribozymes molecules for the rchd534 and fchd540 genes are described in the Example in Section 13, below.

The ribozymes of the present invention also include RNA endoribonucleases (hereinafter "Cech-type ribozymes") such as the one which occurs naturally in Tetrahymena Thermophila (known as the IVS, or L-19 IVS RNA) and which has been extensively described by Thomas Cech and collaborators (Zaug, et al., 1984, Science, 224:574–578; Zaug and Cech, 1986, Science, 231:470–475; Zaug, et al., 1986, Nature, 324:429–433; published International patent application No. WO 88/04300 by University Patents Inc.; Been and Cech, 1986, Cell, 47:207–216). The Cech-type ribozymes have an eight base pair active site which hybridizes to a target RNA sequence whereafter cleavage of the target RNA takes place. The invention encompasses those Cech-type ribozymes which target eight base-pair active site sequences that are present in target gene.

As in the antisense approach, the ribozymes can be composed of modified oligonucleotides (e.g. for improved stability, targeting, etc.) and should be delivered to cells which express the target gene in vivo, e.g., endothelial cells. A preferred method of delivery involves using a DNA construct "encoding" the ribozyme under the control of a strong constitutive pol III or pol III promoter, so that transfected cells will produce sufficient quantities of the ribozyme to destroy endogenous target gene messages and inhibit translation. Because ribozymes, unlike antisense molecules, are catalytic, a lower intracellular concentration is required for efficiency.

Nucleic acid molecules to be used in triple helix formation for the inhibition of transcription should be single stranded and composed of deoxyribonucleotides. The base composition of these oligonucleotides must be designed to promote triple helix formation via Hoogsteen base pairing rules, which generally require sizeable stretches of either purines or pyrimidines to be present on one strand of a duplex. Nucleotide sequences may be pyrimidine-based, which will result in TAT and CGC$^+$ triplets across the three associated strands of the resulting triple helix. The pyrimidine-rich molecules provide base complementary to a purine-rich region of a single strand of the duplex in a parallel orientation to that strand. In addition, nucleic acid molecules may be chosen that are purine-rich, for example, containing a stretch of G residues. These molecules will form a triple helix with a DNA duplex that is rich in GC paris, in which the majority of the purine residues are located on a single strand of the targeted duplex, resulting in GGC triplets across the three strands in the triplex.

Alternatively, the potential sequences that can be targeted for triple helix formation may be increased by creating a so called "switchback" nucleic acid molecule. Switchback molecules are synthesized in an alternating 5'-3', 3'-5' manner, such that they base pair with first one strand of a duplex and then the other, eliminating the necessity for a sizeable stretch of either purines or pyrimidines to be present on one strand of a duplex.

It is possible that the antisense, ribozyme, and/or triple helix molecules described herein may reduce or inhibit the transcription (triple helix) and/or translation (antisense, ribozyme) of mRNA produced by both normal and mutant target gene alleles. In order to ensure that substantially normal levels of target gene activity are maintained, nucleic acid molecules that encode and express target gene polypeptides exhibiting normal activity may be introduced into cells via gene therapy methods such as those described, below, in Section 5.7. that do not contain sequences susceptible to whatever antisense, ribozyme, or triple helix treatments are being utilized. Alternatively, it may be preferable to coadminister normal target gene protein into the cell or tissue in order to maintain the requisite level of cellular or tissue target gene activity.

Endogenous target gene expression can also be reduced by inactivating or "knocking out" the target gene or its promoter using targeted homologous recombination. (E.g., see Smithies et al., 1985, Nature 317:230–234; Thomas & Capecchi, 1987, Cell 51:503–512; Thompson et al., 1989 Cell 5:313–321; each of which is incorporated by reference herein in its entirety). For example, a mutant, non-functional target (or a completely unrelated DNA sequence) flanked by DNA homologous to the endogenous target gene (either the coding regions or regulatory regions of the target gene) can be used, with or without a selectable marker and/or a negative selectable marker, to transfect cells that express target in vivo. Insertion of the DNA construct, viatargeted homologous recombination, results in inactivation of the target gene. Such approaches can be adapted for use in humans provided the recombinant DNA constructs are directly administered or targeted to the required site in vivo using appropriate viral vectors, e.g., vectors for delivery vascular tissue.

Alternatively, endogenous target gene expression can be reduced by targeting deoxyribonucleotide sequences complementary to the regulatory region of the target gene (i.e., the target promoter and/or enhancers) to form triple helical structures that prevent transcription of the target gene in target cells in the body. (See generally, Helene, C. 1991, Anticancer Drug Des., 6(6):569–84; Helene, C., et al., 1992, Ann, N.Y. Acad. Sci., 660:27–36; and Maher, L. J., 1992, Bioassays 14(12):807–15).

In yet another embodiment of the invention, the activity of a target can be reduced using a "dominant negative" approach to effectuate reduction in cardiovascular disease symptoms. For example, if two gene products interact, such as the rchd534 and fchd540 proteins, then the presence of a mutant version of one or both of these proteins in the cell can reduce the overall pool of complexes consisting of entirely wild-type proteins. In this manner, the overall level of activity resulting from the rchd534/fchd540 protein interaction can be reduced.

5.6.1.2. Antibodies for Target Gene Products

Antibodies that are both specific for target gene protein and interfere with its activity may be used to inhibit target gene function. Such antibodies may be generated using standard techniques described in Section 5.4.3., supra, against the proteins themselves or against peptides corresponding to portions of the proteins. Such antibodies include but are not limited to polyclonal, monoclonal, Fab fragments, single chain antibodies, chimeric antibodies, etc.

In instances where the target gene protein is intracellular and whole antibodies are used, internalizing antibodies may be preferred. However, lipofectin liposomes may be used to deliver the antibody or a fragment of the Fab region which binds to the target gene epitope into cells. Where fragments of the antibody are used, the smallest inhibitory fragment which binds to the target protein's binding domain is preferred. For example, peptides having an amino acid sequence corresponding to the domain of the variable region of the antibody that binds to the target gene protein may be used. Such peptides may be synthesized chemically or produced via recombinant DNA technology using methods well known in the art (e.g., see Creighton, 1983, supra; and Sambrook et al., 1989, supra). Alternatively, single chain neutralizing antibodies which bind to intracellular target gene epitopes may also be administered. Such single chain antibodies may be administered, for example, by expressing nucleotide sequences encoding single-chain antibodies within the target cell population by utilizing, for example, techniques such as those described in Marasco et al. (Marasco, W. et al., 1993, Proc. Natl. Acad. Sci. USA 90:7889–7893).

In some instances, the target gene protein is extracellular, or is a transmembrane protein, such as the fchd545 and fchd602 gene products. Antibodies that are specific for one or more extracellular domains of these gene products, for example, and that interfere with its activity, are particularly useful in treating cardiovascular disease. Such antibodies are especially efficient because they can access the target domains directly from the bloodstream. Any of the administration techniques described, below in Section 5.7 which are appropriate for peptide administration may be utilized to effectively administer inhibitory target gene antibodies to their site of action.

5.6.2. Methods for Restoring or Enhancing Target Gene Activity

Target genes that cause cardiovascular disease may be underexpressed within cardiovascular disease situations. As summarized in Table 1, above, and detailed in the example in Section 7, below, several genes are now known to be down-regulated in endothelial cells under disease conditions. Specifically, fchd531 and fchd545 are down-regulated in endothelial cells subjected to shear stress. Alternatively, the activity of target gene products may be decreased, leading to the development of cardiovascular disease symptoms. Such down-regulation of target gene expression or decrease of target gene product activity might have a causative or exacerbating effect on the disease state.

In some cases, target genes that are up-regulated in the disease state might be exerting a protective effect. As summarized in Table 1, above, and detailed in the examples in Sections 6 and 7, below, a number of genes are now known to be up-regulated in monocytes and endothelial cells under disease conditions. Specifically, fchd602 and fchd605 are each up-regulated in monocytes treated with oxidized LDL. Furthermore, fchd540 is up-regulated in endothelial cells subjected to shear stress. A variety of techniques may be utilized to increase the expression, synthesis, or activity of such target genes and/or proteins, for those genes that exert a protective effect in response to disease conditions.

Compounds or substances which enhance the expression of a gene or the activity of a gene product are referred to as agonists. Compounds or substances which decrease the expression of a gene or the activity of a gene product are referred to as antagonists.

Described in this Section are methods whereby the level of target gene activity may be increased to levels wherein cardiovascular disease symptoms are ameliorated. The level of gene activity may be increased, for example, by either increasing the level of target gene product present or by increasing the level of active target gene product which is present.

For example, a target gene protein, at a level sufficient to ameliorate cardiovascular disease symptoms may be administered to a patient exhibiting such symptoms. Any of the techniques discussed, below, in Section 5.7, may be utilized for such administration. One of skill in the art will readily know how to determine the concentration of effective, non-toxic a doses of the normal target gene protein, utilizing techniques such as those described, below, in Section 5.7.1.

Additionally, RNA sequences encoding target gene protein may be directly administered to a patient exhibiting cardiovascular disease symptoms, at a concentration sufficient to produce a level of target gene protein such that cardiovascular disease symptoms are ameliorated. Any of the techniques discussed, below, in Section 5.7, which achieve intracellular administration of compounds, such as, for example, liposome administration, may be utilized for the administration of such RNA molecules. The RNA molecules may be produced, for example, by recombinant techniques such as those described, above, in Section 5.4.2.

Further, patients may be treated by gene replacement therapy. One or more copies of a normal target gene, or a portion of the gene that directs the production of a normal target gene protein with target gene function, may be inserted into cells using vectors which include, but are not limited to adenovirus, adeno-associated virus, and retrovirus vectors, in addition to other particles that introduce DNA into cells, such as liposomes. Additionally, techniques such as those described above may be utilized for the introduction of normal target gene sequences into human cells.

Cells, preferably, autologous cells, containing normal target gene expressing gene sequences may then be introduced or reintroduced into the patient at positions which allow for the amelioration of cardiovascular disease symptoms. Such cell replacement techniques may be preferred, for example, when the target gene product is a secreted, extracellular gene product.

5.7. Pharmaceutical Preparations and Methods of Administration

The identified compounds that inhibit target gene expression, synthesis and/or activity can be administered to a patient at therapeutically effective doses to treat or ameliorate cardiovascular disease. A therapeutically effective dose refers to that amount of the compound sufficient to result in amelioration of symptoms of cardiovascular disease.

5.7.1. Effective Dose

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

5.7.2. Formulations and Use

Pharmaceutical compositions for use in accordance with the present invention may be formulated in conventional manner using one or more physiologically acceptable carriers or excipients.

Thus, the compounds and their physiologically acceptable salts and solvates may be formulated for administration by inhalation or insufflation (either through the mouth or the nose) or oral, buccal, parenteral or rectal administration.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound.

For buccal administration the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

5.8. Diagnosis of Cardiovascular Disease Abnormalties

A variety of methods may be employed, utilizing reagents such as fingerprint gene nucleotide sequences described in Section 5.4.1, and antibodies directed against differentially expressed and pathway gene peptides, as described, above, in Sections 5.4.2. (peptides) and 5.4.3. (antibodies). Specifically, such reagents may be used, for example, for the detection of the presence of target gene mutations, or the detection of either over or under expression of target gene mRNA.

The methods described herein may be performed, for example, by utilizing pre-packaged diagnostic kits comprising at least one specific fingerprint gene nucleic acid or anti-fingerprint gene antibody reagent described herein, which may be conveniently used, e.g., in clinical settings, to diagnose patients exhibiting cardiovascular disease symptoms or at risk for developing cardiovascular disease.

Any cell type or tissue, preferably monocytes, endothelial cells, or smooth muscle cells, in which the fingerprint gene is expressed may be utilized in the diagnostics described below.

5.8.1. Detection of Fingerprint Gene Nucleic Acids

DNA or RNA from the cell type or tissue to be analyzed may easily be isolated using procedures which are well known to those in the art. Diagnostic procedures may also be performed "in situ" directly upon tissue sections (fixed and/or frozen) of patient tissue obtained from biopsies or resections, such that no nucleic acid purification is necessary. Nucleic acid reagents such as those described in Section 5.1. may be used as probes and/or primers for such in situ procedures (see, for example, Nuovo, G. J., 1992, PCR in situ hybridization: protocols and applications, Raven Press, N.Y.).

Fingerprint gene nucleotide sequences, either RNA or DNA, may, for example, be used in hybridization or amplification assays of biological samples to detect cardiovascular disease-related gene structures and expression. Such assays may include, but are not limited to, Southern or Northern analyses, single stranded conformational polymorphism analyses, in situ hybridization assays, and polymerase chain reaction analyses. Such analyses may reveal both quantitative aspects of the expression pattern of the fingerprint gene, and qualitative aspects of the fingerprint gene expression and/or gene composition. That is, such aspects may include, for example, point mutations, insertions, deletions, chromosomal rearrangements, and/or activation or inactivation of gene expression.

Preferred diagnostic methods for the detection of fingerprint gene-specific nucleic acid molecules may involve for example, contacting and incubating nucleic acids, derived from the cell type or tissue being analyzed, with one or more labeled nucleic acid reagents as are described in Section 5.1, under conditions favorable for the specific annealing of these reagents to their complementary sequences within the nucleic acid molecule of interest. Preferably, the lengths of these nucleic acid reagents are at least 9 to 30 nucleotides. After incubation, all non-annealed nucleic acids are removed from the nucleic acid:fingerprint molecule hybrid. The presence of nucleic acids from the fingerprint tissue which have hybridized, if any such molecules exist, is then detected. Using such a detection scheme, the nucleic acid from the tissue or cell type of interest may be immobilized, for example, to a solid support such as a membrane, or a plastic surface such as that on a microtitre plate or polystyrene beads. In this case, after incubation, non-annealed, labeled fingerprint nucleic acid reagents of the type described in Section 5.1. are easily removed. Detection of the remaining, annealed, labeled nucleic acid reagents is accomplished using standard techniques well-known to those in the art.

Alternative diagnostic methods for the detection of fingerprint gene specific nucleic acid molecules may involve their amplification, e.g., by PCR (the experimental embodiment set forth in Mullis, K. B., 1987, U.S. Pat. No. 4,683, 202), ligase chain reaction (Barany, F., 1991, Proc. Natl. Acad. Sci. USA 88:189–193), self sustained sequence replication (Guatelli, J. C. et al., 1990, Proc. Natl. Acad. Sci. USA 87:1874–1878), transcriptional amplification system (Kwoh, D. Y et al., 1989, Proc. Natl. Acad. Sci. USA 86:1173–1177), Q-Beta Replicase (Lizardi, P. M. et al., 1988, Bio/Technology 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In one embodiment of such a detection scheme, a cDNA molecule is obtained from an RNA molecule of interest (e.g., by reverse transcription of the RNA molecule into cDNA). Cell types or tissues from which such RNA may be isolated include any tissue in which wild type fingerprint gene is known to be expressed, including, but not limited, to monocytes, endothelium, and/or smooth muscle. A fingerprint sequence within the cDNA is then used as the template for a nucleic acid amplification reaction, such as a PCR amplification reaction, or the like. The nucleic acid reagents used as synthesis initiation reagents (e.g., primers) in the reverse transcription and nucleic acid amplification steps of this method are chosen from among the fingerprint gene nucleic acid reagents described in Section 5.1. The preferred lengths of such nucleic acid reagents are at least 15–30 nucleotides. For detection of the amplified product, the nucleic acid amplification may be performed using radioactively or non-radioactively labeled nucleotides. Alternatively, enough amplified product may be made such that the product may be visualized by standard ethidium bromide staining or by utilizing any other suitable nucleic acid staining method.

In addition to methods which focus primarily on the detection of one nucleic acid sequence, fingerprint profiles, as discussed in Section 5.5.4, may also be assessed in such detection schemes. Fingerprint profiles may be generated, for example, by utilizing a differential display procedure, as discussed, above, in Section 5.1.2, Northern analysis and/or RT-PCR. Any of the gene sequences described, above, in Section 5.4.1. may be used as probes and/or PCR primers for the generation and corroboration of such fingerprint profiles.

5.8.2. Detection of Fingerprint Gene Peptides

Antibodies directed against wild type or mutant fingerprint gene peptides, which are discussed, above, in Section 5.4.3, may also be used as cardiovascular disease diagnostics and prognostics, as described, for example, herein. Such diagnostic methods, may be used to detect abnormalities in the level of fingerprint gene protein expression, or abnormalities in the structure and/or tissue, cellular, or subcellular location of fingerprint gene protein. Structural differences may include, for example, differences in the size, electronegativity, or antigenicity of the mutant fingerprint gene protein relative to the normal fingerprint gene protein.

Protein from the tissue or cell type to be analyzed may easily be detected or isolated using techniques which are well known to those of skill in the art, including but not limited to western blot analysis. For a detailed explanation of methods for carrying out western blot analysis, see Sambrook et al, 1989, supra, at Chapter 18. The protein detection and isolation methods employed herein may also be such as those described in Harlow and Lane, for example, (Harlow, E. and Lane, D., 1988, "Antibodies: A Laboratory Manual", Cold Spring Harbor Laboratory Press, Cold Spring Harbor, N.Y.), which is incorporated herein by reference in its entirety.

Preferred diagnostic methods for the detection of wild type or mutant fingerprint gene peptide molecules may involve, for example, immunoassays wherein fingerprint gene peptides are detected by their interaction with an anti-fingerprint gene specific peptide antibody.

For example, antibodies, or fragments of antibodies, such as those described, above, in Section 5.4.3, useful in the present invention may be used to quantitatively or qualitatively detect the presence of wild type or mutant fingerprint gene peptides. This can be accomplished, for example, by immunofluorescence techniques employing a fluorescently labeled antibody (see below) coupled with light microscopic, flow cytometric, or fluorimetric detection. Such techniques are especially preferred if the fingerprint gene peptides are expressed on the cell surface.

The antibodies (or fragments thereof useful in the present invention may, additionally, be employed histologically, as in immunofluorescence or inmmunoelectron microscopy, for in situ detection of fingerprint gene peptides. In situ detection may be accomplished by removing a histological specimen from a patient, and applying thereto a labeled antibody of the present invention. The antibody (or fragment) is preferably applied by overlaying the labeled antibody (or fragment) onto a biological sample. Through the use of such a procedure, it is possible to determine not only the presence of the fingerprint gene peptides, but also their distribution in the examined tissue. Using the present invention, those of ordinary skill will readily perceive that any of a wide variety of histological methods (such as staining procedures) can be modified in order to achieve such in situ detection.

Immunoassays for wild type or mutant fingerprint gene peptides typically comprise incubating a biological sample, such as a biological fluid, a tissue extract, freshly harvested cells, or cells which have been incubated in tissue culture, in the presence of a detectably labeled antibody capable of identifying fingerprint gene peptides, and detecting the bound antibody by any of a number of techniques well known in the art.

The biological sample may be brought in contact with and immobilized onto a solid phase support or carrier such as nitrocellulose, or other solid support which is capable of immobilizing cells, cell particles or soluble proteins. The support may then be washed with suitable buffers followed by treatment with the detectably labeled fingerprint gene specific antibody. The solid phase support may then be washed with the buffer a second time to remove unbound antibody. The amount of bound label on solid support may then be detected by conventional means.

By "solid phase support or carrier" is intended any support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

The binding activity of a given lot of anti-wild type or mutant fingerprint gene peptide antibody may be determined according to well known methods. Those skilled in the art will be able to determine operative and optimal assay conditions for each determination by employing routine experimentation.

One of the ways in which the fingerprint gene peptide-specific antibody can be detectably labeled is by linking the same to an enzyme and use in an enzyme immunoassay (EIA) (Voller, "The Enzyme Linked Immunosorbent Assay (ELISA)", *Diagnostic Horizons* 2:1–7, 1978, Microbiological Associates Quarterly Publication, Walkersville, Md.; Voller, et al., J. Clin. Pathol. 31:507–520 (1978); Butler, Meth. Enzymol. 73:482–523 (1981); Maggio, (ed.) *Enzyme Immunoassay*, CRC Press, Boca Raton, Fla., 1980; Ishikawa, et al., (eds.) *Enzyme Immunoassay*, Kgaku Shoin, Tokyo, 1981). The enzyme which is bound to the antibody will react with an appropriate substrate, preferably a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods which employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the antibodies or antibody fragments, it is possible to detect fingerprint gene wild type or mutant peptides through the use of a radioimmunoassay (RIA) (see, for example, Weintraub, B., *Principles of Radioimmunoassays*, Seventh Training Course on Radioligand Assay Techniques, The Endocrine Society, March, 1986, which is incorporated by reference herein). The radioactive isotope can be detected by such means as the use of a gamma counter or a scintillation counter or by autoradiography.

It is also possible to label the antibody with a fluorescent compound. When the fluorescently labeled antibody is exposed to light of the proper wave length, its presence can It .then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine.

The antibody can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, abioluminescent compound may be used to label the antibody of the present invention. Bioluminescence is a type of chemiluminescence found in biological systems in, which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

5.8.3. Imaging Cardiovascular Disease Conditions

In some cases, differentially expressed gene products identified herein may be up-regulated under cardiovascular disease conditions and expressed on the surface of the affected tissue. Such target gene products allow for the non-invasive imaging of damaged or diseased cardiovascular tissue for the purposed of diagnosis and directing of treatment of the disease. For example, such differentially expressed gene products may include but are not limited to atherosclerosis specific adhesion molecules responsible for atherogenesis, or monocyte scavenger receptors that are up-regulated in response to oxidized LDL, which are discussed in Section 2, above. Alternatively, other such surface proteins may be specifically up-regulated in tissues suffering from ischemnia/reperfusion or other tissues with atherosclerotic or restenotic lesions.

As described in the example in Section 6, below, fchd602 is a gene that is up-regulated in monocytes under disease conditions. Furthermore, the fchd602 gene encodes a novel protein containing multiple transmembrane domains. Not only is the fchd602 gene expressed in monocytes, which play a role in the initiation and progression of atherosclerotic lesions, it is also upregulated in monocytes under such disease conditions. The fchd602 gene product, therefore, provides and excellent tool for imaging cardiovascular disease conditions.

This method can be applied in a similar manner to other transmembrane target gene products, such as the fchd545 gene product. As described in the example in Section 7, below, the fchd545 gene encodes a novel anion channel, containing multiple transmembrane domains. Because the fchd545 gene product might be more readily detected in normal tissue, as opposed to tissue in the disease state, it also provides an excellent tool for imaging cardiovascular disease conditions.

An example illustrating the use of this method in accordance with the invention is provided in Section 9, below. Monoclonal and polyclonal antibodies, as described in Section 5.6.1.2, above, which specifically bind to such surface proteins, such as the fchd602 and fchd545 gene products, can be used for the diagnosis of cardiovascular disease by in vivo tissue imaging techniques. Such antibodies raised against the fchd545 gene product are described in detail in the example in Section 10, below. An antibody specific for a target gene product, or preferably an antigen binding fragment thereof, is conjugated to a label (e.g., a gamma emitting radioisotope) which generates a detectable signal and administered to a subject (human or animal) suspected of having cardiovascular disease. After sufficient time to allow the detectably-labeled antibody to localize at the diseased or damaged tissue site (or sites), the signal generated by the label is detected by a photoscanning device. The detected signal is then converted to an image of the tissue. This image makes it possible to localize the tissue in vivo. This data can then be used to develop an appropriate therapeutic strategy.

Antibody fragments, rather than whole antibody molecules, are generally preferred for use in tissue imaging. Antibody fragments accumulate at the tissue(s) more rapidly because they are distributed more readily than are entire antibody molecules. Thus an image can be obtained in less time than is possible using whole antibody. These fragments are also cleared more rapidly from tissues, resulting in a lower background signal. See, e.g., Haber et al., U.S. Pat. No. 4,036,945; Goldenberg et al., U.S. Pat. No. 4,331,647. The divalent antigen binding fragment $(Fab')_2$ and the monovalent Fab are especially preferred. Such fragments can be prepared by digestion of the whole immunoglobulin molecule with the enzymes pepsin or papain according to any of several well known protocols. The types of labels that are suitable for conjugation to a monoclonal antibody for diseased or damaged tissue localization include, but are not limited to radiolabels (i.e., radioisotopes), fluorescent labels and biotin labels.

Among the radioisotopes that can be used to label antibodies or antibody fragments, gamma-emitters, positron-emitters, X-ray-emitters and fluorescence-emitters are suitable for localization. Suitable radioisotopes for labeling antibodies include Iodine-131, Iodine-123, Iodine-125, Iodine-126, Iodine-133, Bromine-77, Indium-111, Indium-113m, Gallium-67, Gallium-68, Ruthenium-95, Ruthenium-97, Ruthenium-103, Ruthenium-105, Mercury-107, Mercury-203, Rhenium-99m, Rhenium-105, Rhenium-101, Tellurium-121m, Tellurium-122m, Tellurium-125m, Thulium-165, Thulium-167, Thulium-168, Technetium-99m and Fluorine-18. The halogens can be used more or less interchangeably as labels since halogen-labeled antibodies and/or normal immunoglobulins would have substantially the same kinetics and distribution and similar metabolism.

The gamma-emitters Indium-111 and Technetium-99m are preferred because these radiometals are detectable with a gamma camera and have favorable half lives for imaging in vivo. Antibody can be labelled with Indium-111 or Technetium-99m via a conjugated metal chelator, such as DTPA (diethlenetriaminepentaacetic acid). See Krejcarek et al., 1977, Biochem. Biophys. Res. Comm. 77:581; Khaw et al., 1980, Science 209:295; Gansow et al., U.S. Pat. No. 4,472,509; Hnatowich, U.S. Pat. No. 4,479,930, the teachings of which are incorporated herein by reference.

Fluorescent compounds that are suitable for conjugation to a monoclonal antibody include fluorescein sodium, fluorescein isothiocyanate, and Texas Red sulfonyl chloride. See, DeBelder & Wik, 1975, Carbohydrate Research 44:254–257. Those skilled in the art will know, or will be able to ascertain with no more than routine experimentation, other fluorescent compounds that are suitable for labeling monoclonal antibodies.

6. EXAMPLE

Identification of Genes Differentially Expressed in Respones to Paradigm A: in Vitro Foam Cell Paradigm According to the invention, differential display may be used to detect genes that are differentially expressed in monocytes that were treated so as to simulate the conditions under which foam cells develop during atherogenesis. By use of Paradigm A, the novel genes fchd602 and fchd605 were identified. Both fchd602 and fchd605 are up-regulated under the disease condition of treatment with oxidized LDL.

The fchd602 gene product contains multiple transmembrane domains, and has sequence similarity to the rat Cl-6 gene, which is induced in regenerating rat liver, is insulin inducible, and also contains multiple transmembrane domains (Diamond, R. H., et al., 1993, J. Biol. Chem. 268: 15185–15192). The fchd605 gene product has sequence similarity to the mouse gly96 gene (Charles, C. H., et al., 1993, Oncogene 8: 797–801), and to EST T49532.

The discovery of the up-regulation of these two genes provides a fingerprint profile, e.g., markers, for monocytes in the process of foam cell formation. This profile can be used in the treatment and diagnosis of cardiovascular disease, including but not limited to atherosclerosis, ischemia/reperfusion, hypertension, restenosis, and arterial inflammation.

Furthermore, as a transmembrane protein, the fchd602 gene product can be readily accessed or detected on the monocyte cell surface by other compounds. It provides, therefore, an excellent target for detection of cardiovascular disease states in diagnostic systems, as well as in the monitoring of the efficacy of compounds in clinical trials. Furthermore, the extracellular domains of this gene product provide targets which allow for the design of especially efficient screening systems for identifying compounds that bind to them. Such compounds can be useful in treating cardiovascular disease by modulating the activity of the transmembrane gene product.

6.1. Materials and Methods 6.1.1. Cell Isolation and Culturing

Blood (~200 ml) was drawn into chilled 20 ml vacutainer tubes to which 3 ml of citrate phosphate dextrose (Sigma) was added. Blood was then pooled into 50 ml tubes and spun in the Beckman GS-6R at 1250 RPM for 15 minutes at 4° C. The upper clear layer (~25 ml) was then removed with a pipette and discarded and replaced with the same volume of 4° C. PBS. The blood was then mixed, and spun again at 2680 RPM for 15 minutes at 4° C. The upper layer was then removed and discarded, and the buffy coat at the interface was removed in ~5 ml and placed in a separate 50 ml tube, and the pipette was washed with 20 ml PBS. Cells were added to a T flask and stored at 4° C. for 16 hours. A small aliquot of the cells were then removed and counted using a hemacytometer. The final red blood cell concentration in the buffy coat population was then adjusted to $1.5 \times 10^9$/ml with PBS, the cells were added to Leucoprep tubes (Becton Dickinson) after being allowed to come to room temperature, and spun at 2300 RPM for 25 minutes at 25° C. The upper clear layer was removed and discarded and the turbid layer over the gel was removed and pooled in 50 ml tubes. Samples were then diluted to 50 ml with PBS (25° C.) and spun at 1000 RPM for 10 minutes. The supernatant was then removed, and the pellet was resuspended in 50 ml PBS. This procedure was repeated 3 more times. After the last spin, the cells were resuspended in a small volume of PBS and counted.

Tissue culture dishes were coated with bovine collagen before monocytes were plated out. ⅙ volume of 7×RPMI (JRH Biosciences) was added to Vitrogen 100 collagen (Celtrix) which was then diluted 1:10 with RPMI to a final concentration of 0.35 mg/ml. Collagen mixture was then added to plates (2.5 ml/100 nm dish) and placed at 37° C. for at least one hour to allow for gel formation. After gel formation has taken place, the RPMI was removed and cells were added in RPMI/10% plasma derived serum (PDS). PDS was prepared by drawing blood into chilled evacuated tubes containing ¹⁄₁₀th volume 3.8% sodium citrate. Blood was then transferred into new Sorvall tubes and spun at 14,000–16,000 RPM for 20 minutes at 4° C. Plasma layer was removed and pooled in new tubes to which ¹⁄₅₀th volume 1M $CaCl_2$ was added. Plasma was mixed and aliquoted into new Sorvall tubes and incubated at 37% for 2 hours to allow for fibrin clot formation. The clot was then disturbed with a pipette to allow it to contract and tubes were spun at 14,500 RPM for 20 minutes at 25° C. Supernatant was collected, pooled, and heat inactivated at 56° C. prior to sterile filtration and freezing.

Purified human monocytes were cultured in 10% PDS/RPMI containing 5 units/ml of Genzyme recombinant human MCSF for 5 days before being treated with LDL, oxidized LDL, acetylated LDL (all LDL at 50 µg/ml), lysophosphatidylcholine (Sigma, 37.5 µM), or homocysteine (Sigma, 1 mM). After incubation with these reagents for periods ranging from 2 hours up to 3 days, the media was withdrawn and the cells were dissolved in RNA lysis buffer and RNA was prepared as described, above, in Section 6.1.

Lipoproteins For oxidation, human LDL (Sigma) was first diluted to 1 mg/ml with PBS and then dialyzed against PBS at 4° C. overnight. LDL was then diluted to 0.3 mg/ml with PBS. $CuSO_4.5H_2O$ was then added to 5 uM final concentration, and the solution was incubated in a T flask in a 37° C. incubator for 24 hr. LDL solution was then dialyzed at 4° C. against 0.15M NaCl/0.3 mM EDTA for 2 days with several changes, before being removed and concentrated using an Amicon spin column by spinning for 1 hr. 4000 RPM at 4° C.

For acetylation, 1 ml of 5 mg/ml LDL was added to 1 ml of a saturated solution of NaOAc in a 15 ml tube on ice on a shaker at 4° C. 8 µl of acetic anhydride was added 2 µl at a time over 1 hr. LDL was then dialyzed for 48 hr. against 0.15M NaCl/0.3 mM EDTA at 4° C. for 48 hr. with several changes. Final concentrations of derivatized LDL's were determined by comparing to a dilution curve of native LDL analyzed at $OD_{280}$, with 0.15M NaCl/0.3 mM EDTA used as diluent in all cases.

6.1.2. Analysis of Paradigm Material Differential Display:

Removal of DNA: The RNA pellet was resuspended in $H_2O$ and quantified by spectrophotometry at $OD_{260}$. Approximately half of the sample was then treated with DNAse I to remove contaminating chromosomal DNA. RNA was amplified by PCR using the following procedure. 50 ul RNA sample (10–20 µg), 5.7 µl 10×PCR buffer (Perkin-Elmer/Cetus), 1 µl RNAse inhibitor (40 units/µl) (Boehringer Mannheim, Germany) were mixed together, vortexed, and briefly spun. 2 µl DNAse I (10 units/µl) (Boehringer Mannheim) was added to the reaction which was incubated for 30 min. at 37° C. The total volume was brought to 200 µl with DEPC $H_2O$, extracted once with phenol/chloroform, once with chloroform, and precipitated by adding 20 µl 3M NaOAc, pH 4.8, (DEPC-treated), 500 µl absolute ETOH and incubating for 1 hour on dry ice or −20° C. overnight. The precipitated sample was centrifuged for 15 min., and the pellet was washed with 70% ETOH. The sample was re-centrifuged, the remaining liquid was aspirated, and the pellet was resuspended in 100 µl $H_2O$. The concentration of RNA was measured by reading the $OD_{260}$.

First strand cDNA synthesis: For each RNA sample duplicate reactions were carried out in parallel. 400 ng RNA plus DEPC $H_2O$ in a total volume of 10 µl were added to 4 µl $T_{11}XX$ reverse primer (10 µM) (Operon). The specific primers used in each experiment are provided in the Description of the Figures in Section 4, above. The mixture was incubated at 70° C. for 5 min. to denature the RNA and then placed at r.t. 26 µl of reaction mix containing the following components was added to each denatured RNA/primer sample: 8 µl 5×First Strand Buffer (Gibco/BRL, Gaithersburg, Md.), 4 µl 0.1M DTT (Gibco/BRL), 2 µl RNAse inhibitor (40 units/µl) (Boehringer Mannheim), 4 µl 200 µM dNTP mix, 6 µl $H_2O$, 2 µl Superscript reverse transcriptase (200 units/µl) (Gibco/BRL). The reactions were mixed gently and incubated for 30 min. at 42° C. 60 µl of $H_2O$ (final volume=100 µl) were then added and the samples were denatured for 5 min. at 85° C. and stored at −20° C.

PCR reactions: 13 µl of reaction mix was added to each tube of a 96 well plate on ice. The reaction mix contained 6.4 µl $H_2O$, 2 µl 10×PCR Buffer (Perkin-Elmer), 2 µl 20 µM dNTP's, 0.4 µl $^{35}S$ dATP (12.5 µCi/µl; 50 µCi total) (Dupont/NEN), 2 µl forward (for-) primer (10 µM) (Operon), and 0.2 µl AmpliTaq Polymerase (5 units/µl) (Perkin-Elmer). Next, 2 µl of reverse (rev-) primer ($T_{11}XX$, 10 µM) were added to the side of each tube followed by 5 µl of cDNA also to the sides of the tubes, which were still on ice. The specific primers used in each experiment were as follows:

fchd602: rev-$T_{11}XC$ (SEQ ID NO:13) and for-GTGAGGCGTC (SEQ ID NO:14)

fchd605: rev-$T_{11}XC$ (SEQ ID NO:13) and for-TGGACCGGTG (SEQ ID NO:15)

Tubes were capped and mixed, and brought up to 1000 RPM in a centrifuge then returned immediately to ice. The PCR machine (Perkin-Elmer 9600) was programmed for differential display as follows:

|        |           |         |
|--------|-----------|---------|
|        | 94° C.    | 2 min.  |
|        | *94° C.   | 15 sec. |
|        | *40° C.   | 2 min.  |
| * = X40| *ramp 72° C. | 1 min. |
|        | *72° C.   | 30 sec. |
|        | 72° C.    | 5 min.  |
|        | 4° C. hold |        |

When the PCR machine reached 94° C., the plate was removed from ice and placed directly into the Perkin-Elmer 9600 PCR machine. Following PCR, 15 µl of loading dye, containing 80% formamide, 10 mM EDTA, 1 mg/ml xylene cyanol, 1 mg/ml bromphenol blue were added. The loading dye and reaction were mixed, incubated at 85° C. for 5 min., cooled on ice, centrifuged, and placed on ice. Approximately 4 µl from each tube were loaded onto a prerun (60V) 6% acrylamide gel. The gel was run at approximately 80V until top dye front was about 1 inch from bottom. The gel was transferred to 3MM paper (Whatman Paper, England) and dried under vacuum. Bands were visualized by autoradiography.

Band isolation and amplification: Differentially expressed bands were excised from the dried gel with a razor blade and placed into a microfuge tube with 100 μl H$_2$O and heated at 100° C. for 5 min., vortexed, heated again to 100° C. for 5 min., and vortex again. After cooling, 100 μl H$_2$O, 20 μl 3M NaOAc, 1 μl glycogen (20 mg/ml), and 500 μl ethanol were added and chilled. After centrifugation, the pellet was washed and resuspended in 10 μl H$_2$O.

The isolated differentially expressed bands were then amplified by PCR using the following reaction conditions:

| | |
|---|---|
| 58 μl | H$_2$O |
| 10 μl | 10x PCR Buffer |
| 10 μl | 200 μm dNTP' |
| 10 μl | 10 μM reverse primer |
| 10 μl | 10 μM forward primer |
| 1.5 μl | amplified band |
| 0.5 μl | AmpliTaq polymerase (5 units/μl) |

(Perkin Elmer)

PCR was performed using the program described in this Section, above, for differential display. After PCR, glycerol loading dyes were added and samples were loaded onto a 2% preparative TAE/Biogel (Bio101, La Jolla, Calif.) agarose gel and eluted. Bands were then excised from the gel with a razor blade and vortexed for 15 min. at r.t., and purified using the Mermaid kit from Bio101 by adding 3 volumes of Mermaid high salt binding solution and 8 μl of resuspended glassfog in a microfuge tube. Glassfog was then pelleted, washed 3 times with ethanol wash solution, and then DNA was eluted twice in 10 μl at 50° C.

Subcloning: The TA cloning kit (Invitrogen, San Diego, Calif.) was used to subclone the amplified bands. The ligation reaction typically consisted of 4 μl sterile H$_2$O, 1 μl ligation buffer, 2 μl TA cloning vector, 2 μl PCR product, and 1 μl T4 DNA ligase. The volume of PCR product can vary, but the total volume of PCR product plus H$_2$O was always 6 μl. Ligations (including vector alone) were incubated overnight at 12° C. before bacterial transformation. TA cloning kit competent bacteria (INVαF': endal, recAl, hsdRl7(r-k, m+k), supE44, λ-, thi-1, gyrA, relA1, Φ80lacZαΔM15Δ(lacZYA-argF), deoR+, F') were thawed on ice and 2 μl of 0.5 M β-mercaptoethanol were added to each tube. 2 μl from each ligation were added to each tube of competent cells (50 μl), mixed without vortexing, and incubated on ice for 30 min. Tubes were then placed in 42° C. bath for exactly 30 sec., before being returned to ice for 2 min. 450 μl of SOC media (Sambrook et al., 1989, supra) were then added to each tube which were then shaken at 37° C. for 1 hr. Bacteria were then pelleted, resuspended in ~200 μl SOC and plated on Luria broth agar plates containing X-gal and 60 μg/ml ampicillin and incubated overnight at 37° C. White colonies were then picked and screened for inserts using PCR.

A master mix containing 2 μl 10×PCR buffer, 1.6 μl 2.5 mM dNTP's, 0.1 μl 25 mM MgCl$_2$, 0.2 μl M13 reverse primer (100 ng/μl), 0.2 μl M13 forward primer (100 ng/μl), 0.1 μl AmpliTaq (Perkin-Elmer), and 15.8 μl H$_2$O was made. 40 μl of the master mix were aliquoted into tubes of a 96 well plate, and whole bacteria were added with a pipette tip prior to PCR. The PCR machine (Perkin-Elmer 9600) was programmed for insert screening as follows:

| | | |
|---|---|---|
| | 94° C. | 2 min. |
| | *94° C. | 15 sec. |
| | *47° C. | 2 min. |
| * = X35 | *ramp 72° C. | 30 sec. |
| | *72° C. | 30 sec. |
| | 72° C. | 10 min. |
| | 4° C. hold | |

Reaction products were eluted on a 2% agarose gel and compared to vector control. Colonies with vectors containing inserts were purified by streaking onto LB/Amp plates. Vectors were isolated from such strains and subjected to sequence analysis, using an Applied Biosystems Automated Sequencer (Applied Biosystems, Inc. Seattle, Wash.).

Northern analysis: Northern analysis was performed to confirm the differential expression of the genes corresponding to the amplified bands. The probes used to detect mRNA were synthesized as follows: typically 2 μl amplified band (~30 ng), 7 μl H$_2$O, and 2 μl 10×Hexanucleotide mix (Boehringer-Mannheim) were mixed and heated to 95° C. for 5 min., and then allowed to cool on ice. The volume of the amplified band can vary, but the total volume of the band plus H$_2$O was always 9 μl. 3 μl dATP/dGTP/dTTP mix (1:1:1 of 0.5 mM each), 5 μl α$^{32}$P dCTP 3000 Ci/mM (50 μCi total) (Amersham, Arlington Heights, Ill.), and 1 μl Klenow (2 units) (Boehringer-Mannheim) were mixed and incubated at 37° C. After 1 hr., 30 μl TE were added and the reaction was loaded onto a Biospin-6™ column (Biorad, Hercules, Calif.), and centrifuged. A 1 μl aliquot of eluate was used to measure incorporation in a scintillation counter with scintillant to ensure that $10^6$cpm/μl of incorporation was achieved.

The samples were loaded onto a denaturing agarose gel. A 300 ml 1% gel was made by adding 3 g of agarose (SeaKem™ LE, FMC BioProducts, Rockland, Me.) and 60 ml of 5×MOPS buffer to 210 ml sterile H2O. 5×MOPS buffer (0.1M MOPS (pH 7.0), 40 mM NaOAc, 5 mM EDTA (pH 8.0)) was made by adding 20.6 g of MOPS to 800 ml of 50 mM NaOAc (13.3 ml of 3M NaOAc pH 4.8 in 800 ml sterile H$_2$O); then adjusting the pH to 7.0 with 10M NaOH; adding 10 ml of 0.5M EDTA (pH8.0); and adding H$_2$O to a final volume of 1L. The mixture was heated until melted, then cooled to 50° C., at which time 5 μl ethidium bromide (5 mg/ml) and 30 ml of 37% formaldehyde of gel were added. The gel was swirled quickly to mix, and then poured immediately.

2 μg RNA sample, 1× final 1.5× RNA loading dyes (60% formamide, 9% formaldehyde, 1.5×MOPS, 0.075% XC/BPB dyes) and H$_2$O were mixed to a final volume of 40 μl. The tubes were heated at 65° C. for 5 min. and then cooled on ice. 10 μg of RNA MW standards (New England Biolabs, Beverly, Mass.) were also denatured with dye and loaded onto the gel. The gel was run overnight at 32V in MOPS running buffer.

The gel was then soaked in 0.5 μg/ml Ethidium Bromide for 45 min., 50 mM NaOH/0.1 M NaCl for 30 min., 0.1 M Tris pH 8.0 for 30 min., and 20×SSC for 20 min. Each soaking step was done at r.t. with shaking. The gel was then photographed along with a fluorescent ruler before blotting with Hybond-N membrane (Amersham), according to the methods of Sambrook et al., 1989, supra, in 20×SSC overnight.

Northern blot hybridizations were carried out as follows: for pre-hybridization, the blot was placed into roller bottle containing 10 ml of rapid-hyb solution (Amersham), and placed into 65° C. incubator for at least 1 hr. For hybridization, 1×10⁷ cpm of the probe was then heated to 95° C., chilled on ice, and added to 10 ml of rapid-hyb solution. The prehybridization solution was then replaced with probe solution and incubated for 3 hr at 65° C. The following day, the blot was washed once for 20 min. at r.t. in 2×SSC/0.1% SDS and twice for 15 min. at 65° C. in 0.1×SSC/0.1% SDS before being covered in plastic wrap and put down for exposure.

RT-PCR Analysis: RT-PCR was performed to detect differentially expressed levels of mRNA from the genes corresponding to amplified bands. First strand synthesis was conducted by mixing 20 μl DNased RNA (~2 μg), 1 μl oligo dT (Operon) (1 μg), and 9.75 μl H$_2$O. The samples were heated at 70° C. for 10 min., and then allowed to cool on ice. 10 μl first strand buffer (Gibco/BRL), 5 μl 0.1M DTT, 1.25 μl 20 mM dNTP's (500 μM final), 1 μl RNAsin (40 units/μl) (Boehringer Mannleim), and 2 μl Superscript Reverse Transcriptase (200 units/μl) (Gibco/BRL) were added to the reaction, incubated at 42° C. for 1 hr., and then placed at 85° C. for 5 min., and stored at −20° C.

PCR was performed on the reverse transcribed samples. Each reaction contained 2 μl 10×PCR buffer, 14.5 μl H$_2$O, 0.2 μl 20 mM dNTP's (200 μM final), 0.5 μl 20 μM forward primer (0.4 μM final), 0.5 μl 20 μM reverse primer (0.4 μM final), 0.3 μl AmpliTaq polymerase (Perkin-Elmer/Cetus), 2 μl cDNA dilution or positive control (~40 pg). The specific primers used in each experiment are provided in the Description of the Figures in Section 4, above. Samples were placed in the PCR 9600 machine at 94° C. (hot start), which was programmed as follows:

|        |         |                         |
|--------|---------|-------------------------|
|        | 94° C.  | 2 min. (samples loaded) |
|        | *94° C. | 45 sec.                 |
| * = 35x| *55° C. | 45 sec.                 |
|        | *72° C. | 2 min.                  |
|        | 72° C   | 5 min.                  |
|        | 4° C.   | hold                    |

Reactions were carried out on cDNA dilution series and tubes were removed at various cycles from the machine during 72° C. step. Reaction products were eluted on a 1.8% agarose gel and visualized with ethidium bromide.

Gene Retrieval: Amplified sequences, which contained portions of the genes, were subcloned and then used individually to retrieve a cDNA encoding the corresponding gene. Probes were prepared by isolating the subcloned insert DNA from vector DNA, and labeling with $^{32}$P as described above in Section 6.1.2. Labeled insert DNA containing fchd602 sequences was used to probe a cDNA library prepared from human macrophage cell line U937. Labeled insert DNA containing fchd605 sequences was used to probe a cDNA library prepared from human primary blood monocytes. The cDNA libraries were prepared and screened according to methods routinely practiced in the art (see Sambrook et al., 1989, supra). Plaques from the libraries that were detected by the probes were isolated and the cDNA insert within the phage vector was sequenced.

The RACE procedure kit was used either as an alternative to cDNA library screening, or, when the cDNA library did not yield a clone encoding the full-length gene, to obtain adjacent sequences of the gene. The procedure was carried out according to the manufacturer's instructions (Clontech, Palo Alto, Calif.; see also: Chenchik, et al., 1995, CLONTECHniques (X) 1: 5–8; Barnes, 1994, Proc. Natl. Acad. Sci. USA 91: 2216–2220; and Cheng et al., Proc. Natl. Acad. Sci. USA 91: 5695–5699). Primers were designed based either on amplified sequences, or on sequences obtained from isolates from the cDNA libraries. Template mRNA for fchd605 was isolated from human primary blood monocytes.

6.1.3. Chromosomal Localization of Target Genes

Once the nucleotide sequence has been determined, the presence of the gene on a particular chromosome is detected. Oligonucleotide primers based on the nucleotide sequence of the target gene are used in PCR reactions using individual human chromosomes as templates. Individual samples of each the twenty-three human chromosomes are commercially available (Coriel Institute for Medical Research, Camden, N.J.). The chromosomal DNA is amplified according to the following conditions: 10 ng chromosomal DNA, 2 μl 10×PCR buffer, 1.6 μl 2.5 mM dNTP's, 0.1 μl 25 mM MgCl$_2$, 0.2 μl reverse primer (100 ng/μl), 0.2 μl forward primer (100 ng/μl), 0.1 μl Taq polymerase, and 15.8 μl H$_2$O. Samples are placed in the PCR 9600 machine at 94° C. (hot start), which is programmed as follows:

|         |         |                         |
|---------|---------|-------------------------|
|         | 94° C.  | 2 min. (samples loaded) |
|         | *94° C. | 20 sec.                 |
| * = 35x | *55° C. | 30 sec.                 |
|         | *72° C. | 30 sec.                 |
|         | 72° C.  | 5 min.                  |
|         | 4° C.   | hold                    |

6.2. Results

Differential display was performed on monocytes treated with oxidized LDL and untreated monocytes. Bands corresponding to fchd602 and fchd605 were detected as up-regulated by oxidized LDL, as compared with the untreated monocytes. The up-regulation was confirmed by northern blot analysis.

The fchd602 gene produced a 2.5 kb mRNA that was up-regulated after 5 hours of treatrnent with oxidized LDL, minimally oxidized LDL, and lysophosphatidylcholine. No message was detected in untreated or native LDL treated control monocytes. The amplified DNA sequence was used to recover a cDNA of approximately 875 bp comprising an open reading frame encoding approximately 182 amino acids. The DNA sequence and encoded amino acid sequence of this cDNA from the fchd602 gene is shown in FIGS. 4A–4B. The open reading frame has 88% sequence similarity to the rat Cl-6 gene, which is induced in regenerating rat liver, is insulin inducible, and also contains multiple transmembrane domains (Diamond, R. H., et al., 1993, J. Biol. Chem. 268: 15185–15192).

The fchd605 gene produced a 1.5 kb mRNA that is up-regulated after 5 hours treatment with oxidized LDL, and to a lesser degree with native LDL, as compared to untreated monocytes. The amplified DNA was sequenced and used to recover a cDNA of approximately 2.2 kb, which was sequenced to reveal a partial open reading frame of approximately 258 bp, encoding approximately 86 amino acids. The DNA sequence and encoded amino acid sequence from the fchd605 gene is shown in FIGS. 5A–5B. The sequence has similarity to the mouse gly96 gene, which encodes a cytokine inducible glycosylated protein expressed in mouse lung, testes, and uterus.

7. EXAMPLE

Identification of Genes Differentially Expressed in Response to Paradigm D: Endothelial Cell Shear Stress According to the invention, differential display was used to detect genes that are differentially expressed in endothelial cells that were subjected to fluid shear stress in vitro. Shear stress is thought to be responsible for the prevalence of atherosclerotic lesions in areas of unusual circulatory flow. Using the method of Paradigm D, three novel DNA sequences were identified.

The fchd531 gene is down-regulated in endothelial cells under both turbulent and laminar shear stress, as compared to the static control. The fchd531 gene encodes a novel 570 amino acid polypeptide, and has 94% sequence similarity to the mouse penta zinc finger gene (Pzf), which has not been published, but is contained in the GenBank sequence data base under accession no U05343.

The fchd540 gene is up-regulated in endothelial cells under laminar shear stress, but is not up-regulated by IL-1 treatment. The fchd540 gene encodes a novel intracellular protein which has sequence similarity to the Drosophila Mad protein (Sekelsky et al., 1995, Genetics 139: 1347–1358).

The fchd545 gene is down-regulated in endothelial cells under laminar shear stress as compared to endothelial cells under turbulent shear stress and static control endothelial cells. The fchd545 gene encodes an 848 amino acid polypeptide which has 73% sequence similarity to the human Voltage-dependent Anion Channel protein (Blachly-Dyson, E., et al., 1993, J. Biol. Chem. 268:1835–1841.). The fchd545 gene is also expressed in the human heart, smooth muscles, and testes.

The up-regulation of the fchd540 gene and down-regulation of the fchd531 and fchd545 genes in shear stressed endothelial cells provides a fingerprint for the study of cardiovascular diseases, including but not limited to atherosclerosis, ischemia/reperfusion, hypertension, and restenosis. The fact that one of these genes, fchd540, is not up-regulated under Paradigm C (IL-1 induction) provides an extremely useful means of distinguishing and targeting physiological phenomena specific to shear stress.

Furthermore, as a transmembrane protein, the fchd545 gene product can be readily accessed or detected on the endothelial cell surface by other compounds. It provides, therefore, an excellent target for detection of cardiovascular disease states in diagnostic systems, as well as in the monitoring of the efficacy of compounds in clinical trials. Furthermore, the extracellular domains of this gene product provide targets which allow for designing especially efficient screening systems for identifying compounds that bind to them. Such compounds can be useful in treating cardiovascular disease by modulating the activity of the transmembrane gene product.

7.1. Materials and Methods

Primary cultures of HUVEC's were established from normal term umbilical cords as described (In Progress in Hemostasis and Thrombosis, Vol. 3, P. Spaet, editor, Grune & Stratton Inc., New York, 1–28). Cells were grown in 20% fetal calf serum complete media (1989, J. Immunol. 142: 2257–2263) and passaged 1–3 times before shear stress induction.

For induction, second passage HUVEC's were plated on tissue culture-treated polystyrene and subjected to 10 dyn/$cm^2$ laminar flow for 1 and 6 hr. as described (1994, J. Clin. Invest. 94: 885–891) or 3–10 dyn/$cm^2$ turbulent flow as previously described (1986, Proc. Natl. Acad. Sci. U.S.A. 83: 2114–2117). RNA was isolated as described, above, in Section 6.1. Differential display, Northern analysis, RT-PCR, subcloning, and DNA sequencing were carried out as described, above, in Section 6.1.2. Specific primers used in differential display were as follows:

fchd531: for-$T_{11}$XA (SEQ ID NO:16) and rev-AGACGTCCAC (SEQ ID NO:17)

fchd540: for-$T_{11}$XA (SEQ ID NO:16) and rev-ACTTCGCCAC (SEQ ID NO:18)

fchd545: for-$T_{11}$XC (SEQ ID NO:13) and rev-TCGGACGTGA (SEQ ID NO:19)

Amplified sequences, which contained portions of the genes, were subcloned and then used individually to retrieve a cDNA encoding the corresponding gene. Probes were prepared by isolating the subcloned insert DNA from vector DNA, and labeling with $^{32}P$ as described above in Section 6.1.2. Labeled insert DNA was used to probe cDNA library prepared from shear stress induced endothelial cells. The library was prepared and probed using methods routinely practiced in the art (see Sambrook et al, 1989, supra). Plaques from the libraries that were detected by the probes were isolated and the cDNA insert within the phage vector was sequenced.

The RACE procedure kit was used either as an alternative to cDNA library screening, or, when the cDNA library did not yield a clone encoding the full-length gene, to obtain adjacent sequences of the gene. The procedure was carried out according to the manufacturer's instructions (Clontech, Palo Alto, Calif.; see also: Chenchik, et al., 1995, CLONTECHniques (X) 1: 5–8; Barnes, 1994, Proc. Natl. Acad. Sci. USA 91: 2216–2220; and Cheng et al., Proc. Natl. Acad. Sci. USA 91: 5695–5699). Primers were designed based either on amplified sequences, or on sequences obtained from isolates from the cDNA libraries. Template mRNA was isolated from shear stressed HUVEC's.

Northern blot analysis of RNA extracted from various human organs and tissues was performed using commercially available pre-blotted filters (Clontech, Palo Alto, Calif.).

7.2. Results

An amplified fchd531 fragment obtained from differential display was subcloned and sequenced, and used to obtain a 1.9 kb cDNA containing the entire fchd531 coding region. The DNA sequence and encoded amino acid sequence of the novel fchd531 gene is shown in FIGS. 1A–1D. The fchd531 gene encodes a 570 amino acid polypeptide, and has 94% sequence similarity to the mouse penta zinc finger gene (Pzf) (GenBank accession number U05343). Northern analysis of HUVEC's which were subjected turbulent and laminar shear stress demonstrated that the fchd531 gene produces an approximately 5 kb message which is down-regulated under laminar shear stress, but not turbulent shear stress, compared with the static control.

The fchd540 gene was detected as an up-regulated message under shear stress. The amplified fragment was used to probe a Northern blot containing samples from HUVECs treated with laminar shear stress. A 4.4 kb fchd540 mRNA is up-regulated after 6 hours treatment with laminar shear stress. The fchd540 gene is not induced by IL-1 by the method of Paradigm C, (Section 5.1.1.5, above). The amplified fragment was sequenced and used to obtain a 2.7 kb cDNA containing the entire fchd540 coding region. The DNA sequence and encoded amino acid sequence from the fchd540 gene is shown in FIGS. 2A–2E. The fchd540 gene encodes a 426 amino acid polypeptide and has sequence similarity to the Drosophila Mad gene (Sekelsky et al., 1995, Genetics 139: 1347–1358).

The fchd545 gene was detected as a down-regulated message under shear stress. Northern analysis revealed that the fchd545 gene produces a 1.4 kb message which is down regulated by turbulent shear stress, but not by laminar shear stress, as compared with static control. The amplified fragment was sequenced and used to isolate a 1.4 kb cDNA containing the complete fchd545 coding sequence. The DNA sequence and encoded amino acid sequence of the fchd545 gene is shown in FIGS. 3A–3C. The fchd545 gene encodes a 283 amino acid polypeptide which has 73% sequence similarity to the human Voltage-dependent Anion Channel (Blachly-Dyson, E., et al., 1993, J. Biol. Chem. 268: 1835–1841). Northern analysis of a commercially available (Clontech, Palo Alto, Calif.) northern blot revealed that the fchd545 gene is expressed in human heart, smooth muscle, and testes.

8. EXAMPLE

Use of Genes Under Paradigm A as Surrogate Markers in Clinical Trials

According to the invention, the fingerprint profile derived from any of the paradigms described in Sections 5.1.1.1 through 5.1.1.6 may be used to monitor clinical trials of drugs in human patients. The fingerprint profile, described generally in Section 5.5.4, above, indicates the characteristic pattern of differential gene regulation corresponding to a particular disease state. Paradigm A, described in Section 5.1.1.1, and illustrated in the example in Section 6, above, for example, provides the fingerprint profile of monocytes under oxidative stress. The target genes, therefore, serve as surrogate markers by giving an indicative reading of the physiological response of monocytes to the uptake of oxidized LDL. Accordingly, the influence of anti-oxidant drugs on the oxidative potential may be measured by performing differential display on the monocytes of patients undergoing clinical tests.

8.1. Treatment of Patients and Cell Isolation

Test patients may be administered compounds suspected of having anti-oxidant activity. Control patients may be given a placebo.

Blood may be drawn from each patient after a 12 hour period of fasting and monocytes may be purified as described, above, in Section 7.1.1. RNA may be isolated as described in Section 6.1.1, above. Primers may then be designed for amplification based on the DNA sequence of target genes identified as up-regulated, such as fchd602 and fchd605, or down-regulated under Paradigm A.

8.2. Analysis of Samples

RNA may be subjected to differential display analysis as described in Section 6.1.2, above. A decrease in the physiological response state of the monocytes is indicated by a decreased intensity of those bands corresponding to fchd602 and fchd605, which were up-regulated by oxidized LDL under Paradigm A, as described in Section 6.2, above.

9. EXAMPLE

Imaging of a Cardiovascular Disease Condition

According to the invention, differentially expressed gene products which are localized on the surface of affected tissue may be used as markers for imaging the diseased or damaged tissue. Conjugated antibodies that are specific to the differentially expressed gene product may be administered to a patient or a test animal intravenously. This method provides the advantage of allowing the diseased or damaged tissue to be visualized non-invasively.

For the purposes of illustration, this method is described in detail for the fchd602 gene product. The principles and techniques can be applied to any transmembrane target gene product, including, for example, the fchd545 gene product.

9.1. Monoclonal Conjugated Antibodies

The differentially expressed surface gene product, such as the fchd602 gene product, is expressed in a recombinant host and purified using methods described in Section 5.4.2, above. Preferably, a protein fragment comprising one or more of the extracellular domains of the fchd602 product is produced. Once purified, it is be used to produce $F(ab')_2$ or Fab fragments, as described in Section 5.4.3, above. These fragments are then labelled with technetium-99m ($^{99m}Tc$) using a conjugated metal chelator, such as DTPA as described in section 5.8.3, above.

9.2. Administration and Detection of Imaging Agents

Labeled MAb may be administered intravenously to a patient being diagnosed for atherosclerosis, restenosis, or ischemia/reperfusion. Sufficient time is allowed for the detectably-labeled antibody to localize at the diseased or damaged tissue site (or sites), and bind to the fchd602 gene product. The signal generated by the label is detected by aphotoscanning device. The detected signal is then converted to an image of the tissue, revealing cells, such as monocytes, in which fchd602 gene expression is up-regulated.

10. Polyclonal Antibodies to Target Gene Peptide Sequences

Peptide sequences corresponding to the indicated amino acid sequences of cDNAs were selected and submitted to Research Genetics (Huntsville, Ala.) for synthesis and antibody production. Peptides were modified as described (Tam, J. P., 1988, Proc. Natl. Acad. Sci. USA 85: 5409–5413; Tam, J. P., and Zavala, F., 1989, J. Immunol. Methods 124: 53–61; Tam, J. P., and Lu, Y. A., 1989, Proc. Natl. Acad. Sci. USA 86: 9084–9088), emulsified in an equal volume of Freund's adjuvant and injected into rabbits at 3 to 4 subcutaneous dorsal sites for a total volume of 1.0 ml (0.5 mg peptide) per immunization. The animals were boosted after 2 and 6 weeks and bled at weeks 4, 8, and 10. The blood was allowed to clot and serum was collected by centrifugation.

The peptides used are summarized below:

fchd545 Peptide Antigens

| Name | Position | Sequence |
| --- | --- | --- |
| fchd545.1 | 48–63 | YTDTGKASGNLETKYK (SEQ ID NO:43) |
| fchd545.2 | 107–121 | TGKKSGKLKASYKRD (SEQ ID NO:44) |

11. EXAMPLE

The RCHD534 and FCHD540 Gene Products Interact

The novel fchd540 gene and its nucleotide sequence is described in Section 7, above. The fchd540 gene shares homology with the Drosophila Mad gene. The rchd534 gene (described in Applicant's co-pending Application No. 08/485,573, filed Jun. 7, 1995, which is incorporated by reference in its entirety herein) is another gene that is up-regulated in endothelial cells by shear stress. Subsequent to Applicant's discovery of the rchd534 gene, the rchd534 gene has been referred to in published reports as Smad6. As used herein, rchd534 and Smad6 may be used interchangeably. The DNA and encoded amino acid sequence of the rchd534 gene is shown in FIGS. 6A–6D. The rchd534 gene was deposited in the Agricultural Research Service Culture Collection (NRRL) in microorganism FCHD534 on Jun. 6,1995 and assigned the NRRL Accession No. B-21459. The rchd534 gene also shares homology with the Drosophila Mad gene. Mad genes have been shown to play a role in the TGF-β signalling pathway (Sekelsky et al., 1995, Genetics 139: 1347–1358; Chen et al., 1996, Nature 383: 691–696; Serra, et al., 1996, Nature Medicine 2: 390–391). TGF-β signalling is considered to be beneficial to atherosclerosis and restenosis (Border et al., 1995, Nature Medicine 1: 1000; Grainger, et al., 1995, Nature Medicine 1: 1067–1073; Kojima, et al., 1991, J. Cell Biol. 113: 1439–1445; Nikol, et al., 1992, J. Clin. Invest. 90: 1582–1592).

The data described below demonstrate that the rchd534 and fchd540 proteins interact with one another; and this interaction may lead to the inhibition of TGF-β signalling. Furthermore, the expression of these two genes, as described below, is specific to endothelial cells. Because these two genes 1) are both expressed specifically in endothelial cells, 2) are both up-regulated in endothelial cells under certain conditions, 3) encode MAD proteins that interact with one another in endothelial cells, and 4) inhibit TGF-β signalling (which is considered to be beneficial to atherosclerosis), rchd534 and fchd540 proteins are attractive targets for therapeutic intervention in cardiovascular disease. In particular, treatment regimens that inhibit the interaction or activity of the rchd534 and fchd540 proteins can be beneficial for the treatment cardiovascular disease.

Further analyses demonstrated that the rchd534 protein interacts with itself to form a homodimer. Thus, treatment regimens that inhibit the interaction of the rchd534 protein with itself can be beneficial for the treatment cardiovascular disease.

In addition, the analyses described below demonstrated novel interactions of both the rchd534 and fchd540 proteins with other proteins known to be involved in the TGF-β signalling pathway. The protein members of the TGF-β signalling pathway tested included MADR1 (Hoodless et al., 1996, Cell 85:489–500), MADR2 (Eppert et al., 1996, Cell 86: 543–552), DPC4 (Raftery et al., 1988, Genetics 139: 241–254), TβRI, TSR1, ActRIb, ALK3, and ALK6 (Wieser et al., 1995, *EMBO J*. 14: 2199–2208). For example, the rchd534 protein interacts strongly in endothelial cells with MADR1, MADR2, DPC4, and weakly in 293 (human embryonic kidney) cells with activated forms of receptors TβRI and ActRI. The fchd540 protein interacts strongly in 293 cells with activated forms of receptors TβRI and ALK6.

In the absence of transfected rchd543 and fchd540 genes, transfected MADR1 or transfected MADR2 mediated a 20-fold induction of a TGF-β inducible promoter in BAECs. Co-expression of either transfected rchd534 or transfected rchd540 in this system eliminated the induction, and also prevented the localization of MADR2 in the nucleus in response to TGF-β signalling. Therefore, treatment regimens that inhibit the interaction of the rchd534 and fchd540 proteins with other proteins involved in the TGF-β pathway also can be beneficial for the treatment cardiovascular of disease. As described above, the expression of rchd534 and fchd540 is specific, within arterial tissue, to endothelial cells. Accordingly, the rchd534 and rchd540 genes may be targets for intervention in a variety of inflammatory and fibroproliferative disorders that involve endothelial cells, including, but not limited to, cancer, angiogenesis, inflammation, and fibrosis.

11.1. Materials and Methods

11.1.1. Yeast Strains, Media, and Microbiological Techniques

Standard yeast media including synthetic complete medium lacking L-leucine, L-tryptophan, and L-histidine were prepared and yeast genetic manipulations were performed as described (Sherman, 1991, Meth. Enzymol., 194:3–21). Yeast transformations were performed using standard protocols (Gietz et al., 1992, Nucleic Acids Res., 20:1425. Ito et al., 1983, J. Bacteriol., 153:163–1 68). Plasmid DNAs were isolated from yeast strains by a standard method (Hoffman and Winston, 1987, Gene, 57:267–272).

11.1.2. Plasmid and Yeast Strain Construction

The coding region of human fchd540 was amplified by PCR and cloned in frame into pGBT9 (Bartel et al., 1993, Cellular Interactions in Development. pp. 153–159) resulting in plasmid pGBT9-fchd540. pGBT9-fchd540 was transformed into two-hybrid screening strain HF7c and one resulting transformant was designated TB35.

11.1.3. Two-hybrid Screening

Two-hybrid screening was carried out essentially as described (Bartel et al., 1993, supra) using TB35 as the recipient strain and a human breast two-hybrid library.

11.1.4. Paper Filter Beta-galactosidase Assays

The paper filter beta-galactosidase (beta-gal) assay was performed essentially as previously described (Brill et al., 1994, Mol. Biol. Cell 5: 297–312).

11.2. Results

11.2.1. Strong Physical Interaction of RCHD534 and FCHD540 Measured by Two-hybrid Assay The fchd540 coding sequence was amplified by PCR and cloned into pGBT9 creating a GAL4 DNA-binding domain-fchd540 fusion gene. The screening strain HF7c was transformed with this construct. The rchd534 coding sequence was cloned into pGAD424 (Bartel et al., 1993, supra) creating a GAL4 transcriptional activation domain-rchd534 fusion gene, which was then used to transform strain Y187.

Yeast expression plasmids encoding the GAL4 DNA-binding domain either alone or fused in frame to fchd540, rchd534, Drosophilia MAD, DPC4, or p53 were transformed into MATa two-hybrid screening strain HF7c. Yeast expression plasmnids encoding the GAL4 transcriptional activation domain alone and GAL4 activation domain fusions to rchd534 and SV40 were transformed into MATα two-hybrid screening strain Y1 87. p53 and SV40 interact with each other and should not interact with the experimental proteins. The HF7c transformants were propagated as stripes on semisolid synthetic complete medium lacking L-tryptophan and the Y187 transformants were grown as stripes on semisolid synthetic complete medium lacking L-leucine. Both sets of stripes were replica plated in the form of a grid onto a single rich YPAD plate and the haploid strains of opposite mating types were allowed to mate overnight at 30° C. The yeast strains on the mating plate were then replica plated to a synthetic complete plate lacking L-leucine and L-tryptophan to select for diploids and incubated at 30° C. overnight. Diploid strains on the synthetic complete plate lacking L-leucine and L-tryptophan were replica plated to a synthetic complete plate lacking L-leucine, L-tryptophan, and L-histidine to assay HIS3 expression and a paper filter on a synthetic complete plate lacking L-leucine and L-tryptophan. The next day the paper filter was subjected to the paper filter beta-galactosidase assay to measure expression of the lacZ reporter gene. HIS3 expression was scored after 3 days of growth at 30° C. The results are shown in Table 3.

The rchd534 fish protein was found to interact strongly with the fchd540 bait protein and not to interact with the rchd534, MAD, DPC4, p53, and GAL4 DNA binding domain bait proteins. This result demonstrated that rchd534 and fchd540 strongly physically interact with each other with significant specificity.

11.2.2. Identification of Proteins that Physically Interact with FCHD540

The fchd540 coding sequence was amplified by PCR and cloned into pGBT9 (Bartel et al., 1993, supra) creating a GAL4 DNA-binding domain-fchd540 fusion gene. HF7c was transformed with this construct resulting in strain TB35. TB35 grew on synthetic complete medium lacking L-tryptophan but not on synthetic complete medium lacking L-tryptophan and L-histidine demonstrating that the GAL4 DNA-binding domain-fchd540 fusion does not have intrinsic transcriptional activation activity.

TB35 was transformed with the human breast two-hybrid library and 5 million transformants were obtained. The transformants were plated on synthetic complete medium lacking L-leucine, L-tryptophan, and L-histidine and yeast colonies that both grew on synthetic complete medium lacking L-leucine, L-tryptophan, and L-histidine and expressed the beta-galactosidase reporter gene were identified. The 30 strains with the strongest beta-galactosidase induction were characterized. Library plasmids were isolated from these strains, and the 5' ends of all of the cDNA inserts were sequenced.

11.2.3. Retransformation and Specificity Testing of Tchv03A and Tchvr4A

Two of the plasmids that encoded the strongest interactors were found to contain rchd534 cDNAs. Plasmid tchv03A was found to encode amino acids 17–235 of rchd534 and plasmid tchvR4A was found to encode amino acids 25–235 of rchd534.

It was confirmed that these rchd534 cDNAs encode proteins that physically interact specifically with fchd540. Yeast expression plasmids encoding the GAL4 DNA-binding domain either alone or fused in frame to fchd540, rchd534, Drosophila MAD, DPC4, and p53 were transformed into MATa two-hybrid screening strain HF7c. Yeast expression plasmids encoding the GAL4 transcriptional activation domain (GAL4 AD) alone and GAL4 activation domain fusions to tchv03a, tchvR4A and SV40 were transformed into MATα two-hybrid screening strain Y1 87. p53 and SV40 interact with each other and should not interact with the experimental proteins. The HF7c transformants were propagated as stripes on semi-solid synthetic complete medium lacking L-leucine. Both sets of stripes were replica plated in the form of a grid onto a single rich YPAD plate and the haploid strains of opposite mating types were allowed to mate overnight at 30° C. The yeast strains on the mating plate were then replica plated to a synthetic complete plate lacking L-leucine and L-tryptophan to select for diploids and incubated at 30° C. overnight. Diploid strains on the synthetic complete plate lacking L-leucine and L-tryptophan were replica plated to a synthetic complete plate lacking L-leucine, L-tryptophan, and L-histidine to assay HIS3 expression and a paper filter on a synthetic complete plate lacking L-leucine and L-tryptophan. The next day the paper filter was subjected to the paper filter beta-galactosidase assay to measure expression of the lacZ reporter gene. HIS3 expression was scored after 3 days of growth at 30° C. The results are shown in the table below. The strength or absence of physical interaction between each combination of test proteins is listed. Strong interactions are defined as interactions that cause the activation of both the HIS3 and lacZ reporter genes.

TABLE 3

| | cDNA-GAL4 Activation Domain Fusion Tested | | | | |
|---|---|---|---|---|---|
| | rchd534 | tchv03A | tchvR4A | SV40 | GAL4 AD alone |
| GAL4 DNA-Binding Domain Fusions | | | | | |
| fchd540 | Strong | Strong | Strong | None | None |
| rchd534 | None | None | None | None | None |
| Dros. MAD | None | None | None | None | None |
| DPC4 | None | None | None | None | None |
| p53 | None | None | None | Strong | None |
| GAL4 DNA-Binding Domain alone | None | None | None | None | None |

The tchv03A and tchvR4A fish proteins were found to interact strongly with the fchd540 bait protein and to not interact with the rchd534, MAD, DPC4, p53, and GAL4 DNA binding domain bait proteins. These results confirm the result that the rchd534 and fchd540 proteins interact strongly with each other.

11.3. Further Analysis of RCHD534 and FCHD540 Function

The significance of the rchd534/fchd540 protein interaction was confirmed by examination of their expression and activity in human cells and animal models.

11.3.1. Chromosomal Localization

The rchd534 gene was localized to chromosome 15 and the fchd540 gene was localized to chromosome 18, regions of the human genome that contain other MAD homologues. These regions of the human genome have also been implicated in the pathogenesis of several human malignancies.

11.3.2. Tissue Expression Patterns

The expression patterns were examined using in situ hybridization techniques. Fluorescently labeled DNA probes of both the rchd534 and fchd540 genes were used to probe human carotid endartectomy samples. The expression of rchd534 and fchd540 was specific to endothelial cells lining the luminal surface of the carotid artery. In addition, a rabbit polyclonal antiserum generated against the rchd534 gene product prominently and selectively stained the endothelium present in large vessels such as human coronary arteries as well as smaller vessels present within human myocardium. Neither gene showed expression in any other cell type present in the arterial tissue sample, including smooth muscle cells and macrophages.

Expression patterns of both genes were also examined in response to certain stimulus. Both genes are selectively upregulated under the steady laminar shear stress (LSS) paradigm, but not under the turbulent shear stress paradigm or in response to stimulus by the cytokines rhIL-1β, TNFα, IFNγ or active TGFβ as measured in HUVEC cells. Thus, the rchd534 and the fchd540 genes appear to be selectively responsive to a LSS stimulus, manifesting no response to a non-laminar fluid mechanical stimulus, nor any other humoral stimuli tested. Thus, given that these two genes are: (1) localized to a region of the human genome that has been implicated in the pathogenesis of several human malignancies; (2) specifically expressed in a cell-type that is found only in vascular tissue, including atherosclerotic plaques; (3) up-regulated under the steady laminar shear stress cardiovascular disease paradigm; and (4) specifically inhibit TGF-β signalling indicate that rchd534 and fchd540 are excellent and specific targets for therapeutic intervention in the treatment of fibroproliferative and oncogenic disorders including tumor growth and vascularization.

11.3.3. Cellular Localization

The cellular localization of the rchd534 and fchd540 proteins in bovine aortic endothelial cells (BAECs) was examined in relationship to other proteins involved in the TGF-β signalling pathway. In all experiments, the rchd534 and fchd540 proteins were located in the cytoplasm. MADR2 was located in the cytoplasm when transfected alone and in the nucleus when co-transfected with activated TβRI or when TGF-β was added to the culture medium. Co-transfection of rchd534 or fchd540 with MADR2 prevented the localization of MADR2 in the nucleus in response to TGF-β signalling.

11.3.4. Protein Interaction in Human Cells

The interaction of the rchd534 and fchd540 proteins, observed in yeast cells as described above, was tested in mammalian endothelial cell tissue culture. Either bovine aortic endothelial cells (BAECs) or 293 cells (human embryonic kidney cells, ATCC Accession No. CRL-1573) were transfected with constructs encoding both the rchd534 and fchd540 proteins, each fused to a different flag peptide allowing for specific immunoprecipitation. The rchd534 and fchd540 proteins were found to co-immunoprecipitate as heterodimers in extracts produced from both 293 cells and BAECs. The co-immunoprecipitation of rchd534 and fchd540 further supports that these proteins interact in human cells that are physiologically relevant to cardiovascular disease.

The ability of the rchd534 and fchd540 proteins to interact with themselves and with other protein members of the TGF-β signalling pathway (MADR1, MADR2, DPC4, TbR1, TSR1, ActR1b, ALK3, ALK6), was tested using this co-inmunoprecipitation method. Each gene was transfected alone and in various combinations with other TGF-β pathway genes in either 293 cells or BAECs. The rchd534 protein formed homodimers in 293 cells and BAECs. The fchd540 protein did not form homodimers in 293 cells or BAECs. As mentioned above, the rchd534 and fchd540 proteins formed heterodimers in 293 cells and BAECs. This interaction is about 50 fold stronger in BAECs than 293 cells based on equal amounts of protein. However, the rchd534-fchd540 protein interaction was significantly less avid than the rchd534 protein's interaction with itself.

The rchd534 protein interacted with MADR1, MADR2, and DPC4 in 293 cells and BAECs. The strength of MADR1 and MADR2 interactions was about the same between 293 cells and BAECs and much greater in BAECs for DPC4. The fchd540 protein interacted very weakly with MADR1, MADR2, and DPC4 in 293 cells. The rchd534 protein interacted strongly with activated forms of TβRI and ActRI and weakly with activated ALK6 in 293 cells. The fchd540 protein interacted strongly with activated TβRI and ALK6 receptors, and weakly with activated forms of TSRI, ALK3, and ActRIb in 293 cells. Thus, in addition to the interaction of the rchd534 and fchd540 proteins, the interaction of the rchd534 protein with itself, as well as the interaction of the rchd534 protein and the fchd540 protein with the other proteins in the TGF-β pathway described above are excellent targets for therapeutic intervention.

11.3.5. Effect of Expression on TGF-B Signalling

The effect of both rchd534 and fchd540 on the TGF-β signalling pathway was tested in vitro. Primary BAECs were transfected with a construct called p3TP-Lux, containing a TGF-β responsive promoter fused to a reporter gene (Wrana et al., 1994, Nature 370: 341–347). The rchd534 gene or the fchd540 gene in pCI expression vectors (Promega) was transfected with and without MADR1 (pCMV5MADR1-Flag, Hoodless et al. 1996 Cell 85: 489–500) or MADR2 (pCMV5MADR2-Flag, Eppert et al. 1996 Cell 86: 543–552). The TGF-β response was induced 20-fold by either MADR1 or MADR2. Co-expression of either rchd534 or fchd540 completely eliminated this induction. Thus, the rchd534 and fchd540 proteins inhibited MADR1- and MADR2-mediated TGF-β signalling in endothelial cells. To confirm the specificity of this inhibitory effect, site specific mutants of both rchd534 or fchd540 were constructed, based on known mutations identified in Drosophila homologues, that would be predicted to disrupt MAD-like signaling functions (Sekelsky et al., 1995, Genetics 139:1347–58; Raftery, 1995, Genetics 139:241–54; Newfeld et al., 1996, Development 122:2099–108; Wiersdorff et al., 1996, Development 122:2153–62). Unlike wild type rchd534 and fchd540, these mutant proteins were unable to inhibit the activation of the p3TP promoter in response to TGF-β. The expression levels of the mutant and wild-type proteins were comparable indicating the loss of function was not due to secondary instability.

Interestingly, Smad3, the *C. elegans* homolog to MAD3 which also functions in TGFβ signalling is over 90% identical to Smad2, the *C. elegans* MAD2 homolog, in the MH2 domain. Although this has not yet been directly investigated, it is likely that Smad7, the *C. elegans* homolog of the fchd540 gene, may function similarly to its inhibition to prevent association and activation of Smad3 by the TGFβ receptor, that is, to inhibit the phosphorylation of Smad3 and its association with protein components of the TGF-β signalling pathway.

These results further demonstrate that the interactions of either the rchd534 protein or the fchd540 protein with MADR2 or with activated TβR1 are excellent targets for therapeutic intervention. As described above, the expression of rchd534 and fchd540 is specific, within arterial tissue, to endothelial cells. Accordingly, the rchd534 and rchd540 genes may be targets for intervention in a variety of inflammatory and fibroproliferative disorders that involve endothelial cells, including, but not limited to, cancer angiogenesis, inflammation, and fibrosis.

12. EXAMPLE

Antisense and Ribozyme Molecules for Inhibition of RCHD534 and FCHD540 Expression The principles presented in Section 5.6.1.1, above, can be used to design oligonucleotides for use in inhibiting the expression of target genes, such as the rchd534 or fchd540 genes.

The following antisense molecules can be used to inhibit the expression of the rchd534 gene:

Antisense:
- a) 5'-CATTTCATTTCATACAA-3' which is complementary to nucleotides −14 to +3 of rchd534 in FIG. 6A.
- b) 5'-CATTTCATTTCATACAATATATG-3' which is complementary to nucleotides −20 to +3 of rchd534 in FIG. 6A.
- c) 5'-CATTTCATTTCATACAATATATGGCCTTT-3' which is complementary to nucleotides −26 to +3 of rchd534 in FIG. 6A.

d) 5'-CATTTCATTTCATACAATATATGGCCTTTTGTG GC-3' which is complementary to nucleotides −32 to +3 of rchd534 in FIG. 6A.

e) 5'-GGACATTTCATTTCATACAATATATGGCCTTTT GT-3' which is complementary to nucleotides −29 to +6 of rchd534 in FIG. 6A.

f) 5'-TTCATTTCATACAATATATGGCCTTTTGT-3' which is complementary to nucleotides −29 to −1 of rchd534 in FIG. 6A.

g) 5'-TCATACAATATATGGCCTTTTGT-3' which is complementary to nucleotides −29 to −7 of rchd534 in FIG. 6A.

h) 5'-AATATATGGCCTTTTGT-3' which is complementary to nucleotides −29 to −13 of rchd534 in FIG. 6A.

The following antisense molecules can be used to inhibit the expression of the fchd540 gene:

a) 5'-CATGCGGGGCGAGGAGG-3' which is complementary to nucleotides −14 to +3 of fchd540 in FIG. 2A.

b) 5'-CATGCGGGGCGAGGAGGCGAGGA-3' which is complementary to nucleotides −20 to +3 of fchd540 in FIG. 2A.

c) 5'-CATGCGGGGCGAGGAGGCGAGGAGAAAAG-3' which is complementary to nucleotides −26 to +3 of fchd540 in FIG. 2A.

d) 5'-CATGCGGGGCGAGGAGGCGAGGAGAAAAGT CGTTT-3' which is complementary to nucleotides −32 to +3 of fchd540 in FIG. 2A.

e) 5'-GAACATGCGGGGCGAGGAGGCGAGGAGAAA AGTCG-3' which is complementary to nucleotides −29 to +6 of fchd540 in FIG. 2A.

f) 5'-GCGGGGCGAGGAGGCGAGGAGAAAAGTCG-3' which is complementary to nucleotides −29 to −1 of fchd540 in FIG. 2A.

g) 5'-CGAGGAGGCGAGGAGAAAAGTCG-3' which is complementary to nucleotides −29 to −7 of fchd540 in FIG. 2A.

h) 5'-GGCGAGGAGAAAAGTCG-3' which is complementary to nucleotides −29 to −13 of fchd540 in FIG. 2A.

Ribozymes:

The central, catalytic portion of a hammerhead ribozyme molecule consist of the following sequence:

5'-CAAAGCNGNXXXXCNGAGNAGUC-3';

wherein the 5'-proximal CA bases hybridize to a complementary 5'-UG-3' in the target mRNA. The first four underlined bases form a stem by base pairing with the second set of underlined bases, with the intervening bases, shown as X's, forming a non-pairing loop. In order to hybridize to a target mRNA, a hammerhead ribozyme contains additional bases flanking each end of the central segment shown above. The 5' ribozyme flanking segment is complementary to the respective flanking sequences immediately 3' to the target UG; and the 3' flanking segment is complementary to the respective flanking sequence beginning two bases upstream of the target U, and extending 5'-ward (in effect, skipping the first base upstream of the target U). Cleavage occurs between first and second bases upstream of (i.e., 5' to) the U in the target 5'-UG-3' site. The following ribozyme molecules can be used to inhibit the expression of the rchd534 gene:

a) 5'-GGUGGAGCCCCAGGGCAUUACCUCAAAGC NGNXXXXNCNGAGNAGUCGUGGGCAAG-GUGG GCACUCAGGUGGG-3' which will cleave the rchd534 mRNA between nucleotides 716 and 717 in FIG. 6A.

b) 5'-GUGUCUCUAUGGGUUUGCCCAAAGCNGNX XXNCNGAGNAGUCUCUGGACAUUUCAU-UUCA UAC-3' which will cleave the rchd534 mRNA between nucleotides 1040 and 1041 in FIG. 6B.

c) 5'-GGCCCUCUCGCCGUCGGGCUCCUUGCUGAG CAAAGCNGNXXXXNCNGAGNAGUC-GAUGCCG AAGCCGAUCUUGCUGCGCG-3' which will cleave between nucleotides 1421 and 1422 in FIG. 6B.

The following ribozyme molecules can be used to inhibit the expression of the fchd540 gene:

a) 5'-CGUUUGCCUGCUAAGGAGCGAACAAAGCN GNXXXXNCNGAGNAGUCGAUGUUUCUUUGU GAGUCGGGCGCCG-3', which will cleave the fchd540 mRNA between nucleotides −53 and −52 in FIG. 2A.

b) 5'-CGCCGGACGAGCGCAGAUCGUUUGGUCCUG AACAAAGCNGNXXXXNCNGAGNAGUC-CGGGG CGAGGAGGCGAGGAGAAAAGUCG-3', which will cleave the fchd540 mRNA between nucleotides −1 and +1 in FIG. 2A.

c) 5'-GGAGUAAGGAGGGGGGGGAGACUCUAGUU CGCAAAGCNGNXXXXNCNGAGNAGU-CAGUCG GCUAAGGUGAUGGGGGUUGCAGCACACC-3' which will cleave the fchd540 mRNA between nucleotides +602 and +603 in FIG. 2B.

13. EXAMPLE

Generation of Transgenic Knockout RCHD534 Mutant Mice

This example presents the generation and phenotypic characterization of transgenic knockout homozygous rchd534 mutant mice. Such homozygous rchd534 mutant mice display characteristic cardiovascular disease symptoms, including but not limited to, hyperplasia and/or thickening of at least one cardiac valve, cardiac outflow tract development defects, cardiovascular calcification, epicardial and/or endocardial vascular malformations, or defects in the regulation of vascular tone.

13.1. Materials and Methods 13.1.1 Rchd534 Gene Targeting

Murine rchd534 gene sequences were isolated from a 129/SvJ genomic phage library (Stratagene). An approximately 2.8 kb Xba I fragment containing the rchd534 MH2-encoding exon was subcloned, digested with Mlu I, and linkers were inserted to generate a Xho I restriction site approximately 75 bp downstream of the exon splice acceptor site. Into this Xho I site was subcloned a LacZ-PGKneo cassette in the same transcriptional orientation as rchd534. LacZ, containing the SV40 large T antigen nuclear localization signal at its 5' end and the murine protamine-1 first intron and polyA sequence at its 3' end, was derived from the plasmid pnlacF (Mercer, E. H., Hoyle, G. W., Kapur, R. P., Brinster, R. L. & Palmiter, R. D., 1991, *Neuron* 7, 703–16).

PGK-neo was derived from the plasmid pKJ1 (McBurney, M. W., et al., 1991, *Nucleic Acids Res.* 19, 5755–61). The approximately 3.3 kb Xba I-Nco I fragment downstream of the MH2 exon was subcloned 5' of the herpes simplex virus thymidine kinase (HSV-tk) gene, also driven by the PGK-1 promoter, in pBluescript. This plasmid was then linearized with Xba I and the contiguous 5' rchd534 Xba I genomic fragment containing the LacZ-PGKneo cassette was inserted. The targeting vector was linearized with Not I prior to electroporation into MPI1-12D ES cells derived from 129/SvEvfBRTac mice. G418 and FIAU resistant cells were screened for homologous recombinants by Southern blot (FIGS. 7a and b) using the flanking probe indicated in FIG. 7a. Eighteen targeted clones were detected out of 323 screened.

13.1.2 Generation of Transgenic Knockout Rchd534 Mutant Mice

Targeted ES clones were injected into BALB/cByJ blastocysts as described (Bradley, A. *Teratocarcinomas and Embryonic Stem Cells: A Practical Approach* 1-113-51 (IRL, Oxford, 1987)] to generate chimeras. Male chimeras were bred with BALB/cByJ and females and offspring heterozygous for the mutation were interbred to generate F2 progeny for analysis. Mice on the C57B1/6J were generated similarly. Mice were maintained on a 12h light/12h dark cycle, fed PMI 5021 chow containing 9% fat and provided with water ad libitum.

13.1.3 Northern Analysis

Figure 7D:
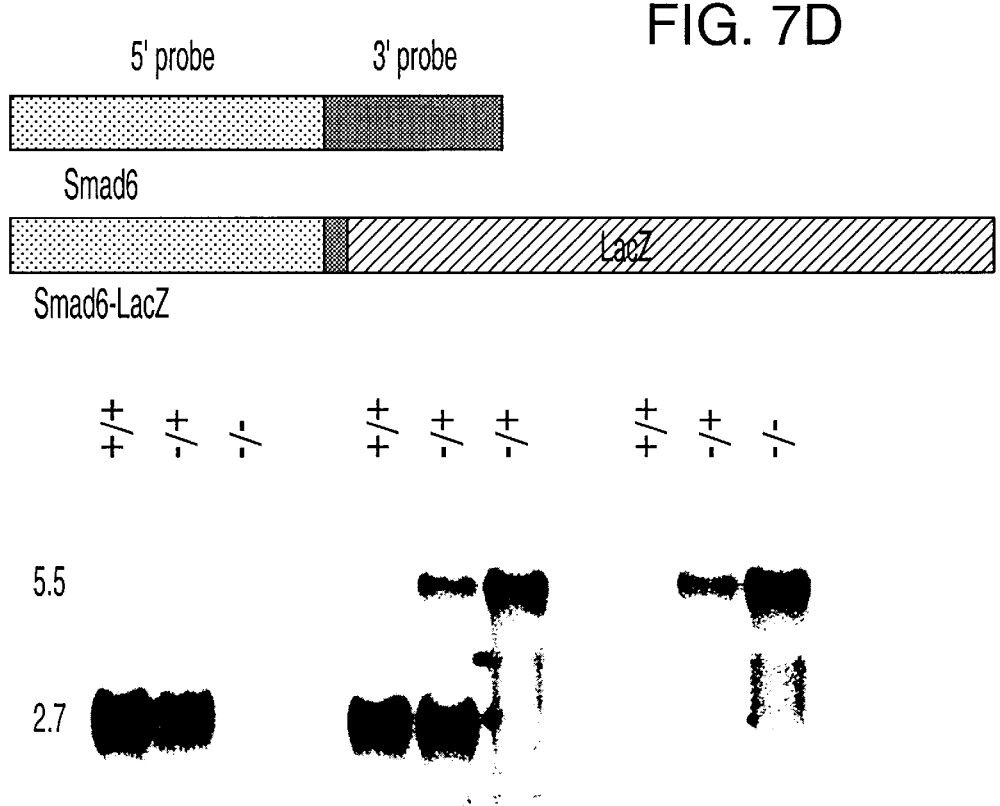

Thirty micrograms of total RNA prepared from lungs using Ultraspec reagent (Biotecx, Houston) was electrophoresed through 1% agarose in formalehyde/MOPS buffer, blotted to Hybond N+ and hybridized using the probes indicated (FIG. 7d).

13.1.4 LacZ Staining

LacZ staining was performed as described (Bonnerot, C. & Nicolas, J.-F. in *Methods in Enzymology* (eds. Wassarman, P. M. & DePamphilis, M. L.) 451–472 (Academic Press, San Diego, 1993)). Crytostat sections were counter-stained with eosin.

13.1.5. Histology

Tissues were fixed with buffered formalin, paraffin-embedded, sectioned at 4 um, and stained with hematoxylin and eosin.

13.1.6 Vascular Contractility Study

Aortic rings prepared from 4–6 month old male mixed 129/SvEv-BALB/cBy mice were analysed as previously described (Lalli, J., Harrer, J. M., Luo, W., Kranias, E. G. & Paul, R. J., 1997, *Circ. Res.* 80, 506–13 (1997)).

13.1.7 Blood Pressure Measurement

Data reported in the text are mean +/− SEM for 10 mutant and 11 wild-type 4–7 month old male mixed 129/SvEv-BALB/cBy mice. Under anesthesia, the right femoral artery was cannulated with a catheter connected to a COBE CDXIII fixed-dome pressure transducer (COBE Cardiovascular, Arvada, Colo.), and pressure and heart rate were monitored using a MacLab data acquisition system (ADInstruments, Boston Mass.).

13.2 Results

13.2.1 Generation of Transgenic Knockout Rchd534 Mutant Mice

Rchd534 mutant mice were created by targeted insertion of a nuclear-localized LacZ/neomycin resistance cassette into the 5' terminus of the exon encoding the c-terminal MH2 domain of rchd534, as diagramed in FIG. 7a. The MH2 region appears to be the major effector domain of Smad proteins including rchd534 (Hata, A., Lagna, G., Massague, J. & Hemmati-Brivanlou, A., 1998, *Genes Dev.* 12, 186–197); acomparable mutation of the Smad2 MH2 domain produced a null allele (Nomura, M. & Li, E., 1998, *Nature* 393, 786–90). Two targeted ES clones (338 and 343, FIG. 7b) were used to generate independent lines of rchd534 mutant mice (FIG. 7c) that were phenotypically indistinguishable. Northern blot analysis of tissues from these mice confirmed the absence of wild-type rchd534 transcripts and the appearance of the predicted rchd534-LacZ fusion transcript, lacking the MH2-encoding domain, as a result of the targeting event (FIG. 7d).

13.2.2 LacZ Staining of Rchd534 Mutant Mice rchd534 expression is transcriptionally regulated in tissue culture cells by addition of TGF-β superfamily ligands (Afrakhte, M., et al., 1998, *Biochem. Biophys. Res. Commun.* 249,505–11; Takase, M., et al., 1998, *Biochem. Biophys. Res. Commun.* 244, 26–9) and by laminar shear stress (Topper, J. N., et al., 1997, Proc. Natl. Acad. Sci. 94, 9314–9). To examine the in vivo expression pattern, staining for LacZ activity was carried out in homozygous rchd534 mutant mice. In embryos studied at e9.5 to e13.5, LacZ activity was predominantly observed in the outflow tract and atrioventricular cushion regions of the heart. At later embryonic stages, the LacZ staining pattern broadened. Expression in the atrioventricular canal areas and outflow tract, including the aorta, its branches, and the pulmonary trunk, remained strong. In many tissues, including the lungs, staining was observed specifically in vascular endothelium of larger vessels, but strong non-vascular staining was also observed in the gastrointestinal system and developing bones.

After birth, LacZ expression was largely restricted to the vascular endothelium. Staining of the outflow tract and heart valves remained intense through adulthood, but expression in the aorta was non-uniform. Staining was strongest in the wall of the aortic root, where several layers of cells, including endothelial and vascular smooth muscle cells, were LacZ positive. More distally, expression was specifically endothelial and stronger around branchpoints. Elsewhere, vessel endothelium exhibited an organ-specific staining pattern in adults. For example, in the lungs, all vessels were LacZ positive, while in the brain, staining was confined the larger arteries. The endothelium of coronary arteries and myocardial vessels was variably LacZ positive. Outside of the heart, the only non-endothelial staining observed in adults was in sperm at later stages of differentiation.

The LacZ staining pattern of homozygous mutant mice was generally similar to results of in situ hybridization to rchd534 mRNA in wild-type animals, suggesting that it reflects the regulation of the endogenous gene. A notable exception was observed in epicardial and endocardial cells of the right atrium, where expression appeared to be upregulated in the homozygous mutants, beginning around one day after birth and persisting through adulthood. The mechanism underlying this localized upregulation has not been determined.

13.2.3 Genotyping of Progeny

Genotyping of progeny of heterozygous intercrosses at the time of weaning revealed that on an inbred or mixed (129/Sv×BALB/cBy or 129/Sv×C57BL/6) background, homozygous mutant pups were present at less than the expected Mendelian ratio (Table 4). The diminished number of homozygous mutants largely resulted from perinatal loss of these pups, but the possibility of some embryonic lethality has not been eliminated. Spontaneous deaths after 2 weeks of age were very rare. Both male and female homozygous mutants were fertile.

TABLE 4

Under-representation of homozygous rchd534 mutants

| Strain | Progeny homozygous mutant | heterozygous | wild-type | total |
|---|---|---|---|---|
| 129/SvEv x BALB/cBy | 37 (9%) | 246 (59%) | 135 (32%) | 418 |
| 129/SvEv x C57B1/6 | 16 (13%) | 75 (60%) | 34 (27%) | 125 |
| 129/SvEv inbred | 2 (2%) | 47 (54%) | 38 (44%) | 87 |

Total progeny (F2–F4 generations) that survived to weaning from several heterozygous intercrosses are listed.

13.2.4 Phenotypic Characterization of RCHD534Mutant Mice

The prevalent phenotypic consequence of the rchd534 mutation was a group of cardiovascular defects, correlating closely with the observed rchd534 expression patterns. Every homozygous mutant animal examined from the time of birth showed hyperplastic thickening of at least one cardiac valve, and in some cases all four valves were affected. Dead or distressed neonates typically had more severely enlarged valves than healthy adult mutants, with abundant mesenchymal cells populating the extracellular matrix-rich interior of the valves. These mesenchymal cells as well as the endocardial cells covering the valve surfaces expressed rchd534. Every homozygous mutant mouse examined at or beyond 6 weeks of age also showed ossification around the outflow tract of the heart, which was never observed in wild-type mice. Bone formation most commonly occurred in the aortic media just distal to the valve. Ossification was not seen in newborns, and appeared to reflect a process of cartilaginous metaplasia and endochondral bone formation. In one animal, two areas of ossification, one proximal and one distal to the aortic valve, contained bone trabeculae with marrow elements.

There were a number of additional incompletely penetrant cardiovascular phenotypes. Severe outflow tract defects, which appeared to result from abnormal positioning of the aorticopulmnonary septum, were observed in some late stage embryos and dead newborns. Subepicardial vascular malformations were also present in some of the dead/moribund newborn mutant mice. These bundles of dilated and congested vessels consisted of large, blood filled lumens lined with LacZ-expressing endothelial cells, and lacked the multiple smooth muscle cell layers typical of large vessels. Some surviving mutant mice exhibited localized proliferation and thickening of the endocardium, possibly in response to flow disturbances resulting from the valve defects. Lastly, in some homozygous mutant mice there was evidence of focal ischemic changes in the lungs, liver and kidneys, and occasional thrombosis, likely resulting from compromised heart function.

13.2.5 The Role of RCHD534 in Vascular Physiology

To examine the role of rchd534 in vascular physiology, aortic contractility was analysed using an ex vivo approach. Intact and de-endothelialized rings from the descending aorta of wild-type and homozygous mutant mice were challenged with increasing doses of phenylephrine (PE), an agonist for a-adrenergic receptors on vascular smooth muscle (FIG. 8). Wild-type intact rings were significantly less responsive than wild type de-endothelialized rings, an expected difference thought to reflect the activity of an endogenous endothelial relaxing factor (Cohen, R. A., Zitnay, K. M., Weisbrod, R. M. & Tesfamariam, B., 1988, J. Pharmacol. Exp. Ther. 244, 550–5). De-endothelialized rings from rchd534 mutant and wild-type mice were indistinguishable in their response to PE. However, intact rings from rchd534 homozygous mutants contracted significantly more than those from wild-type mice and showed no evidence of an endothelial relaxing activity. In fact, the rchd534 mutant rings showed a trend toward increased contraction with the endothelium present. These results indicate a defect in endothelial modulation of vascular contractility in the mutants, potentially reflecting an imbalance of endothelial constriction factors (such as endothelin-1), and endothelial relaxing factors (such as nitric oxide). Consistent with these ex vivo results, the mean arterial pressure measured in the femoral artery was significantly increased in rchd534 mutant mice (93+/–6 mmHg vs. 77+/–4 mmHg for wild type). Taken together with the endothelial expression pattern, these data support an important role for rchd534 in the endothelial modulation of vascular tone.

13.2.6 The Interrelationship Between the Phenotypic Consequences of the Rchd534 Mutant Mice and TGF-β Superfamily Signaling The developmental and physiological phenotypes of the rchd534 mutant mice demonstrate the key role rchd534 plays in the function of TGF-β superfamily signaling in the cardiovascular system. While in vitro and in vivo evidence implicates TGF-β signaling in the regulation of vasculartone (Perrella, M. A., Jain, M. K. & Lee, M.-E., 1998, Miner Electrolyte Metab 24, 136–143; Li, B., Khanna, A., Sharma, V. S., T. & Suthanthiran, M. A., P., 1998, Hypertension 33, 271–5), ossification of the vascular media (Schulick, A. H., et al., 1998, Proc. Natl. Acad. Sci. 95, 6983–8; Watson, K. E., et al., 1994, J. Clin. Invest. 93, 2106–13); vascular malformations (Marchuk, D. A., 1998, Curr Opin Hematol 5, 332–8); cardiac outflow tract development (Sanford, L. P., et al., 1997, Development 124, 2659–2670), the data presented here is the first evidence that rchd534 plays a key role in these functions. In addition, organ culture studies have implicated TGF-β superfamily signaling in cardiac valve formation (Boyer, A. S., Erickson, C. P. & Runyan, R. B., 1999, Dev. Dyn. 214, 81–91); Brown, C. B., Boyer, A. S., Runyan, R. B. & Barnett, J. V., 1996, Dev Biol 174,248–57; Moore, C. S., Mjaatvedt, C. H. & Gearhart, J. D., 1998, Dev. Dyn. 212, 548–562; Nakajima, Y., Yamagishi, T., Nakamura, H., Markwald, R. R. & Krag, E. L., 1998, Dev. Bio. 194,99–113; Ramsdell, A. F. & Markwald, R. R., 1997, Dev. Biol. 188, 64–74) specifically in induction of the process of endocardial migration and transformation that produces specialized mesenchymal cells to populate the interior of the endocardial cushions (Eisenberg, L. M. & Markwald, R. R., 1995, Circ. Res. 77, 1–6; Huang, J.-X., Potts, J. D., Vincent, E. B., Weeks, D. L. & Runyan, R. B., 1995, Ann. N.Y. Acad. Sci. 752, 317–30). However, targeted mutations of TGF-β superfamily ligands and receptors have not demonstrated perturbations of this process (Kaartinen, V., et al., 1995, Nat. Genet. 11, 415–21; Matzuk, M. M., et al., 1995, Nature 374, 354–6; Oshirna, M., Oshima, H. & Taketo, M. M., 1996, Dev. Biol. 179,297–302; Proetzel, G., et al., 1995, Nat. Genet. 11,409–14). The rchd534 mutant mice described herein provide the first genetic evidence for the role of TGF-β superfamily signaling in cardiac valve development, and should provide an important model for further studies in this field. These studies further confirm the important role for the rchd534 protein in the development and homeostasis of the cardiovascular system, reflecting a key role for rchd534 in the tissue-specific modulation of TGF-β signaling pathways.

14. EXAMPLE

The RCHD534-Long Protein

As described below, the rchd534 gene was discovered to encode two spliceoforms. The short spliceoform, and the rchd534 protein it encodes, are described in detail in Section 11, above. A second novel spliceoform, encoding a novel longer protein designated rchd534-long, is described in detail in the subsection below.

14.1 Identification and Characterization of the RCHD534-Long Spliceoform and Protein A human heart cDNA library (Stratagene, LaJolla, Calif.) was screened with a probe containing nucleotides 400–700 of the fchd540 (see FIG. 2B) under the following hybridization conditions: hybridization overnight at 65° C., washing with 2×SSC and 0.1% SDS for 20 minutes at room temperature, followed two washes with 0.2×SSC and 0.1% SDS for 20 minutes at 65° C. A positive clone was found to encode a novel protein, related to the rchd534 protein, that was designated the rchd534-long protein. The rchd534-long protein, like the rchd534 protein, has an MH2 domain. In addition, the rchd534-long protein has an MH1 domain not present in rchd534. The original clone isolated from the Stratagene heart library contained incorrect sequence, including two stop codons, between the MH1 and MH2 domain coding regions. Therefore, cDNA prepared from human heart mRNA (Clontech, Palo Alto, Calif.) was used as template for the PCR reaction to isolate the correct cDNA sequence in the region spanning the MH1 and MH2 domain coding regions. The following two pairs of nested primers were used:

Pair 1: A) 5'-GAGGCTGCGGCCGCTCCGAAGTCC-3'
B) 5'-CTCCGCCGGGGCCGCCACTATCT-3'
Pair 2: A) 5'-CCGGGACGCAGTGGGACAG-3'
B) 5'-CGGGGAGTTGACGAAGATGG-3'

The nucleotide sequence of the PCR amplification product was determined and confirmed to be accurate by sequence analysis of several amplification products from both Clontech human lung cDNA, and heart mRNA that was obtained from Clontech and then reverse-transcribed into cDNA. The incorrect sequence in the original clone obtained from the Stratagene heart library was replaced by a PCR amplification product containing the correct sequence.

This correct cDNA encoding the rchd534-long protein was cloned into the TA cloning vector (Invitrogen) to create plasmid pHL6TA1A, which was deposited with the American Type Culture Collection on Feb. 6, 1998 as Accession No. 209615. The cDNA sequence of the rchd534-long spliceoform encoding the entire rchd534-long protein is shown in FIGS. 10A–10B. The rchd534-long nucleotide sequence is 93% identical to the nucleotide sequence of the mouse SMAD6 gene (Imamura et al., 1997, Nature 389: 622–626). The rchd534-long sequence was reported in Hata et al., 1998, Genes and Development 12: 186–197.

The domains of the rchd534-long protein are shown in schematic form and compared with the domains of the rchd534 protein in FIG. 11. The rchd534-long protein contains an MH1 domain, a spacer region, and an MH2 domain. The rchd534-long protein contains an N-terminal 273 amino acids (from Met-1 to Glu-273) which are not present in the rchd534 protein. This N-terninal region contains an MH1 domain that is more highly homologous to the MH1 domain of fchd540 than to the MH1 domain of other MAD proteins.

The amino acid sequence of rchd534-long protein from amino acid Ser-274 to the C-terminal amino acid Arg-496 are identical to amino acids Ser-13 to the C-terminal amino acid Arg-235 of the rchd534 protein. This region comprises an MH2 domain, from Pro-328 to Arg-496 in rchd534-long, and from Pro-67 to Arg-235 in rchd534. The rchd534 protein contains a 12 amino acid sequence at the N-terminus, from Met-1 to Lys-12, which is not present in the rchd534-long protein.

14.2. TGF-β Signalling Inhibitory Activity of the RCHD534-Long Protein

The activity of the rchd534-long protein was tested using the TGF-β responsive reporter system described in Section 15.3.5, above for the rchd534 and fchd540 proteins.

HEPG2, 293 and BAEC cells were transfected with a construct called p3TP-Lux, containing a TGF-β responsive promoter fused to a reporter gene (Wrana et al., 1994, Nature 370: 341–347). The rchd534-long gene in pCI expression vectors (Promega) was transfected with and without MADR2. Luciferase activity produced from the reporter construct was measured relative to an internal control (secreted alkaline phosphatase expression). The results obtained in 293 (human embryonic kidney) cells are summarized in Table 5 below. A "+" indicates that the specified construct, plasmid, or gene was present in the cell line assayed; whereas a "–" indicates that it was absent.

TABLE 5

| 3TP-LUX | TGF-bRI | pCI | MADR2 | fchd540 | rchd534 | rchd534-long | Relative Luciferase Activity |
|---|---|---|---|---|---|---|---|
| + | – | – | – | – | – | – | 10 |
| + | + | – | – | – | – | – | 48 |
| + | + | + | – | – | – | – | 40 |
| + | + | – | + | – | – | – | 107 |
| + | + | – | – | + | – | – | 2 |
| + | + | – | – | – | + | – | 10 |
| + | + | – | – | – | – | + | 2 |
| + | + | + | + | – | – | – | 104 |
| + | + | – | + | – | – | – | 124 |
| + | + | – | + | + | – | – | 13 |
| + | + | – | + | – | + | – | 59 |
| + | + | – | + | – | – | + | 18 |

The TGF-β response, both un-induced by MADR2 and induced by MADR2 overexpression, was inhibited by expression of rchd534-long, as well as by rchd534 and fchd540. Similar inhibition of TGF-β signalling by the rchd534-long protein was observed in each of the several different cell lines.

15. Deposit of Microorganisms

The following microorganisms were deposited with the American Type Culture Collection (ATCC), Rockville, Md., on the indicated dates and assigned the indicated accession numbers:

| Microorganism | ATCC Accession No. | Date of Deposit |
|---|---|---|
| pFCHD531 | 69983 | February 7, 1996 |
| PFCHD540 | 69984 | February 7, 1996 |
| fchd545 | 69974 | January 5, 1996 |
| PHL6TA1A | 209615 | February 6, 1998 |

The following microorganism was deposited with the Agricultural Research Service Culture Collection (NRRL), Peoria, Ill., on the indicated date and assigned the indicated accession number:

| Microorganism | NRRL Accession No. | Date of Deposit |
|---|---|---|
| FCHD534 | B-21459 | June 6, 1995 |

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

What is claimed is:

1. A homozygous transgenic mouse whose germ cells comprise a mutated rchd534-LacZ gene which lacks the MH2 domain encoding region, wherein the endogenous wild-type rchd534 gene of said mouse has been replaced with said mutated rchd534-LacZ gene which lacks the MH2 domain encoding region, and wherein said mouse displays a cardiovascular disease symptom.

2. The transgenic mouse of claim 1, wherein said cardiovascular disease symptom is hyperplasia, thickening of at least one cardiac valve, cardiac outflow tract development defects, cardiovascular calcification, epicardial vascular malformations, endocardial vascular malformation, or defects in the regulation of vascular tone.

3. The transgenic mouse of claim 1, wherein said cardiovascular disease symptom is cardiovascular calcification .

4. The transgenic mouse of claim 1, wherein said cardiovascular. disease symptom is aortic or valvular calcification.

5. A method of producing a homozygous transgenic mouse, whose germ cells comprise a mutated rchd534-LacZ gene which lacks the MH2 domain encoding region, wherein the endogenous wild-type rchd534 gene of said mouse has been replaced with said mutated rchd534-LacZ gene which lacks the MH2 domain encoding region, comprising: (a) introducing by homologous recombination with the endogenous wild-type rchd534 gene a polynucleotide encoding said mutated rchd534-LacZ gene which lacks the MH2 domain encoding region into a mouse embryonic stem cell; (b) introducing said embryonic stem cell into a mouse blastocyst to create a transgenic embryo; and (c) allowing said embryo to develop into said transgenic mouse, wherein said transgenic mouse displays a cardiovascular disease symptom.

6. The method of claim 5, wherein said cardiovascular disease symptom is hyperplasia, thickening of at least one cardiac valve, cardiac outflow tract development defects, cardiovascular calcification, epicardial vascular malformations, endocardial vascular malformation, or defects in the regulation of vascular tone.

7. The method of claim 5, wherein said cardiovascular disease symptom is cardiovascular calcification.

8. A method for identifying a substance potentially useful for treating or preventing cardiovascular disease, comprising administering said substance to a homozygous transgenic mouse whose germ cells comprise a mutated rchd534-LacZ gene which lacks the MH2 domain encoding region, wherein the endogenous wild-type rchd534 gene of said mouse has been replaced with said mutated rchd534-LacZ gene which lacks the MH2 domain encoding region, and wherein said transgenic mouse displays a cardiovascular disease symptom, and wherein amelioration of said cardiovascular disease symptom indicates a substance potentially effective in the treatment or prevention of cardiovascular disease.

9. The method of claim 8, wherein said cardiovascular disease symptom is hyperplasia, thickening of at least one cardiac valve, cardiac outflow tract development defects, cardiovascular calcification, epicardial vascular malformations, endocardial vascular malformation, or defects in the regulation of vascular tone.

10. The method of claim 8, wherein said cardiovascular disease symptom is cardiovascular calcification.

11. An isolated mouse cell comprising a mutated rchd534-LacZ gene which lacks the MH2 domain encoding region, wherein the endogenous wild-type rchd534 gene has been replaced with said mutated rchd534-LacZ gene which lacks the MH2 domain encoding region.

* * * * *

SEQUENCE LISTING

```
<160> NUMBER OF SEQ ID NOS: 46

<210> SEQ ID NO 1
<211> LENGTH: 1953
<212> TYPE: DNA
<213> ORGANISM: Homo sapiens
<220> FEATURE:
<221> NAME/KEY: CDS
<222> LOCATION: (162)...(1871)

<400> SEQUENCE: 1
ggcacgagtc ggagccgggc ggaggggagg ggggaaagag gagcgcaggg tgagagtgag      60
ccgcaggctt cgggaggcga ggggcgggg ggagcagcgc cgaggycgcc gcctccgcct     120
ccgccgccta ggactagggg gtggggacg gacaagcccc g atg ccg ggg gag acg     176
                                            Met Pro Gly Glu Thr
                                              1               5 gaa gag ccg aga ccc ccg gag cag cag gac cag gaa ggg gga gag gcg     224
Glu Glu Pro Arg Pro Pro Glu Gln Gln Asp Gln Glu Gly Gly Glu Ala
               10                  15                  20 gcc aag gcg gct ccg gag gag ccc caa caa cgg ccc cct gag gcg gtc     272
Ala Lys Ala Ala Pro Glu Glu Pro Gln Gln Arg Pro Pro Glu Ala Val
           25                  30                  35 gcg gcg gcg cct gca ggg acc act agc agc cgc gtg ctg agg gga ggt     320
Ala Ala Ala Pro Ala Gly Thr Thr Ser Ser Arg Val Leu Arg Gly Gly
       40                  45                  50 cgg gac cga ggc cgg gcc gct gcg gcc gcc gcc gca gct gtg tcc         368
Arg Asp Arg Gly Arg Ala Ala Ala Ala Ala Ala Ala Ala Val Ser
   55                  60                  65 cgc cgg agg aag gcc gag tat ccc cgc cgg cgg agg agc agc ccc agc     416
Arg Arg Arg Lys Ala Glu Tyr Pro Arg Arg Arg Ser Ser Pro Ser
70                  75                  80                  85 gcc agg cct ccc gac gtc ccc ggg cag cag ccc cag gcc gcg aag tcc     464
Ala Arg Pro Pro Asp Val Pro Gly Gln Gln Pro Gln Ala Ala Lys Ser
               90                  95                 100 ccg tct cca gtt cag ggc aag aag agt ccg cga ctc cta tgc ata gaa     512
Pro Ser Pro Val Gln Gly Lys Lys Ser Pro Arg Leu Leu Cys Ile Glu
           105                 110                 115 aaa gta aca act gat aaa gat ccc aag gaa gaa aaa gag gaa gaa gac     560
Lys Val Thr Thr Asp Lys Asp Pro Lys Glu Glu Lys Glu Glu Glu Asp
       120                 125                 130 gat tct gcc ctc cct cag gaa gtt tcc att gct gca tct aga cct agc     608
Asp Ser Ala Leu Pro Gln Glu Val Ser Ile Ala Ala Ser Arg Pro Ser
   135                 140                 145
```

-continued

```
cgg ggc tgg cgt agt agt agg aca tct gtt tct cgc cat cgt gat aca    656
Arg Gly Trp Arg Ser Ser Arg Thr Ser Val Ser Arg His Arg Asp Thr
150             155                 160                 165 gag aac acc cga agc tct cgg tcc aag acc ggt tca ttg cag ctc att    704
Glu Asn Thr Arg Ser Ser Arg Ser Lys Thr Gly Ser Leu Gln Leu Ile
                170                 175                 180 tgc aag tca gaa cca aat aca gac caa ctt gat tat gat gtt gga gaa    752
Cys Lys Ser Glu Pro Asn Thr Asp Gln Leu Asp Tyr Asp Val Gly Glu
            185                 190                 195 gag cat cag tct cca ggt ggc att agt ggt gaa gag gaa gag gag        800
Glu His Gln Ser Pro Gly Gly Ile Ser Gly Glu Glu Glu Glu Glu
        200                 205                 210 gaa gaa gag atg tta atc agt gaa gag gag ata cca ttc aaa gat gat    848
Glu Glu Glu Met Leu Ile Ser Glu Glu Glu Ile Pro Phe Lys Asp Asp
    215                 220                 225 cca aga gat gag acc tac aaa ccc cac tta gaa agg gaa acc cca aag    896
Pro Arg Asp Glu Thr Tyr Lys Pro His Leu Glu Arg Glu Thr Pro Lys
230             235                 240                 245 cca cgg aga aaa tca ggg aag gta aaa gaa gag aag gag aag aag gaa    944
Pro Arg Arg Lys Ser Gly Lys Val Lys Glu Glu Lys Glu Lys Lys Glu
                250                 255                 260 att aaa gtg gaa gta gag gtg gag gtg aaa gaa gag gag aat gaa att    992
Ile Lys Val Glu Val Glu Val Glu Val Lys Glu Glu Glu Asn Glu Ile
            265                 270                 275 aga gag gat gag gaa cct cca agg aag aga gga aga aga cga aaa gat   1040
Arg Glu Asp Glu Glu Pro Pro Arg Lys Arg Gly Arg Arg Lys Asp
        280                 285                 290 gac aaa agt cca cgt tta ccc aaa agg aga aaa aag cct cca atc cag   1088
Asp Lys Ser Pro Arg Leu Pro Lys Arg Arg Lys Lys Pro Pro Ile Gln
    295                 300                 305 tat gtc cgt tgt gag atg gaa gga tgt gga act gtc ctt gcc cat cct   1136
Tyr Val Arg Cys Glu Met Glu Gly Cys Gly Thr Val Leu Ala His Pro
310             315                 320                 325 cgc tat ttg cag cac cac att aaa tac cag cat ttg ctg aag aag aaa   1184
Arg Tyr Leu Gln His His Ile Lys Tyr Gln His Leu Leu Lys Lys Lys
                330                 335                 340 tat gta tgt ccc cat ccc tcc tgt gga cga ctc ttc agg ctt cag aag   1232
Tyr Val Cys Pro His Pro Ser Cys Gly Arg Leu Phe Arg Leu Gln Lys
            345                 350                 355 caa ctt ctg cga cat gcc aaa cat cat aca gat caa agg gat tat atc   1280
Gln Leu Leu Arg His Ala Lys His His Thr Asp Gln Arg Asp Tyr Ile
        360                 365                 370 tgt gaa tat tgt gct cgg gcc ttc aag agt tcc cac aat ctg gca gtg   1328
Cys Glu Tyr Cys Ala Arg Ala Phe Lys Ser Ser His Asn Leu Ala Val
    375                 380                 385 cac cgg atg att cac act ggc gag aag cca tta caa tgt gag atc tgt   1376
His Arg Met Ile His Thr Gly Glu Lys Pro Leu Gln Cys Glu Ile Cys
390             395                 400                 405 gga ttt act tgt cga caa aag gca tct ctt aat tgg cac atg aag aaa   1424
Gly Phe Thr Cys Arg Gln Lys Ala Ser Leu Asn Trp His Met Lys Lys
                410                 415                 420 cat gat gca gac tcc ttc tac cag ttt tct tgc aat atc tgt ggc aaa   1472
His Asp Ala Asp Ser Phe Tyr Gln Phe Ser Cys Asn Ile Cys Gly Lys
            425                 430                 435 aaa ttt gag aag aag gac agc gta gtg gca cac aag gca aaa agc cac   1520
Lys Phe Glu Lys Lys Asp Ser Val Val Ala His Lys Ala Lys Ser His
        440                 445                 450 cct gag gtg ctg att gca gaa gct ctg gct gcc aat gca ggc gcc ctc   1568
Pro Glu Val Leu Ile Ala Glu Ala Leu Ala Ala Asn Ala Gly Ala Leu
```

-continued

```
                455                 460                 465
atc acc agc aca gat atc ttg ggc act aac cca gag tcc ctg acg cag        1616
Ile Thr Ser Thr Asp Ile Leu Gly Thr Asn Pro Glu Ser Leu Thr Gln
470                 475                 480                 485 cct tca gat ggt cag ggt ctt cct ctt ctt cct gag ccc ttg gga aac        1664
Pro Ser Asp Gly Gln Gly Leu Pro Leu Leu Pro Glu Pro Leu Gly Asn
            490                 495                 500 tca acc tct gga gag tgc cta ctg tta gaa gct gaa ggg atg tca aag        1712
Ser Thr Ser Gly Glu Cys Leu Leu Leu Glu Ala Glu Gly Met Ser Lys
        505                 510                 515 tca tac tgc agt ggg acg gaa cgg gtg agc ctg atg gct gat ggg aag        1760
Ser Tyr Cys Ser Gly Thr Glu Arg Val Ser Leu Met Ala Asp Gly Lys
    520                 525                 530 atc ttt gtg gga agc ggc agc agt gga ggc act gaa ggg ctg gtt atg        1808
Ile Phe Val Gly Ser Gly Ser Ser Gly Gly Thr Glu Gly Leu Val Met
535                 540                 545 aac tca gat ata ctc ggt gct acc aca gag gtt ctg att gaa gat tca        1856
Asn Ser Asp Ile Leu Gly Ala Thr Thr Glu Val Leu Ile Glu Asp Ser
550                 555                 560                 565 gac tct gcc gga cct tagtggacag gaagacttgg ggcatgggac agctcagact        1911
Asp Ser Ala Gly Pro
                570 ttgtatttaa aagttaaaaa ggacaaaaaa aaaaaaaaaa aa                         1953

<210> SEQ ID NO 2
<211> LENGTH: 3103
<212> TYPE: DNA
<213> ORGANISM: Homo sapiens
<220> FEATURE:
<221> NAME/KEY: CDS
<222> LOCATION: (288)...(1565)

<400> SEQUENCE: 2
gcacgagcgg agagccgcgc agggcgcggg ccgcgcgggg tggggcagcc ggagcgcagg        60
cccccgatcc ccggcgggcg ccccggggcc ccgcgcgcg ccccggcctc cgggagactg       120
gcgcatgcca cggagcgccc ctcgggccgc cgccgctcct gccgggccc ctgctgctgc        180 tgctgtcgcc tgcgcctgct gccccaactc ggcgcccgac tcacaaagaa acatcatgtt       240
cgctccttag caggcaaacg acttttctcc tcgcctcctc gccccgc atg ttc agg       296
                                                    Met Phe Arg
                                                     1 acc aaa cga tct gcg ctc gtc cgg cgt ctc tgg agg agc cgt gcg ccc       344
Thr Lys Arg Ser Ala Leu Val Arg Arg Leu Trp Arg Ser Arg Ala Pro
    5                  10                  15 ggc ggc gag gac gag gag gag ggc gca ggg gga ggt gga gga gga ggc       392
Gly Gly Glu Asp Glu Glu Glu Gly Ala Gly Gly Gly Gly Gly Gly Gly
20                  25                  30                  35 gag ctg cgg gga gaa ggg gcg acg gac agc cga gcg cat ggg gcc ggt       440
Glu Leu Arg Gly Glu Gly Ala Thr Asp Ser Arg Ala His Gly Ala Gly
            40                  45                  50 ggc ggc ggc ccg ggc agg gct gga tgc tgc ctg ggc aag gcg gtg cga       488
Gly Gly Gly Pro Gly Arg Ala Gly Cys Cys Leu Gly Lys Ala Val Arg
        55                  60                  65 ggt gcc aaa ggt cac cac cat ccc cac ccg cca gcc gcg ggc gcc ggc       536
Gly Ala Lys Gly His His His Pro His Pro Pro Ala Ala Gly Ala Gly
    70                  75                  80 gcg gcc ggg ggc gcc gag gcg gat ctg aag gcg ctc acg cac tcg gtg       584
Ala Ala Gly Gly Ala Glu Ala Asp Leu Lys Ala Leu Thr His Ser Val
85                  90                  95
```

-continued

| | | |
|---|---|---|
| ctc aag aaa ctg aag gag cgg cag ctg gag ctg ctg ctc cag gcc gtg<br>Leu Lys Lys Leu Lys Glu Arg Gln Leu Glu Leu Leu Leu Gln Ala Val<br>100                             105                       110                     115 | 632 |
| gag tcc cgc ggc ggg acg cgc acc gcg tgc ctc ctg ctg ccc ggc cgc<br>Glu Ser Arg Gly Gly Thr Arg Thr Ala Cys Leu Leu Leu Pro Gly Arg<br>                 120                       125                     130 | 680 |
| ctg gac tgc agg ctg ggc ccg ggg gcg ccc gcc ggc gcg cag cct gcg<br>Leu Asp Cys Arg Leu Gly Pro Gly Ala Pro Ala Gly Ala Gln Pro Ala<br>         135                     140                     145 | 728 |
| cag ccg ccc tcg tcc tac tcg ctc ccc ctc ctg tgc aaa gtg ttc<br>Gln Pro Pro Ser Ser Tyr Ser Leu Pro Leu Leu Leu Cys Lys Val Phe<br>             150                     155                     160 | 776 |
| agg tgg ccg gat ctc agg cat tcc tcg gaa gtc aag agg ctg tgt tgc<br>Arg Trp Pro Asp Leu Arg His Ser Ser Glu Val Lys Arg Leu Cys Cys<br>165                             170                       175 | 824 |
| tgt gaa tct tac ggg aag atc aac ccc gag ctg gtg tgc tgc aac ccc<br>Cys Glu Ser Tyr Gly Lys Ile Asn Pro Glu Leu Val Cys Cys Asn Pro<br>180                             185                     190                   195 | 872 |
| cat cac ctt agc cga ctc tgc gaa cta gag tct ccc ccc cct cct tac<br>His His Leu Ser Arg Leu Cys Glu Leu Glu Ser Pro Pro Pro Pro Tyr<br>                 200                       205                     210 | 920 |
| tcc aga tac ccg atg gat ttt ctc aaa cca act gca gac tgt cca gat<br>Ser Arg Tyr Pro Met Asp Phe Leu Lys Pro Thr Ala Asp Cys Pro Asp<br>         215                     220                     225 | 968 |
| gct gtg cct tcc tcc gct gaa aca ggg gga acg aat tat ctg gcc cct<br>Ala Val Pro Ser Ser Ala Glu Thr Gly Gly Thr Asn Tyr Leu Ala Pro<br>230                             235                     240 | 1016 |
| ggg ggg ctt tca gat tcc caa ctt ctt ctg gag cct ggg gat cgg tca<br>Gly Gly Leu Ser Asp Ser Gln Leu Leu Leu Glu Pro Gly Asp Arg Ser<br>         245                     250                     255 | 1064 |
| cac tgg tgc gtg gtg gca tac tgg gag gag aag acg aga gtg ggg agg<br>His Trp Cys Val Val Ala Tyr Trp Glu Glu Lys Thr Arg Val Gly Arg<br>260                             265                     270                   275 | 1112 |
| ctc tac tgt gtc cag gag ccc tct ctg gat atc ttc tat gat cta cct<br>Leu Tyr Cys Val Gln Glu Pro Ser Leu Asp Ile Phe Tyr Asp Leu Pro<br>                 280                       285                     290 | 1160 |
| cag ggg aat ggc ttt tgc ctc gga cag ctc aat tcg gac aac aag agt<br>Gln Gly Asn Gly Phe Cys Leu Gly Gln Leu Asn Ser Asp Asn Lys Ser<br>         295                     300                     305 | 1208 |
| cag ctg gtg cag aag gtg cgg agc aaa atc ggc tgc ggc atc cag ctg<br>Gln Leu Val Gln Lys Val Arg Ser Lys Ile Gly Cys Gly Ile Gln Leu<br>             310                     315                     320 | 1256 |
| acg cgg gag gtg gat ggt gtg tgg gtg tac aac cgc agc agt tac ccc<br>Thr Arg Glu Val Asp Gly Val Trp Val Tyr Asn Arg Ser Ser Tyr Pro<br>325                             330                     335 | 1304 |
| atc ttc atc aag tcc gcc aca ctg gac aac ccg gac tcc agg acg ctg<br>Ile Phe Ile Lys Ser Ala Thr Leu Asp Asn Pro Asp Ser Arg Thr Leu<br>340                             345                     350                   355 | 1352 |
| ttg gta cac aag gtg ttc ccc ggt ttc tcc atc aag gct ttc gac tac<br>Leu Val His Lys Val Phe Pro Gly Phe Ser Ile Lys Ala Phe Asp Tyr<br>                 360                       365                     370 | 1400 |
| gag aag gcg tac agc ctg cag cgg ccc aat gac cac gag ttt atg cag<br>Glu Lys Ala Tyr Ser Leu Gln Arg Pro Asn Asp His Glu Phe Met Gln<br>         375                     380                     385 | 1448 |
| cag ccg tgg acg ggc ttt acc gtg cag atc agc ttt gtg aag ggc tgg<br>Gln Pro Trp Thr Gly Phe Thr Val Gln Ile Ser Phe Val Lys Gly Trp<br>             390                     395                     400 | 1496 |
| ggt cag tgc tac acc cgc cag ttc atc agc agc tgc ccg tgc tgg cta<br>Gly Gln Cys Tyr Thr Arg Gln Phe Ile Ser Ser Cys Pro Cys Trp Leu<br>405                             410                     415 | 1544 |

-continued

```
gag gtc atc ttc aac agc cgg tagccgcgtg cggaggggac agagcgtgag    1595
Glu Val Ile Phe Asn Ser Arg
420                 425 ctgagcaggc cacacttcaa actactttgc tgctaatatt ttcctcctga gtgcttgctt   1655
ttcatgcaaa ctctttggtc gttttttttt tgtttgttgg ttggttttct tcttctcgtc   1715
ctcgtttgtg ttctgttttg tttcgctctt tgagaaatag cttatgaaaa gaattgttgg   1775
gggttttttt ggaagaaggg gcaggtatga tcggcaggac accctgatag gaagagggga   1835
agcagaaatc caagcaccac caaacacagt gtatgaaggg gggcggtcat catttcactt   1895
gtcaggagtg tgtgtgagtg tgagtgtgcg gctgtgtgtg cacgcgtgtg caggagcggc   1955
agatggggag acaacgtgct ctttgttttg tgtctcttat ggatgtcccc agcagagagg   2015
tttgcagtcc caagcggtgt ctctcctgcc ccttggacac gctcagtggg gcagaggcag   2075
tacctgggca agctggcggc tggggtccca gcagctgcca ggagcacggc tctgtcccca   2135
gcctgggaaa gcccctgccc ctcctctccc tcatcaagga cacgggcctg tccacaggct   2195
tctgagcagc gagcctgcta gtggccgaac cagaaccaat tattttcatc cttgtcttat   2255
tcccttcctg ccagcccctg ccattgtagc gtctttcttt tttggccatc tgctcctgga   2315
tctccctgag atgggcttcc caagggctgc cggggcagcc ccctcacagt attgctcacc   2375
cagtgccctc tcccctcagc ctctcccctg cctgccctgg tgacatcagg ttttcccgg    2435 acttagaaaa ccagctcagc actgcctgct cccatcctgt gtgttaagct ctgctattag   2495
gccagcaagc ggggatgtcc ctgggaggga catgcttagc agtcccttc cctccaagaa    2555 ggatttggtc cgtcataacc caaggtacca tcctaggctg acacctaact cttctttcat   2615
ttcttctaca actcatacac tcgtatgata cttcgacact gttcttagct caatgagcat   2675
gtttagactt taacataagc tatttttcta actacaaagg tttaaatgaa caagagaagc   2735
attctcattg gaaatttagc attgtagtgc tttgagagag aaaggactcc tgaaaaaaaa   2795
cctgagattt attaaagaaa aaatgtatt ttatgttata tataaatata ttattacttg    2855
taaatataaa gacgttttat aagcatcatt atttatgtat tgtgcaatgt gtataaacaa   2915
gaaaaataaa gaaagatgc actttgcttt aatataaatg caaataacaa atgccaaatt    2975
aaaaaagata aacacaagat tggtgttttt tcctatgggt gttatcacct agctgaatgt   3035
ttttctaaag gagtttatgt tccattaaac gattttaaa atgtacactt gaaaaaaaa    3095 aaaaaaaa                                                         3103
```

<210> SEQ ID NO 3
<211> LENGTH: 1393
<212> TYPE: DNA
<213> ORGANISM: Homo sapiens
<220> FEATURE:
<221> NAME/KEY: CDS
<222> LOCATION: (90)...(938)

<400> SEQUENCE: 3

```
ggcacgaggt tgccctggcg gagcagagac aggccctcgg ggtggaggtc tttggtttca    60
taagagcctg agagagattt ttctaagat atg tgt aac aca cca acg tac tgt     113
                                 Met Cys Asn Thr Pro Thr Tyr Cys
                                  1               5 gac cta gga aag gct gct aag gat gtc ttc aac aaa gga tat ggc ttt     161
Asp Leu Gly Lys Ala Ala Lys Asp Val Phe Asn Lys Gly Tyr Gly Phe
     10              15                  20 ggc atg gtc aag ata gac ctg aaa acc aag tct tgt agt gga gtg gaa    209
```

```
Gly Met Val Lys Ile Asp Leu Lys Thr Lys Ser Cys Ser Gly Val Glu
 25                  30                  35                  40 ttt tct act tct ggt cat gct tac act gat aca ggg aaa gca tca ggc      257
Phe Ser Thr Ser Gly His Ala Tyr Thr Asp Thr Gly Lys Ala Ser Gly
                 45                  50                  55 aac cta gaa acc aaa tat aag gtc tgt aac tat gga ctt acc ttc acc      305
Asn Leu Glu Thr Lys Tyr Lys Val Cys Asn Tyr Gly Leu Thr Phe Thr
             60                  65                  70 cag aaa tgg aac aca gac aat act cta ggg aca gaa atc tct tgg gag      353
Gln Lys Trp Asn Thr Asp Asn Thr Leu Gly Thr Glu Ile Ser Trp Glu
         75                  80                  85 aat aag ttg gct gaa ggg ttg aaa ctg act ctt gat acc ata ttt gta      401
Asn Lys Leu Ala Glu Gly Leu Lys Leu Thr Leu Asp Thr Ile Phe Val
     90                  95                 100 ccg aac aca gga aag aag agt ggg aaa ttg aag gcc tcc tat aaa cgg      449
Pro Asn Thr Gly Lys Lys Ser Gly Lys Leu Lys Ala Ser Tyr Lys Arg
105                 110                 115                 120 gat tgt ttt agt gtt ggc agt aat gtt gat ata gat ttt tct gga cca      497
Asp Cys Phe Ser Val Gly Ser Asn Val Asp Ile Asp Phe Ser Gly Pro
                125                 130                 135 acc atc tat ggc tgg gct gtg ttg gcc ttc gaa ggg tgg ctt gct ggc      545
Thr Ile Tyr Gly Trp Ala Val Leu Ala Phe Glu Gly Trp Leu Ala Gly
            140                 145                 150 tat cag atg agt ttt gac aca gcc aaa tcc aaa ctg tca cag aat aat      593
Tyr Gln Met Ser Phe Asp Thr Ala Lys Ser Lys Leu Ser Gln Asn Asn
        155                 160                 165 ttc gcc ctg ggt tac aag gct gcg gac ttc cag ctg cac aca cat gtg      641
Phe Ala Leu Gly Tyr Lys Ala Ala Asp Phe Gln Leu His Thr His Val
    170                 175                 180 aac gat ggc act gaa ttt gga ggt tct atc tac cag aag gtg aat gag      689
Asn Asp Gly Thr Glu Phe Gly Gly Ser Ile Tyr Gln Lys Val Asn Glu
185                 190                 195                 200 aag att gaa aca tcc ata aac ctt gct tgg aca gct ggg agt aac aac      737
Lys Ile Glu Thr Ser Ile Asn Leu Ala Trp Thr Ala Gly Ser Asn Asn
                205                 210                 215 acc cgt ttt ggc att gct gct aag tac atg ctg gat tgt aga act tct      785
Thr Arg Phe Gly Ile Ala Ala Lys Tyr Met Leu Asp Cys Arg Thr Ser
            220                 225                 230 ctc tct gct aaa gta aat aat gcc agc ctg att gga ctg ggt tat act      833
Leu Ser Ala Lys Val Asn Asn Ala Ser Leu Ile Gly Leu Gly Tyr Thr
        235                 240                 245 cag acc ctt cga cca gga gtc aaa ttg act tta tca gct tta atc gat      881
Gln Thr Leu Arg Pro Gly Val Lys Leu Thr Leu Ser Ala Leu Ile Asp
    250                 255                 260 ggg aag aac ttc agt gca gga ggt cac aag gtt ggc ttg gga ttt gaa      929
Gly Lys Asn Phe Ser Ala Gly Gly His Lys Val Gly Leu Gly Phe Glu
265                 270                 275                 280 ctg gaa gct taatgtggtt tgaggaaagc atcagatttg tccctggaag              978
Leu Glu Ala tgaagagaaa tgaacccact atgttttggc cttaaaattc ttctgtgaaa tttcaaaagt    1038
gtgaactttt tattcttcca agaattgta atcctcccca cactgaagtc tagggggttgc   1098 gaatccctcc tgagggagac gcttgaaggc atgcctggaa gttgtcatgt ttgtgccacg    1158
tttcagttca gttctgaagt gttattaaat gtgttcctca gcgacagtgt agcgtcatgt    1218
tagaggagac gatctgaccc accagtttgt acatcacgtc ctgcatgtcc cacaccattt    1278
tttcatgacc ttgtaatata ctggtctctg tgctatagtg gaatctttgg ttttgcatca   1338
tagtaaaata aaataaaccc atcacatttg gaacataaaa aaaaaaaaaa aaaaa         1393
```

```
<210> SEQ ID NO 4
<211> LENGTH: 1036
<212> TYPE: DNA
<213> ORGANISM: Homo sapiens
<220> FEATURE:
<221> NAME/KEY: CDS
<222> LOCATION: (1)...(543)
<221> NAME/KEY: misc_feature
<222> LOCATION: (1)...(1036)
<223> OTHER INFORMATION: n = A,T,C or G

<400> SEQUENCE: 4
```

| | | | | | | | | | | | | | | | | |
|---|---|---|---|---|---|---|---|---|---|---|---|---|---|---|---|---|
| acg | agc | cta | gcc | ctg | gtg | ctc | aac | ctg | ctg | cag | atc | cag | agg | aat | gtc | 48 |
| Thr | Ser | Leu | Ala | Leu | Val | Leu | Asn | Leu | Leu | Gln | Ile | Gln | Arg | Asn | Val | |
| 1 | | | | 5 | | | | | 10 | | | | | 15 | | |
| act | ctc | ttc | ccc | gag | gag | gtg | atc | gcc | acc | atc | ttt | tcc | tcc | gcc | tgg | 96 |
| Thr | Leu | Phe | Pro | Glu | Glu | Val | Ile | Ala | Thr | Ile | Phe | Ser | Ser | Ala | Trp | |
| | | | 20 | | | | | 25 | | | | | 30 | | | |
| tgg | gtc | cct | ccc | tgc | tgc | ggg | aca | gca | gct | gct | gtt | gtt | ggc | cta | ctg | 144 |
| Trp | Val | Pro | Pro | Cys | Cys | Gly | Thr | Ala | Ala | Ala | Val | Val | Gly | Leu | Leu | |
| | 35 | | | | | 40 | | | | | 45 | | | | | |
| tac | ccc | tgt | atc | gac | agt | cac | ctc | gga | gaa | ccc | cac | aaa | ttt | aag | aga | 192 |
| Tyr | Pro | Cys | Ile | Asp | Ser | His | Leu | Gly | Glu | Pro | His | Lys | Phe | Lys | Arg | |
| 50 | | | | | 55 | | | | | 60 | | | | | | |
| gaa | tgg | gcc | agt | gtc | atg | cgc | tgc | ata | gca | gtt | ttt | gtt | ggc | att | aac | 240 |
| Glu | Trp | Ala | Ser | Val | Met | Arg | Cys | Ile | Ala | Val | Phe | Val | Gly | Ile | Asn | |
| 65 | | | | 70 | | | | | 75 | | | | | 80 | | |
| cac | gcc | agt | gct | aaa | ttg | gat | ttt | gcc | aat | aat | gtc | cag | ctg | tcc | ttg | 288 |
| His | Ala | Ser | Ala | Lys | Leu | Asp | Phe | Ala | Asn | Asn | Val | Gln | Leu | Ser | Leu | |
| | | | 85 | | | | | 90 | | | | | 95 | | | |
| act | tta | gca | gcc | cta | tct | ttg | ggc | ctt | tgg | tgg | aca | ttt | gat | cgt | tcc | 336 |
| Thr | Leu | Ala | Ala | Leu | Ser | Leu | Gly | Leu | Trp | Trp | Thr | Phe | Asp | Arg | Ser | |
| | | 100 | | | | | 105 | | | | | 110 | | | | |
| aga | agt | ggc | ctt | ggg | ctg | ggg | atc | acc | ata | gct | ttt | cta | gct | acg | ctg | 384 |
| Arg | Ser | Gly | Leu | Gly | Leu | Gly | Ile | Thr | Ile | Ala | Phe | Leu | Ala | Thr | Leu | |
| | 115 | | | | | 120 | | | | | 125 | | | | | |
| atc | acg | cag | ttt | ctc | gtg | tat | aat | ggt | gtc | tat | cag | tat | aca | tcc | cca | 432 |
| Ile | Thr | Gln | Phe | Leu | Val | Tyr | Asn | Gly | Val | Tyr | Gln | Tyr | Thr | Ser | Pro | |
| 130 | | | | | 135 | | | | | 140 | | | | | | |
| gat | ttc | ctc | tat | att | cgt | tct | tgg | ctc | cct | tgt | ata | ttt | ttc | tca | gga | 480 |
| Asp | Phe | Leu | Tyr | Ile | Arg | Ser | Trp | Leu | Pro | Cys | Ile | Phe | Phe | Ser | Gly | |
| 145 | | | | 150 | | | | | 155 | | | | | 160 | | |
| ggc | gtc | acg | gtg | ggg | aac | ata | gga | cga | cag | tta | gct | atg | ggt | gtt | cct | 528 |
| Gly | Val | Thr | Val | Gly | Asn | Ile | Gly | Arg | Gln | Leu | Ala | Met | Gly | Val | Pro | |
| | | | 165 | | | | | 170 | | | | | 175 | | | |

| | | |
|---|---|---|
| gaa aag ccc cat agt gattgagtct tcaaaaccac cgattctgag agcaaggaag | 583 | |
| Glu Lys Pro His Ser | | |
| 180 | | |
| attttggaag aaaatctgac tgtggattat gacaaagatt atcttttttc ttaagtaatc | 643 | |
| tatttagatc gggctgactg tacaaatgac tcctggaaaa aactcttcac ctagtctaga | 703 | |
| ataggaggt ggagaatgat gacttaccct gaagtcttcc cttgactgcc cgcactggcg | 763 | |
| cctgtctgtg ccctggagca ttctgcccag gctacgtggg ttcaggcagg tggcagcttc | 823 | |
| ccaagtattc gatttcattc atgtgattaa aacaagttgc catatttcaa aaaaaaaaa | 883 | |
| aaaaamctcg agaccaaccc gcagtttgt gtcagtgccc aaaggaggta ggttgatggt | 943 | |
| gcttaacaaa catgaagtat ggtgtaatag gaataatatt tatccnaaag attttaaaa | 1003 | |
| ataggctgt gtttaaaaaa aaaaaaaaaa aaa | 1036 | |

<210> SEQ ID NO 5
<211> LENGTH: 1228
<212> TYPE: DNA
<213> ORGANISM: Homo sapiens
<220> FEATURE:
<221> NAME/KEY: CDS
<222> LOCATION: (1)...(468)

<400> SEQUENCE: 5

| | | |
|---|---|---|
| atg tgt cac tct cgc agc tgc cac ccg acc atg acc atc ctg cag gcc<br>Met Cys His Ser Arg Ser Cys His Pro Thr Met Thr Ile Leu Gln Ala<br>1                        5                       10                    15 | 48 |
| ccg acc ccg gcc ccc tcc acc atc ccg gga ccc cgg cgg ggc tcc ggt<br>Pro Thr Pro Ala Pro Ser Thr Ile Pro Gly Pro Arg Arg Gly Ser Gly<br>             20                     25                     30 | 96 |
| cct gag atc ttc acc ttc gac cct ctc ccg gag ccc gca gcg gcc cct<br>Pro Glu Ile Phe Thr Phe Asp Pro Leu Pro Glu Pro Ala Ala Ala Pro<br>           35                     40                    45 | 144 |
| gcc ggg cgc ccc agc gcc tct cgc ggg cac cga aag cgc agc cgc agg<br>Ala Gly Arg Pro Ser Ala Ser Arg Gly His Arg Lys Arg Ser Arg Arg<br>50                      55                     60 | 192 |
| gtt ctc tac cct cga gtg gtc cgg cgc cag ctg cca gtc gag gaa ccg<br>Val Leu Tyr Pro Arg Val Val Arg Arg Gln Leu Pro Val Glu Glu Pro<br>65                      70                     75                    80 | 240 |
| aac cca gcc aaa agg ctt ctc ttt ctg ctg ctc acc atc gtc ttc tgc<br>Asn Pro Ala Lys Arg Leu Leu Phe Leu Leu Leu Thr Ile Val Phe Cys<br>                   85                     90                    95 | 288 |
| cag atc ctg atg gct gaa gag ggt gtg ccg gcg ccc ctg cct cca gag<br>Gln Ile Leu Met Ala Glu Glu Gly Val Pro Ala Pro Leu Pro Pro Glu<br>                 100                   105                 110 | 336 |
| gac gcc cct aac gcc gca tcc ctg gcg ccc acc cct gtg tcc ccc gtc<br>Asp Ala Pro Asn Ala Ala Ser Leu Ala Pro Thr Pro Val Ser Pro Val<br>           115                    120                   125 | 384 |
| ctc gag ccc ttt aat ctg act tcg gag ccc tcg gac tac gct ctg gac<br>Leu Glu Pro Phe Asn Leu Thr Ser Glu Pro Ser Asp Tyr Ala Leu Asp<br>130                    135                    140 | 432 |
| ctc agc act ttc ctc cag caa cac ccg gcc gcc ttc taactgtgac<br>Leu Ser Thr Phe Leu Gln Gln His Pro Ala Ala Phe<br>145                    150                    155 | 478 |
| tccccgcact ccccaaaaag aatccgaaaa accacaaaga aacaccaggc gtacctggtg | 538 |
| cgcgagagcg tatccccaac tgggacttcc gaggcaactt gaactcagaa cactacagcg | 598 |
| gagacgccac ccggtgcttg aggcgggacc gaggcgcaca gagaccgagg cgcatagaga | 658 |
| ccgaggcaca gcccagctgg ggctaggccc ggtgggaagg agagcgtcgt taatttattt | 718 |
| cttattgctc ctaattaata tttatatgta tttatgtacg tcctcctagg tgatggagat | 778 |
| gtgtacgtaa tatttatttt aacttatgca agggtgtgag atgttccctc tgctgtaaat | 838 |
| gcaggtctct tggtatttat tgagctttgt gggactggtg gaagcaggac acctggaact | 898 |
| gcggcaaagt aggagaagaa atggggagga ctcgggtggg ggaggacgtc ccggctggga | 958 |
| tgaagtctgg tggtgggtcg taagtttagg aggtgactgc atcctccagc atctcaactc | 1018 |
| cgtctgtcta ctgtgtgaga cttcggcgga ccattaggaa tgagatccgt gagatccttc | 1078 |
| catcttcttg aagtcgccct tagggtggct gcgaggtaga gggttggggg ttgtgggct | 1138 |
| gtcacggagc gactgtcgag atcgcctagt atgttctgtg aacacaaata aaattgattt | 1198 |
| actgtcaaaa aaaaaaaaaa aaaactcgag | 1228 |

<210> SEQ ID NO 6

```
<211> LENGTH: 3084
<212> TYPE: DNA
<213> ORGANISM: Homo sapiens
<220> FEATURE:
<221> NAME/KEY: CDS
<222> LOCATION: (1032)...(1736)

<400> SEQUENCE: 6
gaattcggca cgaggmcagg agctcctttw ctgcgtctcc catcatgggg cttaggttg      60 agtcttcagg ttctgggggc aggaaggacg ggcactcagg aggccccctc cccatccaca    120
gcccctcttt ggagggggg aaacttggca acccggagg catgtggatc ttttcctaag      180
caagatgctg agctggaaag atggggtgt aaggtaatgt cccaaactga aactttgcca    240
ggcactggga gaggctgtga actcttttct ggctttagaa tttaggtcta gatcccaaaa    300
ggctaagtac ccctggggg ctaaccagag gcatgcctgg gctgagctga accttctggt    360
gcactggccc ctggctgact gctcttctgc aggaagttgg aggagattcc tgaagttgat    420
tcctcaggct ggatgtccaa gggggttgga gtttctgatg tctttctgtc tccctctctt    480
ttctttctct ccctaccagg tccacttctt tcagaggggc ctgcggtgct ctaaaagttc    540
tcctgttaaa gtttagagca aattggttat tattttaaaa tcaataaaac ttttaaaagt    600
actaagacaa cttctaagag gggagtggac agagggcctg gtggcagctc acagtttctt    660
ttctgacctt tggtctcacc caccaagtgt cccacctgag tgcccacctt gcccacctga    720
ggtaatgccc tggggctcca ccagtccaga tccacagggc gcarccatgt gggagtggcg    780
gctgattgtt acccagtagt gttgatagca cattattcat aacagccaaa gagaggaagc    840
aacccaaatg tccattagct gataaatgga taaatgaaat atggtacgtc cgaagaatgg    900
aatatcattc acccatgaaa aagaacgaag tccagcacca aaacgtgcta acatggat     960 gaacttcgat gactttgtgc cacatgaaag aagaagccag ccacaaaagg ccatatattg   1020
tatgaaatga a atg tcc aga atg ggc aaa ccc ata gag aca caa aaa tct   1070
            Met Ser Arg Met Gly Lys Pro Ile Glu Thr Gln Lys Ser
              1               5                  10 ccg cca cct ccc tac tct cgg ctg tct cct cgc gac gag tac aag cca   1118
Pro Pro Pro Pro Tyr Ser Arg Leu Ser Pro Arg Asp Glu Tyr Lys Pro
 15              20                  25 ctg gat ctg tcc gat tcc aca ttg tct tac act gaa acg gag gct acc   1166
Leu Asp Leu Ser Asp Ser Thr Leu Ser Tyr Thr Glu Thr Glu Ala Thr
 30              35                  40                  45 aac tcc ctc atc act gct ccg ggt gaa ttc tca gac gcc agc atg tct   1214
Asn Ser Leu Ile Thr Ala Pro Gly Glu Phe Ser Asp Ala Ser Met Ser
                 50                  55                  60 ccg gac gcc acc aag ccg agc cac tgg tgc agc gtg gcg tac tgg gag   1262
Pro Asp Ala Thr Lys Pro Ser His Trp Cys Ser Val Ala Tyr Trp Glu
             65                  70                  75 cac cgg acg cgc gtg ggc cgc ctc tat gcg gtg tac gac cag gcc gtc   1310
His Arg Thr Arg Val Gly Arg Leu Tyr Ala Val Tyr Asp Gln Ala Val
         80                  85                  90 agc atc ttc tac gac cta cct cag ggc agc ggc ttc tgc ctg ggc cag   1358
Ser Ile Phe Tyr Asp Leu Pro Gln Gly Ser Gly Phe Cys Leu Gly Gln
     95                 100                 105 ctc aac ctg gag cag cgc agc gag tcg gtg cgg cga acg cgc agc aag   1406
Leu Asn Leu Glu Gln Arg Ser Glu Ser Val Arg Arg Thr Arg Ser Lys
110             115                 120                 125 atc ggc ttc ggc atc ctg ctc agc aag gag ccc gac ggc gtg tgg gcc   1454
Ile Gly Phe Gly Ile Leu Leu Ser Lys Glu Pro Asp Gly Val Trp Ala
                130                 135                 140
```

```
tac aac cgc ggc gag cac ccc atc ttc gtc aac tcc ccg acg ctg gac      1502
Tyr Asn Arg Gly Glu His Pro Ile Phe Val Asn Ser Pro Thr Leu Asp
        145                 150                 155 gcg ccc ggc ggc cgc gcc ctg gtc gtg cgc aag gtg ccc ccc ggc tac      1550
Ala Pro Gly Gly Arg Ala Leu Val Val Arg Lys Val Pro Pro Gly Tyr
160                 165                 170 tcc atc aag gtg ttc gac ttc gag cgc tcg ggc ctg cag cac gcg ccc      1598
Ser Ile Lys Val Phe Asp Phe Glu Arg Ser Gly Leu Gln His Ala Pro
        175                 180                 185 gag ccc gac gcc gcc gac ggc ccc tac gac ccc aac agc gtc cgc atc      1646
Glu Pro Asp Ala Ala Asp Gly Pro Tyr Asp Pro Asn Ser Val Arg Ile
190                 195                 200                 205 agc ttc gcc aag ggc tgg ggg ccc tgc tac tcc cgg cag ttc atc acc      1694
Ser Phe Ala Lys Gly Trp Gly Pro Cys Tyr Ser Arg Gln Phe Ile Thr
                210                 215                 220 tcc tgc ccc tgc tgg ctg gag atc ctc ctc aac aac ccc aga              1736
Ser Cys Pro Cys Trp Leu Glu Ile Leu Leu Asn Asn Pro Arg
            225                 230                 235 tagtggcggc cccggcggga ggggcgggtg ggaggccgcg gccaccgcca cctgccggcc    1796
tcgagagggg ccgatgccca gagacacagc ccccacggac aaaacccccc agatatcatc    1856
tacctagatt taatataaag ttttatatat tatatggaaa tatatattat acttgtaatt    1916
atggagtcat ttttacaatg taattattta tgtatggtgc aatgtgtgta tatggacaaa    1976
acaagaaaga cgcactttgg cttataattc tttcaataca gatatatttt ctttctcttc    2036
ctccttcctc ttccttactt tttatatata tatataaaga aaatgataca gcagagctag    2096
gtggaaaagc ctgggtttgg tgtatggttt tgagatatt aatgcccaga caaaaagcta     2156
ataccagtca ctcgataata aagtattcgc attatagttt tttttaaact gtcttctttt    2216
tacaaagagg ggcaggtagg gcttcagcgg atttctgacc catcatgtac cttgaaactt    2276
gacctcagtt ttcaagtttt actttttattg gataaagaca gaacaaattg aaaagggagg   2336
aaagtcacat ttactcttaa gtaaaccaga gaaagttctg ttgttccttc ctgcccatgg    2396
ctatggggtg tccagtggat agggatggcg gtggggaaaa ggagaataca ctggccattt    2456
atcctggaca agctcttcca gtctgatgga ggaggttcat gccctagcct agaaaggccc    2516
aggtccatga ccccatctt tgagttatga gcaagctaaa agaagacact atttctcacc     2576
attttgtgga aatggcctgg ggaacaaaga ctgaaatggg ccttgagccc acctgctacc    2636
ttgcagagaa ccatctcgag ccccgtagat cttttttagga cctccacagg statttccca   2696 cccccccagcc aaaaatagct cagaatctgc ccatccaggg cttgtattaa tgatttatgt   2756
aaaggcagat ggtttatttc tactttgtaa aagggaaaag ttgaggttct ggaaggataa    2816
atgatttgct catgagacaa aatcaaggtt agaagttaca tggaattgta ggaccagagc    2876
catatcatta gatcagcttt ctgaagaata ttctccamaa aagaaagtct ccttggccag    2936
ataactaaga ggaatgtttc attgtatatc tttttcttg gagatttata ttaacatatt     2996
aagtgctctg agaagtcctg tgtattatct cttgctgcat aataaattat ccccamactt    3056
aaaaaaaaaa aaaaaaaaa aactcgag                                        3084

<210> SEQ ID NO 7
<211> LENGTH: 570
<212> TYPE: PRT
<213> ORGANISM: Homo sapiens

<400> SEQUENCE: 7

Met Pro Gly Glu Thr Glu Glu Pro Arg Pro Pro Glu Gln Gln Asp Gln
```

-continued

```
  1               5                  10                 15
Glu Gly Gly Glu Ala Ala Lys Ala Ala Pro Glu Pro Gln Gln Arg
             20              25              30
Pro Pro Glu Ala Val Ala Ala Pro Ala Gly Thr Thr Ser Ser Arg
         35              40              45
Val Leu Arg Gly Gly Arg Asp Arg Gly Arg Ala Ala Ala Ala Ala
 50              55              60
Ala Ala Ala Val Ser Arg Arg Lys Ala Glu Tyr Pro Arg Arg Arg
 65              70              75              80
Arg Ser Ser Pro Ser Ala Arg Pro Pro Asp Val Pro Gly Gln Gln Pro
             85              90              95
Gln Ala Ala Lys Ser Pro Ser Pro Val Gln Gly Lys Lys Ser Pro Arg
            100             105             110
Leu Leu Cys Ile Glu Lys Val Thr Thr Asp Lys Asp Pro Lys Glu Glu
            115             120             125
Lys Glu Glu Glu Asp Asp Ser Ala Leu Pro Gln Glu Val Ser Ile Ala
            130             135             140
Ala Ser Arg Pro Ser Arg Gly Trp Arg Ser Ser Arg Thr Ser Val Ser
145             150             155             160
Arg His Arg Asp Thr Glu Asn Thr Arg Ser Ser Arg Ser Lys Thr Gly
            165             170             175
Ser Leu Gln Leu Ile Cys Lys Ser Glu Pro Asn Thr Asp Gln Leu Asp
            180             185             190
Tyr Asp Val Gly Glu Glu His Gln Ser Pro Gly Gly Ile Ser Gly Glu
            195             200             205
Glu Glu Glu Glu Glu Glu Glu Met Leu Ile Ser Glu Glu Glu Ile
            210             215             220
Pro Phe Lys Asp Asp Pro Arg Asp Glu Thr Tyr Lys Pro His Leu Glu
225             230             235             240
Arg Glu Thr Pro Lys Pro Arg Arg Lys Ser Gly Lys Val Lys Glu Glu
            245             250             255
Lys Glu Lys Lys Glu Ile Lys Val Glu Val Glu Val Glu Val Lys Glu
            260             265             270
Glu Glu Asn Glu Ile Arg Glu Asp Glu Glu Pro Pro Arg Lys Arg Gly
            275             280             285
Arg Arg Arg Lys Asp Asp Lys Ser Pro Arg Leu Pro Lys Arg Arg Lys
290             295             300
Lys Pro Pro Ile Gln Tyr Val Arg Cys Glu Met Glu Gly Cys Gly Thr
305             310             315             320
Val Leu Ala His Pro Arg Tyr Leu Gln His His Ile Lys Tyr Gln His
            325             330             335
Leu Leu Lys Lys Lys Tyr Val Cys Pro His Pro Ser Cys Gly Arg Leu
            340             345             350
Phe Arg Leu Gln Lys Gln Leu Leu Arg His Ala Lys His His Thr Asp
            355             360             365
Gln Arg Asp Tyr Ile Cys Glu Tyr Cys Ala Arg Ala Phe Lys Ser Ser
            370             375             380
His Asn Leu Ala Val His Arg Met Ile His Thr Gly Glu Lys Pro Leu
385             390             395             400
Gln Cys Glu Ile Cys Gly Phe Thr Cys Arg Gln Lys Ala Ser Leu Asn
            405             410             415
Trp His Met Lys Lys His Asp Ala Asp Ser Phe Tyr Gln Phe Ser Cys
            420             425             430
```

-continued

```
Asn Ile Cys Gly Lys Lys Phe Glu Lys Asp Ser Val Val Ala His
        435                 440                 445

Lys Ala Lys Ser His Pro Glu Val Leu Ile Ala Glu Ala Leu Ala Ala
    450                 455                 460

Asn Ala Gly Ala Leu Ile Thr Ser Thr Asp Ile Leu Gly Thr Asn Pro
465                 470                 475                 480

Glu Ser Leu Thr Gln Pro Ser Asp Gly Gln Gly Leu Pro Leu Leu Pro
                485                 490                 495

Glu Pro Leu Gly Asn Ser Thr Ser Gly Glu Cys Leu Leu Glu Ala
                500                 505                 510

Glu Gly Met Ser Lys Ser Tyr Cys Ser Gly Thr Glu Arg Val Ser Leu
                515                 520                 525

Met Ala Asp Gly Lys Ile Phe Val Gly Ser Gly Ser Ser Gly Gly Thr
    530                 535                 540

Glu Gly Leu Val Met Asn Ser Asp Ile Leu Gly Ala Thr Thr Glu Val
545                 550                 555                 560

Leu Ile Glu Asp Ser Asp Ser Ala Gly Pro
                565                 570

<210> SEQ ID NO 8
<211> LENGTH: 426
<212> TYPE: PRT
<213> ORGANISM: Homo sapiens

<400> SEQUENCE: 8

Met Phe Arg Thr Lys Arg Ser Ala Leu Val Arg Arg Leu Trp Arg Ser
1               5                   10                  15

Arg Ala Pro Gly Gly Glu Asp Glu Glu Gly Ala Gly Gly Gly
            20                  25                  30

Gly Gly Gly Glu Leu Arg Gly Gly Ala Thr Asp Ser Arg Ala His
        35                  40                  45

Gly Ala Gly Gly Gly Pro Gly Arg Ala Gly Cys Cys Leu Gly Lys
    50                  55                  60

Ala Val Arg Gly Ala Lys Gly His His Pro His Pro Ala Ala
65              70                  75                  80

Gly Ala Gly Ala Ala Gly Gly Ala Glu Ala Asp Leu Lys Ala Leu Thr
                85                  90                  95

His Ser Val Leu Lys Lys Leu Lys Glu Arg Gln Leu Glu Leu Leu
                100                 105                 110

Gln Ala Val Glu Ser Arg Gly Gly Thr Arg Thr Ala Cys Leu Leu Leu
                115                 120                 125

Pro Gly Arg Leu Asp Cys Arg Leu Gly Pro Gly Ala Pro Ala Gly Ala
                130                 135                 140

Gln Pro Ala Gln Pro Pro Ser Ser Tyr Ser Leu Pro Leu Leu Leu Cys
145                 150                 155                 160

Lys Val Phe Arg Trp Pro Asp Leu Arg His Ser Ser Glu Val Lys Arg
                165                 170                 175

Leu Cys Cys Cys Glu Ser Tyr Gly Lys Ile Asn Pro Glu Leu Val Cys
                180                 185                 190

Cys Asn Pro His His Leu Ser Arg Leu Cys Glu Leu Glu Ser Pro Pro
                195                 200                 205

Pro Pro Tyr Ser Arg Tyr Pro Met Asp Phe Leu Lys Pro Thr Ala Asp
                210                 215                 220

Cys Pro Asp Ala Val Pro Ser Ser Ala Glu Thr Gly Gly Thr Asn Tyr
```

-continued

```
                225                 230                 235                 240
Leu Ala Pro Gly Gly Leu Ser Asp Ser Gln Leu Leu Glu Pro Gly
                    245                 250                 255
Asp Arg Ser His Trp Cys Val Val Ala Tyr Trp Glu Lys Thr Arg
                260                 265                 270
Val Gly Arg Leu Tyr Cys Val Gln Glu Pro Ser Leu Asp Ile Phe Tyr
            275                 280                 285
Asp Leu Pro Gln Gly Asn Gly Phe Cys Leu Gly Gln Leu Asn Ser Asp
    290                 295                 300
Asn Lys Ser Gln Leu Val Gln Lys Val Arg Ser Lys Ile Gly Cys Gly
305                 310                 315                 320
Ile Gln Leu Thr Arg Glu Val Asp Gly Val Trp Val Tyr Asn Arg Ser
                325                 330                 335
Ser Tyr Pro Ile Phe Ile Lys Ser Ala Thr Leu Asp Asn Pro Asp Ser
                340                 345                 350
Arg Thr Leu Leu Val His Lys Val Phe Pro Gly Phe Ser Ile Lys Ala
                355                 360                 365
Phe Asp Tyr Glu Lys Ala Tyr Ser Leu Gln Arg Pro Asn Asp His Glu
    370                 375                 380
Phe Met Gln Gln Pro Trp Thr Gly Phe Thr Val Gln Ile Ser Phe Val
385                 390                 395                 400
Lys Gly Trp Gly Gln Cys Tyr Thr Arg Gln Phe Ile Ser Ser Cys Pro
                405                 410                 415
Cys Trp Leu Glu Val Ile Phe Asn Ser Arg
                420                 425

<210> SEQ ID NO 9
<211> LENGTH: 283
<212> TYPE: PRT
<213> ORGANISM: Homo sapiens

<400> SEQUENCE: 9

Met Cys Asn Thr Pro Thr Tyr Cys Asp Leu Gly Lys Ala Ala Lys Asp
1               5                   10                  15
Val Phe Asn Lys Gly Tyr Gly Phe Gly Met Val Lys Ile Asp Leu Lys
                20                  25                  30
Thr Lys Ser Cys Ser Gly Val Glu Phe Ser Thr Ser Gly His Ala Tyr
            35                  40                  45
Thr Asp Thr Gly Lys Ala Ser Gly Asn Leu Glu Thr Lys Tyr Lys Val
    50                  55                  60
Cys Asn Tyr Gly Leu Thr Phe Thr Gln Lys Trp Asn Thr Asp Asn Thr
65                  70                  75                  80
Leu Gly Thr Glu Ile Ser Trp Glu Asn Lys Leu Ala Glu Gly Leu Lys
                85                  90                  95
Leu Thr Leu Asp Thr Ile Phe Val Pro Asn Thr Gly Lys Lys Ser Gly
                100                 105                 110
Lys Leu Lys Ala Ser Tyr Lys Arg Asp Cys Phe Ser Val Gly Ser Asn
            115                 120                 125
Val Asp Ile Asp Phe Ser Gly Pro Thr Ile Tyr Gly Trp Ala Val Leu
    130                 135                 140
Ala Phe Glu Gly Trp Leu Ala Gly Tyr Gln Met Ser Phe Asp Thr Ala
145                 150                 155                 160
Lys Ser Lys Leu Ser Gln Asn Asn Phe Ala Leu Gly Tyr Lys Ala Ala
                165                 170                 175
```

-continued

Asp Phe Gln Leu His Thr His Val Asn Asp Gly Thr Glu Phe Gly Gly
                180                 185                 190

Ser Ile Tyr Gln Lys Val Asn Glu Lys Ile Glu Thr Ser Ile Asn Leu
            195                 200                 205

Ala Trp Thr Ala Gly Ser Asn Asn Thr Arg Phe Gly Ile Ala Ala Lys
        210                 215                 220

Tyr Met Leu Asp Cys Arg Thr Ser Leu Ser Ala Lys Val Asn Asn Ala
225                 230                 235                 240

Ser Leu Ile Gly Leu Gly Tyr Thr Gln Thr Leu Arg Pro Gly Val Lys
                245                 250                 255

Leu Thr Leu Ser Ala Leu Ile Asp Gly Lys Asn Phe Ser Ala Gly Gly
                260                 265                 270

His Lys Val Gly Leu Gly Phe Glu Leu Glu Ala
                275                 280

<210> SEQ ID NO 10
<211> LENGTH: 181
<212> TYPE: PRT
<213> ORGANISM: Homo sapiens

<400> SEQUENCE: 10

Thr Ser Leu Ala Leu Val Leu Asn Leu Leu Gln Ile Gln Arg Asn Val
1               5                   10                  15

Thr Leu Phe Pro Glu Val Ile Ala Thr Ile Phe Ser Ser Ala Trp
            20                  25                  30

Trp Val Pro Pro Cys Cys Gly Thr Ala Ala Val Val Gly Leu Leu
        35                  40                  45

Tyr Pro Cys Ile Asp Ser His Leu Gly Glu Pro His Lys Phe Lys Arg
    50                  55                  60

Glu Trp Ala Ser Val Met Arg Cys Ile Ala Val Phe Val Gly Ile Asn
65                  70                  75                  80

His Ala Ser Ala Lys Leu Asp Phe Ala Asn Asn Val Gln Leu Ser Leu
                85                  90                  95

Thr Leu Ala Ala Leu Ser Leu Gly Leu Trp Trp Thr Phe Asp Arg Ser
                100                 105                 110

Arg Ser Gly Leu Gly Leu Gly Ile Thr Ile Ala Phe Leu Ala Thr Leu
            115                 120                 125

Ile Thr Gln Phe Leu Val Tyr Asn Gly Val Tyr Gln Tyr Thr Ser Pro
130                 135                 140

Asp Phe Leu Tyr Ile Arg Ser Trp Leu Pro Cys Ile Phe Phe Ser Gly
145                 150                 155                 160

Gly Val Thr Val Gly Asn Ile Gly Arg Gln Leu Ala Met Gly Val Pro
                165                 170                 175

Glu Lys Pro His Ser
            180

<210> SEQ ID NO 11
<211> LENGTH: 156
<212> TYPE: PRT
<213> ORGANISM: Homo sapiens

<400> SEQUENCE: 11

Met Cys His Ser Arg Ser Cys His Pro Thr Met Thr Ile Leu Gln Ala
1               5                   10                  15

Pro Thr Pro Ala Pro Ser Thr Ile Pro Gly Pro Arg Arg Gly Ser Gly
            20                  25                  30

-continued

Pro Glu Ile Phe Thr Phe Asp Pro Leu Pro Glu Pro Ala Ala Pro
         35                  40                  45

Ala Gly Arg Pro Ser Ala Ser Arg Gly His Arg Lys Arg Ser Arg Arg
 50                  55                  60

Val Leu Tyr Pro Arg Val Val Arg Arg Gln Leu Pro Val Glu Glu Pro
 65              70                  75                  80

Asn Pro Ala Lys Arg Leu Leu Phe Leu Leu Thr Ile Val Phe Cys
             85                  90                  95

Gln Ile Leu Met Ala Glu Glu Gly Val Pro Ala Pro Leu Pro Pro Glu
             100                 105                 110

Asp Ala Pro Asn Ala Ala Ser Leu Ala Pro Thr Pro Val Ser Pro Val
             115                 120                 125

Leu Glu Pro Phe Asn Leu Thr Ser Glu Pro Ser Asp Tyr Ala Leu Asp
 130                 135                 140

Leu Ser Thr Phe Leu Gln Gln His Pro Ala Ala Phe
 145                 150                 155

<210> SEQ ID NO 12
<211> LENGTH: 235
<212> TYPE: PRT
<213> ORGANISM: Homo sapiens

<400> SEQUENCE: 12

Met Ser Arg Met Gly Lys Pro Ile Glu Thr Gln Lys Ser Pro Pro Pro
 1               5                   10                  15

Pro Tyr Ser Arg Leu Ser Pro Arg Asp Glu Tyr Lys Pro Leu Asp Leu
                 20                  25                  30

Ser Asp Ser Thr Leu Ser Tyr Thr Glu Thr Glu Ala Thr Asn Ser Leu
             35                  40                  45

Ile Thr Ala Pro Gly Glu Phe Ser Asp Ala Ser Met Ser Pro Asp Ala
 50                  55                  60

Thr Lys Pro Ser His Trp Cys Ser Val Ala Tyr Trp Glu His Arg Thr
 65                  70                  75                  80

Arg Val Gly Arg Leu Tyr Ala Val Tyr Asp Gln Ala Val Ser Ile Phe
                 85                  90                  95

Tyr Asp Leu Pro Gln Gly Ser Gly Phe Cys Leu Gly Gln Leu Asn Leu
                 100                 105                 110

Glu Gln Arg Ser Glu Ser Val Arg Arg Thr Arg Ser Lys Ile Gly Phe
             115                 120                 125

Gly Ile Leu Leu Ser Lys Glu Pro Asp Gly Val Trp Ala Tyr Asn Arg
 130                 135                 140

Gly Glu His Pro Ile Phe Val Asn Ser Pro Thr Leu Asp Ala Pro Gly
 145                 150                 155                 160

Gly Arg Ala Leu Val Val Arg Lys Val Pro Pro Gly Tyr Ser Ile Lys
                 165                 170                 175

Val Phe Asp Phe Glu Arg Ser Gly Leu Gln His Ala Pro Glu Pro Asp
                 180                 185                 190

Ala Ala Asp Gly Pro Tyr Asp Pro Asn Ser Val Arg Ile Ser Phe Ala
             195                 200                 205

Lys Gly Trp Gly Pro Cys Tyr Ser Arg Gln Phe Ile Thr Ser Cys Pro
 210                 215                 220

Cys Trp Leu Glu Ile Leu Leu Asn Asn Pro Arg
 225                 230                 235

<210> SEQ ID NO 13

-continued

```
<211> LENGTH: 12
<212> TYPE: DNA
<213> ORGANISM: Homo sapiens

<400> SEQUENCE: 13
tttttttttt tc                                                           12

<210> SEQ ID NO 14
<211> LENGTH: 10
<212> TYPE: DNA
<213> ORGANISM: Homo sapiens

<400> SEQUENCE: 14
gtgaggcgtc                                                              10

<210> SEQ ID NO 15
<211> LENGTH: 10
<212> TYPE: DNA
<213> ORGANISM: Homo sapiens

<400> SEQUENCE: 15
tggaccggtg                                                              10

<210> SEQ ID NO 16
<211> LENGTH: 12
<212> TYPE: DNA
<213> ORGANISM: Homo sapiens

<400> SEQUENCE: 16
tttttttttt ta                                                           12

<210> SEQ ID NO 17
<211> LENGTH: 10
<212> TYPE: DNA
<213> ORGANISM: Homo sapiens

<400> SEQUENCE: 17
agacgtccac                                                              10

<210> SEQ ID NO 18
<211> LENGTH: 10
<212> TYPE: DNA
<213> ORGANISM: Homo sapiens

<400> SEQUENCE: 18
acttcgccac                                                              10

<210> SEQ ID NO 19
<211> LENGTH: 10
<212> TYPE: DNA
<213> ORGANISM: Homo sapiens

<400> SEQUENCE: 19
tcggacgtga                                                              10

<210> SEQ ID NO 20
<211> LENGTH: 17
<212> TYPE: DNA
<213> ORGANISM: Homo sapiens

<400> SEQUENCE: 20
catttcattt catacaa                                                      17
```

```
<210> SEQ ID NO 21
<211> LENGTH: 23
<212> TYPE: DNA
<213> ORGANISM: Homo sapiens

<400> SEQUENCE: 21
catttcattt catacaatat atg                                              23

<210> SEQ ID NO 22
<211> LENGTH: 29
<212> TYPE: DNA
<213> ORGANISM: Homo sapiens

<400> SEQUENCE: 22
catttcattt catacaatat atggccttt                                        29

<210> SEQ ID NO 23
<211> LENGTH: 35
<212> TYPE: DNA
<213> ORGANISM: Homo sapiens

<400> SEQUENCE: 23
catttcattt catacaatat atggcctttt gtggc                                 35

<210> SEQ ID NO 24
<211> LENGTH: 35
<212> TYPE: DNA
<213> ORGANISM: Homo sapiens

<400> SEQUENCE: 24
ggacatttca tttcatacaa tatatggcct tttgt                                 35

<210> SEQ ID NO 25
<211> LENGTH: 29
<212> TYPE: DNA
<213> ORGANISM: Homo sapiens

<400> SEQUENCE: 25
ttcatttcat acaatatatg gcctttgt                                         29

<210> SEQ ID NO 26
<211> LENGTH: 23
<212> TYPE: DNA
<213> ORGANISM: Homo sapiens

<400> SEQUENCE: 26
tcatacaata tatggccttt tgt                                              23

<210> SEQ ID NO 27
<211> LENGTH: 17
<212> TYPE: DNA
<213> ORGANISM: Homo sapiens

<400> SEQUENCE: 27
aatatatggc cttttgt                                                     17

<210> SEQ ID NO 28
<211> LENGTH: 17
<212> TYPE: DNA
<213> ORGANISM: Homo sapiens

<400> SEQUENCE: 28
catgcggggc gaggagg                                                     17
```

```
<210> SEQ ID NO 29
<211> LENGTH: 23
<212> TYPE: DNA
<213> ORGANISM: Homo sapiens

<400> SEQUENCE: 29
catgcggggc gaggaggcga gga                                          23

<210> SEQ ID NO 30
<211> LENGTH: 29
<212> TYPE: DNA
<213> ORGANISM: Homo sapiens

<400> SEQUENCE: 30
catgcggggc gaggaggcga ggagaaaag                                    29

<210> SEQ ID NO 31
<211> LENGTH: 35
<212> TYPE: DNA
<213> ORGANISM: Homo sapiens

<400> SEQUENCE: 31
catgcggggc gaggaggcga ggagaaaagt cgttt                             35

<210> SEQ ID NO 32
<211> LENGTH: 35
<212> TYPE: DNA
<213> ORGANISM: Homo sapiens

<400> SEQUENCE: 32
gaacatgcgg ggcgaggagg cgaggagaaa agtcg                             35

<210> SEQ ID NO 33
<211> LENGTH: 29
<212> TYPE: DNA
<213> ORGANISM: Homo sapiens

<400> SEQUENCE: 33
gcggggcgag gaggcgagga gaaaagtcg                                    29

<210> SEQ ID NO 34
<211> LENGTH: 23
<212> TYPE: DNA
<213> ORGANISM: Homo sapiens

<400> SEQUENCE: 34
cgaggaggcg aggagaaaag tcg                                          23

<210> SEQ ID NO 35
<211> LENGTH: 17
<212> TYPE: DNA
<213> ORGANISM: Homo sapiens

<400> SEQUENCE: 35
ggcgaggaga aaagtcg                                                 17

<210> SEQ ID NO 36
<211> LENGTH: 20
<212> TYPE: DNA
<213> ORGANISM: Homo sapiens
<220> FEATURE:
<221> NAME/KEY: misc_feature
<222> LOCATION: (1)...(20)
<223> OTHER INFORMATION: n = A,T,C or G
```

```
<400> SEQUENCE: 36
caaagcngnn cngagnaguc                                            20

<210> SEQ ID NO 37
<211> LENGTH: 69
<212> TYPE: DNA
<213> ORGANISM: Homo sapiens
<220> FEATURE:
<221> NAME/KEY: misc_feature
<222> LOCATION: (1)...(69)
<223> OTHER INFORMATION: n = A,T,C or G

<400> SEQUENCE: 37
gguggagccc cagggcauua ccucaaagcn gnncngagna gucgugggca aggugggcac   60
ucagguggg                                                        69

<210> SEQ ID NO 38
<211> LENGTH: 60
<212> TYPE: DNA
<213> ORGANISM: Homo sapiens
<220> FEATURE:
<221> NAME/KEY: misc_feature
<222> LOCATION: (1)...(60)
<223> OTHER INFORMATION: n = A,T,C or G

<400> SEQUENCE: 38
gugucucuau ggguuugccc aaagcngnnc ngagnagucu cuggacauuu cauuucauac   60

<210> SEQ ID NO 39
<211> LENGTH: 76
<212> TYPE: DNA
<213> ORGANISM: Homo sapiens
<220> FEATURE:
<221> NAME/KEY: misc_feature
<222> LOCATION: (1)...(76)
<223> OTHER INFORMATION: n = A,T,C or G

<400> SEQUENCE: 39
ggcccucucg ccgucgggcu ccuugcugag caaagcngnn cngagnaguc gaugccgaag   60
ccgaucuugc ugcgcg                                                76

<210> SEQ ID NO 40
<211> LENGTH: 68
<212> TYPE: DNA
<213> ORGANISM: Homo sapiens
<220> FEATURE:
<221> NAME/KEY: misc_feature
<222> LOCATION: (1)...(68)
<223> OTHER INFORMATION: n = A,T,C or G

<400> SEQUENCE: 40
cguuugccug cuaaggagcg aacaaagcng nncngagnag ucgauguuuc uuugugaguc   60
gggcgccg                                                         68

<210> SEQ ID NO 41
<211> LENGTH: 80
<212> TYPE: DNA
<213> ORGANISM: Homo sapiens
<220> FEATURE:
<221> NAME/KEY: misc_feature
<222> LOCATION: (1)...(80)
<223> OTHER INFORMATION: n = A,T,C or G

<400> SEQUENCE: 41
```

```
cgccggacga gcgcagaucg uuuggaccug aacaaagcng nncngagnag uccggggcga    60
ggaggcgagg agaaaagucg                                                80
```

<210> SEQ ID NO 42
<211> LENGTH: 84
<212> TYPE: DNA
<213> ORGANISM: Homo sapiens
<220> FEATURE:
<221> NAME/KEY: misc_feature
<222> LOCATION: (1)...(84)
<223> OTHER INFORMATION: n = A,T,C or G

<400> SEQUENCE: 42

```
ggaguaagga ggggggggag acucuaguuc gcaaagcngn ncngagnagu cagucggcua    60
aggugauggg gguugcagca cacc                                           84
```

<210> SEQ ID NO 43
<211> LENGTH: 16
<212> TYPE: PRT
<213> ORGANISM: Homo sapiens

<400> SEQUENCE: 43

Tyr Thr Asp Thr Gly Lys Ala Ser Gly Asn Leu Glu Thr Lys Tyr Lys
1               5                   10                  15

<210> SEQ ID NO 44
<211> LENGTH: 15
<212> TYPE: PRT
<213> ORGANISM: Homo sapiens

<400> SEQUENCE: 44

Thr Gly Lys Lys Ser Gly Lys Leu Lys Ala Ser Tyr Lys Arg Asp
1               5                   10                  15

<210> SEQ ID NO 45
<211> LENGTH: 1817
<212> TYPE: DNA
<213> ORGANISM: Homo sapiens

<400> SEQUENCE: 45

```
acgaggacga caggctgtgc gcggtctgca cggcgctccg cggcggagct tcatgtgggg    60
ctgcgacccg cgcagccggc gcctcgctga gggaacggac ccccggtaac cggagaccgc   120
cttccccccc accctggcg ccaaaggata tcgtatgttc aggtccaaac gctcggggct   180
ggtgcggcga ctttggcgaa gtcgtgtggt ccccgaccgg aggaaggcg gcagcggcgg   240 cggcggtggc ggcgacgagg atgggagctt ggcagccga gctgagccgg ccccgcgggc   300
aagagagggc ggaggctgcg gccgctccga agtccgcccg gtagccccgc ggcggccccg   360
ggacgcagtg ggacagcgag gcgcccaggg gcgggggagg cgccgcgcg cagggggccc   420 cccgaggccc atgtcggagc caggggccgg cgctgggagc tccctgctgg acgtggcgga   480
gccgggaggc ccgggctggc tgcccgagag tgactgcgag acggtgacct gctgtctctt   540
ttcggagcgg gacgccgccg gcgcgccccg ggacgccagc gaccccctgg ccggggcggc   600
cctggagccg gcgggcggcg ggcggagtcg cgaagcgcgc tcgcggctgc tgctgctgga   660
gcaggaactc aaaaccgtca cgtactcgct gctgaagcgg ctcaaggagc gctcgctgga   720
cacgctgctg gaggcggtgg agtccgcgcg cggcgtgccg gcggctgcg tgctggtgcc   780 gcgcgccgac ctccgcctgg gcggccagcc ccgccgccg cagctgctgc tcggccgcct   840 cttttcgctgg cccgacctgc agcacgccgt ggagctgaag cccctgtgcg gctgccacag   900
```

```
cttcgccgcc gccgccgacg gccctaccgt gtgctgcaac ccctaccact tcagccggct    960
ctgcgggccc gaatctccgc cacctcccta ctctcggctg tctcctcgcg acgagtacaa   1020
gccactggat ctgtccgatt ccacattgtc ttacactgaa acggaggcta ccaactccct   1080
catcactgct ccgggtgaat tctcagacgc cagcatgtct ccggacgcca ccaagccgag   1140
ccactggtgc agcgtggcgt actgggagca ccggacgcgc gtgggccgcc tctatgcggt   1200
gtacgaccag gccgtcagca tcttctacga cctacctcag ggcagcggct tctgcctggg   1260
ccagctcaac ctggagcagc gcagcgagtc ggtgcggcga acgcgcagca agatcggctt   1320
cggcatcctg ctcagcaagg agcccgacgg cgtgtgggcc tacaaccgcg gcgagcaccc   1380
catcttcgtc aactccccga cgctggacgc gcccggcggc cgcgccctgg tcgtgcgcaa   1440
ggtgcccccc ggctactcca tcaaggtgtt cgacttcgag cgctcgggcc tgcagcacgc   1500
gcccgagccc gacgccgccg acggcccta cgacccaac agcgtccgca tcagcttcgc   1560
caagggctgg gggccctgct actcccggca gttcatcacc tcctgcccct gctggctgga   1620
gatcctcctc aacaacccca gatagtggcg gccccggcgg gaggggcggg tgggaggccg   1680
cggccaccgc cacctgccgg cctcgagagg ggccgatgcc cagagacaca gcccccacgg   1740
acaaaacccc ccagatatca tctacctaga tttaatataa agttttatat attatatgga   1800
aaaaaaaaaa aaaaaaa                                                  1817

<210> SEQ ID NO 46
<211> LENGTH: 496
<212> TYPE: PRT
<213> ORGANISM: Homo sapiens

<400> SEQUENCE: 46

Met Phe Arg Ser Lys Arg Ser Gly Leu Val Arg Arg Leu Trp Arg Ser
 1               5                  10                  15

Arg Val Val Pro Asp Arg Glu Gly Gly Ser Gly Gly Gly Gly Gly Gly
            20                  25                  30

Gly Asp Glu Asp Gly Ser Leu Gly Ser Arg Ala Glu Pro Ala Pro Arg
        35                  40                  45

Ala Arg Glu Gly Gly Gly Cys Gly Arg Ser Glu Val Arg Pro Val Ala
    50                  55                  60

Pro Arg Arg Pro Arg Asp Ala Val Gly Gln Arg Gly Ala Gln Gly Ala
65                  70                  75                  80

Gly Arg Arg Arg Arg Ala Gly Gly Pro Pro Arg Pro Met Ser Glu Pro
                85                  90                  95

Gly Ala Gly Ala Gly Ser Ser Leu Leu Asp Val Ala Glu Pro Gly Gly
            100                 105                 110

Pro Gly Trp Leu Pro Glu Ser Asp Cys Glu Thr Val Thr Cys Cys Leu
        115                 120                 125

Phe Ser Glu Arg Asp Ala Ala Gly Ala Pro Arg Asp Ala Ser Asp Pro
    130                 135                 140

Leu Ala Gly Ala Ala Leu Glu Pro Ala Gly Gly Arg Ser Arg Glu
145                 150                 155                 160

Ala Arg Ser Arg Leu Leu Leu Leu Glu Gln Glu Leu Lys Thr Val Thr
                165                 170                 175

Tyr Ser Leu Leu Lys Arg Leu Lys Glu Arg Ser Leu Asp Thr Leu Leu
            180                 185                 190

Glu Ala Val Glu Ser Arg Gly Gly Val Pro Gly Gly Cys Val Leu Val
        195                 200                 205
```

-continued

```
Pro Arg Ala Asp Leu Arg Leu Gly Gly Gln Pro Ala Pro Pro Gln Leu
    210                 215                 220
Leu Leu Gly Arg Leu Phe Arg Trp Pro Asp Leu Gln His Ala Val Glu
225                 230                 235                 240
Leu Lys Pro Leu Cys Gly Cys His Ser Phe Ala Ala Ala Asp Gly
            245                 250                 255
Pro Thr Val Cys Cys Asn Pro Tyr His Phe Ser Arg Leu Cys Gly Pro
            260                 265                 270
Glu Ser Pro Pro Pro Tyr Ser Arg Leu Ser Pro Arg Asp Glu Tyr
            275                 280                 285
Lys Pro Leu Asp Leu Ser Asp Ser Thr Leu Ser Tyr Thr Glu Thr Glu
    290                 295                 300
Ala Thr Asn Ser Leu Ile Thr Ala Pro Gly Glu Phe Ser Asp Ala Ser
305                 310                 315                 320
Met Ser Pro Asp Ala Thr Lys Pro Ser His Trp Cys Ser Val Ala Tyr
            325                 330                 335
Trp Glu His Arg Thr Arg Val Gly Arg Leu Tyr Ala Val Tyr Asp Gln
            340                 345                 350
Ala Val Ser Ile Phe Tyr Asp Leu Pro Gln Gly Ser Gly Phe Cys Leu
            355                 360                 365
Gly Gln Leu Asn Leu Glu Gln Arg Ser Glu Ser Val Arg Arg Thr Arg
    370                 375                 380
Ser Lys Ile Gly Phe Gly Ile Leu Leu Ser Lys Glu Pro Asp Gly Val
385                 390                 395                 400
Trp Ala Tyr Asn Arg Gly Glu His Pro Ile Phe Val Asn Ser Pro Thr
            405                 410                 415
Leu Asp Ala Pro Gly Gly Arg Ala Leu Val Val Arg Lys Val Pro Pro
            420                 425                 430
Gly Tyr Ser Ile Lys Val Phe Asp Phe Glu Arg Ser Gly Leu Gln His
        435                 440                 445
Ala Pro Glu Pro Asp Ala Ala Asp Gly Pro Tyr Asp Pro Asn Ser Val
    450                 455                 460
Arg Ile Ser Phe Ala Lys Gly Trp Gly Pro Cys Tyr Ser Arg Gln Phe
465                 470                 475                 480
Ile Thr Ser Cys Pro Cys Trp Leu Glu Ile Leu Leu Asn Asn Pro Arg
            485                 490                 495
```